United States Patent
Liu et al.

(10) Patent No.: US 10,822,327 B2
(45) Date of Patent: Nov. 3, 2020

(54) 2-SUBSTITUTED AROMATIC RING-PYRIMIDINE DERIVATIVE AND PREPARATION AND APPLICATION THEREOF

(71) Applicants: ZHEJIANG UNIVERSITY, Zhejiang (CN); SHANGHAI INSTITUTE OF MATERIA MEDICA, CHINESE ACADEMY OF SCIENCES, Shanghai (CN)

(72) Inventors: Tao Liu, Zhejiang (CN); Jia Li, Shanghai (CN); Yongzhou Hu, Zhejiang (CN); Yubo Zhou, Shanghai (CN); Xiaowu Dong, Zhejiang (CN); Anhui Gao, Shanghai (CN); Pinrao Song, Zhejiang (CN); Peipei Wang, Shanghai (CN); Lexian Tong, Zhejiang (CN); Xiaobei Hu, Shanghai (CN); Mingbo Su, Shanghai (CN)

(73) Assignees: ZHEJIANG UNIVERSITY, Zhejiang (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/348,502

(22) PCT Filed: Nov. 8, 2017

(86) PCT No.: PCT/CN2017/110030
§ 371 (c)(1),
(2) Date: Aug. 19, 2019

(87) PCT Pub. No.: WO2018/086547
PCT Pub. Date: May 17, 2018

(65) Prior Publication Data
US 2019/0375727 A1    Dec. 12, 2019

(30) Foreign Application Priority Data
Nov. 10, 2016 (CN) .......................... 2016 1 0988060

(51) Int. Cl.
| C07D 401/14 | (2006.01) |
| A61P 35/00 | (2006.01) |
| C07D 401/12 | (2006.01) |
| C07D 405/14 | (2006.01) |
| C07D 409/14 | (2006.01) |
| C07D 413/14 | (2006.01) |
| C07D 417/14 | (2006.01) |

(52) U.S. Cl.
CPC ............ *C07D 401/14* (2013.01); *A61P 35/00* (2018.01); *C07D 401/12* (2013.01); *C07D 405/14* (2013.01); *C07D 409/14* (2013.01); *C07D 413/14* (2013.01); *C07D 417/14* (2013.01)

(58) Field of Classification Search
CPC .................................................... C07D 401/14
USPC ....................................................... 514/235.8
See application file for complete search history.

(56) References Cited

FOREIGN PATENT DOCUMENTS

CN         102203086 A    *    9/2011    ........... C07D 409/12

* cited by examiner

*Primary Examiner* — Kahsay Habte

(57) ABSTRACT

A 2-substituted aromatic ring-pyrimidine derivative as shown in a general formula I, and an optical isomer or a pharmaceutically acceptable salt or a solvate thereof are provided. The present invention designs and synthesizes a series of novel small molecular Chk1 inhibitors by using N-substituted pyridin-2-aminopyrimidine obtained through structure-based virtual screening as a lead compound, and carries out Chk1 kinase inhibitory activity test. The experiment confirmed that said compounds possess strong anti-cancer effect, Chk1 kinase inhibitory activity and are promising Chk1 inhibitors. The compounds can be used as new cancer therapeutic drugs, which can be applied to treat solid tumors or hematologic tumors related to proliferative disease of human or animal.

9 Claims, 1 Drawing Sheet

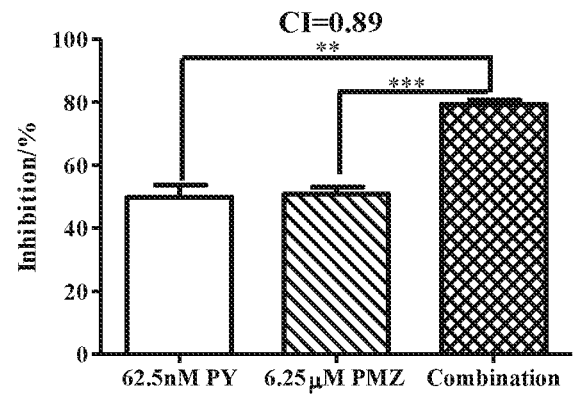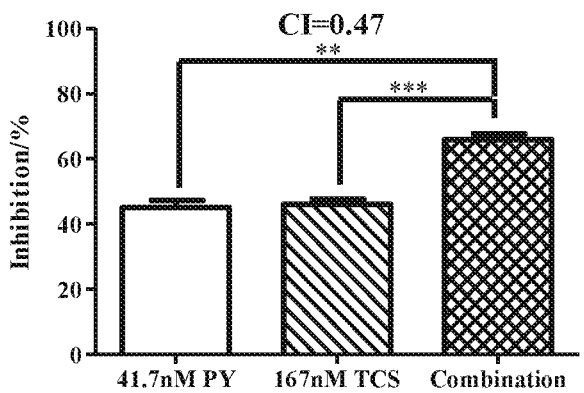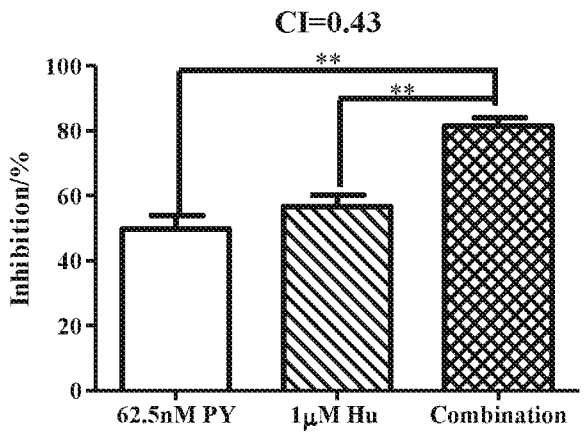

2-SUBSTITUTED AROMATIC RING-PYRIMIDINE DERIVATIVE AND PREPARATION AND APPLICATION THEREOF

CROSS REFERENCE OF RELATED APPLICATION

This is a U.S. National Stage under 35 U.S.C 371 of the International Application PCT/CN2017/110030, filed Nov. 8, 2017, which claims priority under 35 U.S.C. 119(a-d) to CN 201610988060.8, filed Nov. 10, 2016.

BACKGROUND OF THE PRESENT INVENTION

Field of Invention

The present invention relates to a medicine field, and more particularly to a 2-substituted aromatic ring-pyrimidine derivative, and an optical isomer or a pharmaceutically acceptable salt or a solvate thereof, and a pharmaceutical composition containing the derivative, and application as Chk1 inhibitors in preparation of antitumor drugs.

Description of Related Arts

With the changes in human living environment and the aging of the population, malignant tumors are seriously threatening human life. In China, malignant tumors have become the first deadly disease. Conventional treatment of cancer include surgery, radiation therapy and drug chemotherapy, among which drug chemotherapy is the most important. In recent years, as tumor molecular targets have been gradually explained, many targeted anti-tumor drugs have entered clinical applications, but due to the complexity of the tumors and genetic diversity, single-targeted drugs are not enough to cure tumors. Conventional chemotherapeutic drugs are mostly DNA-damaging drugs, which induce tumor cell apoptosis by directly interfering with DNA synthesis of tumor cells, regulating DNA transcription and repair, and prolonging the survival of cancer patients. However, due to its poor selectivity, it can cause a variety of toxic side effects, and it will produce significant drug resistance during the treatment. Therefore, according to the characteristics of DNA-damaging drugs, drugs with low toxicity are developed to be combined with DNA-damaging drugs, which can enhance the therapeutic effect of DNA-damaging drugs while reducing the dose of DNA damage drugs, so as to reduce the risk of toxic side effects and multidrug resistance. Among them, the development of cell cycle-related drugs and their strategies in combination with DNA-damaging drugs have attracted great interest and attention from drug researchers in recent years.

Eukaryotic cells have their own regulatory mechanisms. When exposed to external stimuli such as radiotherapy or chemotherapy, it can be temporarily blocked in the G1, S or G2/M phase for DNA repair, and it will enter the next phase after repair. A large number of protein kinases in cells interact with the same or different signaling pathways, forming an intricate signal network that regulates cell growth, proliferation, angiogenesis, metastasis, apoptosis and other life activities. Among them, the tumor gene suppressor protein p53 is mainly responsible for the regulation of the G1 checkpoint, while the S and G2/M phases are mainly regulated by the cell cycle checkpoint kinase 1 (Chk1). Most tumor cells rely more on S or G2/M phase arrest due to the loss of p53 function as a defense mechanism for DNA damage-induced apoptosis. In the p53-deficient tumor cells, inhibition of Chk1 protein can abrogate cell cycle arrest and directly induce tumor cell apoptosis, while normal cells are temporarily blocked in G1 phase due to the existence of intact p53 regulatory mechanism. Therefore, Chk1 inhibitor can be used as an adjuvant therapy to selectively enhance the sensitivity of tumor cells to radiotherapy or chemotherapy and improve the therapeutic effect.

In addition, in the context of specific genetic defects, such as the inherent DNA damage is too high to cause large replication pressure, Chk1 inhibitors can also be used alone for killing tumor cells through a "synthetic lethal" mechanism to achieve therapeutic purpose. Based on this therapeutic strategy, Chk1 inhibitors can be used alone in the treatment of B-cell lymphoma, leukemia, neuroblastoma, and some sensitive tumors with high expression of proto-oncogenes such as breast and lung cancer.

In the past two decades, small molecular compounds of different structural types have been discovered as Chk1 inhibitors, and these compounds have shown strong anti-tumor effects in preclinical evaluation. Conventionally, 11 small molecular Chk1 inhibitors have entered clinic research, which proves the correctness of Chk1 as a tumor treatment target.

The present invention designs and synthesizes a series of novel small molecular Chk1 inhibitors by using 2-aminopyrimidine as a lead compound obtained by structure-based virtual screening, and tests the compounds at the molecular level of Chk1 kinase inhibitory activity. The results showed that most of the compounds exhibited moderate to strong Chk1 inhibitory activity and were promising Chk1 inhibitors, providing new ideas for the study of cancer therapeutic drugs.

SUMMARY OF THE PRESENT INVENTION

An object of the present invention is to provide a 2-substituted aromatic ring-pyrimidine derivative, and an optical isomer or a pharmaceutically acceptable salt or a solvate thereof, which has strong anti-cancer effect with Chk1 inhibition.

The present invention presents a 2-substituted aromatic ring-pyrimidine derivative, and an optical isomer or a pharmaceutically acceptable salt or a solvate thereof, wherein the 2-substituted aromatic ring-pyrimidine derivative has a structure as shown in a general formula I:

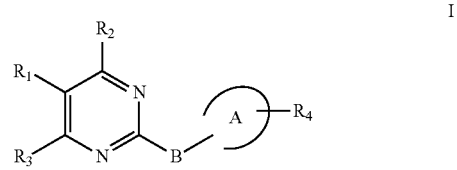

wherein ring A comprises 1 to 3 substituted or unsubstituted penta- or hexa-heterocyclic aryl selected from O, N and S; and a substituent is $R_4$;

B is selected from —NH,

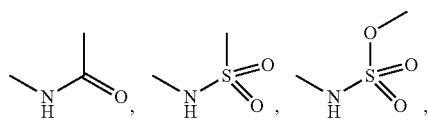

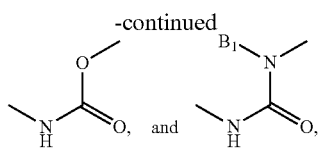

wherein $B_1$ is selected from H, $C_{1-4}$ alkyl, halogenated $C_{1-4}$ alkyl, $C_{1-4}$ alkoxy, and halogenated $C_{1-4}$ alkoxy;

$R_1$ is selected from halogen atom, $C_{1-6}$ alkyl, halogenated $C_{1-6}$ alkyl, $C_{3-6}$ cycloalkyl, halogenated $C_{3-6}$ cycloalkyl, $C_{1-6}$ alkoxy, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, and an unsubstituted or substituted penta- or hexa-aromatic ring or aromatic heterocyclic ring, wherein the aromatic heterocyclic ring comprises 1 to 3 hetero atoms selected from O, N and S, substitution is mono-, di- or tri-substitution, and a substituent is $R_a$;

$R_a$ is selected from H, halogen, nitro, cyano, $C_{1-3}$ alkyl, halogenated $C_{1-3}$ alkyl, —C(=O)O$R_b$, —C(=O)NH$R_b$, —NH$R_b$, —O$R_b$, and —NHCO$R_b$; $R_b$ is selected from H, $C_{1-3}$ alkyl, halogenated $C_{1-3}$ alkyl, $C_{1-3}$ alkoxy, halogenated $C_{1-3}$ alkoxy, and $C_{1-7}$ alkylamine;

$R_2$ is selected from H, —NH$R_c$, —N($R_c$)$_2$, —O$R_c$, and —S$R_c$; $R_c$ is selected from penta- to octa-aliphatic ring containing 1 to 3 heteroatoms selected from O and N, $C_{1-7}$ alkyl, $C_{1-7}$ hydroxyalkyl, $C_{1-7}$ alkylamino, and $C_{1-7}$ alkoxy;

$R_3$ is selected from halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, and halogenated $C_{1-3}$ alkylamino;

$R_4$ is selected from H, halogen, nitro, cyano, trifluoromethyl, $C_{1-3}$ alkyl, $C_{1-3}$ alkoxy, amide, substituted alkyl amide.

Preferably, the 2-substituted aromatic ring-pyrimidine derivative has a structure as shown in a general formula II:

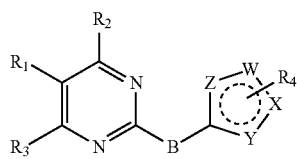

wherein W, X, Y and Z are identical or different and are independently selected from N, C and O;

B is selected from —NH,

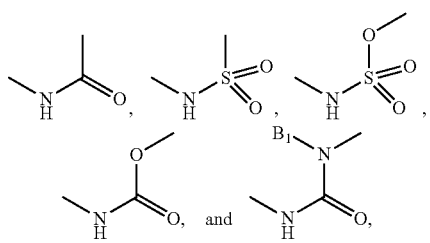

wherein $B_1$ is selected from H, $C_{1-4}$ alkyl, halogenated $C_{1-4}$ alkyl, $C_{1-4}$ alkoxy, and halogenated $C_{1-4}$ alkoxy;

$R_1$ is selected from halogen atom, $C_{1-6}$ alkyl, halogenated $C_{1-6}$ alkyl, $C_{3-6}$ cycloalkyl, halogenated $C_{3-6}$ cycloalkyl, $C_{1-6}$ alkoxy, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, and an unsubstituted or substituted penta- or hexa-aromatic ring or aromatic heterocyclic ring, wherein the aromatic heterocyclic ring comprises 1 to 3 hetero atoms selected from O, N and S, substitution is mono-, di- or tri-substitution, and a substituent is $R_a$;

$R_a$ is selected from H, halogen, nitro, cyano, $C_{1-3}$ alkyl, halogenated $C_{1-3}$ alkyl, —C(=O)O$R_b$, —C(=O)NH$R_b$, —NH$R_b$, —O$R_b$, and —NHCO$R_b$; $R_b$ is selected from H, $C_{1-3}$ alkyl, halogenated $C_{1-3}$ alkyl, $C_{1-3}$ alkoxy, halogenated $C_{1-3}$ alkoxy, and $C_{1-7}$ alkylamine;

$R_2$ is selected from H, —NH$R_c$, —N($R_c$)$_2$, —O$R_c$, and —S$R_c$; $R_c$ is selected from penta- to octa-aliphatic ring containing 1 to 3 heteroatoms selected from O and N, $C_{1-7}$ alkyl, $C_{1-7}$ hydroxyalkyl, $C_{1-7}$ alkylamino, and $C_{1-7}$ alkoxy;

$R_3$ is selected from halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, and halogenated $C_{1-3}$ alkylamino;

$R_4$ is selected from H, halogen, nitro, cyano, trifluoromethyl, $C_{1-3}$ alkyl, $C_{1-3}$ alkoxy, amide, substituted alkyl amide.

Preferably, the 2-substituted aromatic ring-pyrimidine derivative has a structure as shown in a general formula III:

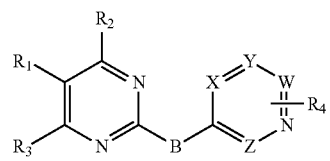

wherein W, X, Y and Z are identical or different and are independently selected from N and C;

B is selected from —NH,

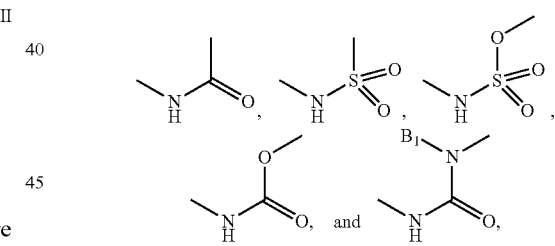

wherein $B_1$ is selected from H, $C_{1-4}$ alkyl, halogenated $C_{1-4}$ alkyl, $C_{1-4}$ alkoxy, and halogenated $C_{1-4}$ alkoxy;

$R_1$ is selected from halogen atom, $C_{1-6}$ alkyl, halogenated $C_{1-6}$ alkyl, $C_{3-6}$ cycloalkyl, halogenated $C_{3-6}$ cycloalkyl, $C_{1-6}$ alkoxy, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, and an unsubstituted or substituted penta- or hexa-aromatic ring or aromatic heterocyclic ring, wherein the aromatic heterocyclic ring comprises 1 to 3 hetero atoms selected from O, N and S, substitution is mono-, di- or tri-substitution, and a substituent is $R_a$;

$R_a$ is selected from H, halogen, nitro, cyano, $C_{1-3}$ alkyl, halogenated $C_{1-3}$ alkyl, —C(=O)O$R_b$, —C(=O)NH$R_b$, —NH$R_b$, —O$R_b$, and —NHCO$R_b$; $R_b$ is selected from H, $C_{1-3}$ alkyl, halogenated $C_{1-3}$ alkyl, $C_{1-3}$ alkoxy, halogenated $C_{1-3}$ alkoxy, and $C_{1-7}$ alkylamine;

$R_2$ is selected from H, —NH$R_c$, —N($R_c$)$_2$, —O$R_c$, and —S$R_c$; $R_c$ is selected from penta- to octa-aliphatic ring containing 1 to 3 heteroatoms selected from O and N, $C_{1-7}$ alkyl, $C_{1-7}$ hydroxyalkyl, $C_{1-7}$ alkylamino, and $C_{1-7}$ alkoxy;

$R_3$ is selected from halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, and halogenated $C_{1-3}$ alkylamino;

$R_4$ is selected from H, halogen, nitro, cyano, trifluoromethyl, $C_{1-3}$ alkyl, $C_{1-3}$ alkoxy, amide, substituted alkyl amide.

Preferably, the 2-substituted aromatic ring-pyrimidine derivative has a structure as shown in a general formula IV:

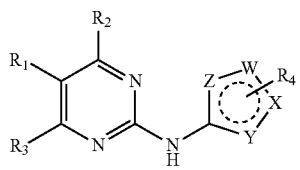

IV wherein W, X, Y and Z are identical or different and are independently selected from N, C and O;

$R_1$ is selected from halogen atom, $C_{1-6}$ alkyl, halogenated $C_{1-6}$ alkyl, $C_{3-6}$ cycloalkyl, halogenated $C_{3-6}$ cycloalkyl, $C_{1-6}$ alkoxy, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, and an unsubstituted or substituted penta- or hexa-aromatic ring or aromatic heterocyclic ring, wherein the aromatic heterocyclic ring comprises 1 to 3 hetero atoms selected from O, N and S, substitution is mono-, di- or tri-substitution, and a substituent is $R_a$;

$R_a$ is selected from H, halogen, nitro, cyano, $C_{1-3}$ alkyl, halogenated $C_{1-3}$ alkyl, —C(═O)$OR_b$, —C(═O)$NHR_b$, —$NHR_b$, —$OR_b$, and —$NHCOR_b$; $R_b$ is selected from H, $C_{1-3}$ alkyl, halogenated $C_{1-3}$ alkyl, $C_{1-3}$ alkoxy, halogenated $C_{1-3}$ alkoxy, and $C_{1-7}$ alkylamine;

$R_2$ is selected from H, —$NHR_c$, —$N(R_c)_2$, —$OR_c$, and —$SR_c$; $R_c$ is selected from penta- to octa-aliphatic ring containing 1 to 3 heteroatoms selected from O and N, $C_{1-7}$ alkyl, $C_{1-7}$ hydroxyalkyl, $C_{1-7}$ alkylamino, and $C_{1-7}$ alkoxy;

$R_3$ is selected from halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, and halogenated $C_{1-3}$ alkylamino;

$R_4$ is selected from H, halogen, nitro, cyano, trifluoromethyl, $C_{1-3}$ alkyl, $C_{1-3}$ alkoxy, amide, substituted alkyl amide.

Preferably, the derivative of the general formula IV of the present invention is selected from:

5-(1-methyl-1H-pyrazol-4-yl)-$N^2$-(3-methylpyrazol-5-yl)-$N^4$-(piperidin-4-yl)-2,4-diaminopyrimidine, 5-(1-methyl-1H-pyrazol-4-yl)-$N^2$-(5-methyloxazol-3-yl)-$N^4$-(piperidin-4-yl)-2,4-diaminopyrimidine, 5-(thien-2-yl)-$N^2$-(5-methylpyrazol-3-yl)-$N^4$-(piperidin-4-yl)-2,4-diaminopyrimidine, 5-(thien-2-yl)-$N^2$-(5-methyloxazol-3-yl)-$N^4$-(piperidin-4-yl)-2,4-diaminopyrimidine, 5-(furan-2-yl)-$N^2$-(5-methylpyrazol-3-yl)-$N^4$-(piperidin-4-yl)-2,4-diaminopyrimidine, and 5-(furan-2-yl)-$N^2$-(5-methyloxazol-3-yl)-$N^4$-(piperidin-4-yl)-2,4-diaminopyrimidine.

Preferably, the 2-substituted aromatic ring-pyrimidine derivative has a structure as shown in a general formula V:

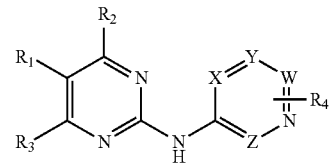

V wherein W, X, Y and Z are identical or different and are independently selected from N and C;

$R_1$ is selected from halogen atom, $C_{1-6}$ alkyl, halogenated $C_{1-6}$ alkyl, $C_{3-6}$ cycloalkyl, halogenated $C_{3-6}$ cycloalkyl, $C_{1-6}$ alkoxy, halogenated $C_{1-6}$ alkoxy, $C_{2-6}$ alkenyl, $C_{2-6}$ hydroxy substituted alkenyl, $C_{2-6}$ alkynyl, $C_{2-6}$ hydroxy substituted alkynyl, and an unsubstituted or substituted penta- or hexa-aromatic ring or aromatic heterocyclic ring, wherein the aromatic heterocyclic ring comprises 1 to 3 hetero atoms selected from O, N and S, substitution is mono-, di- or tri-substitution, and a substituent is $R_a$;

$R_a$ is selected from H, halogen, nitro, cyano, $C_{1-3}$ alkyl, halogenated $C_{1-3}$ alkyl, —C(═O)$OR_b$, —C(═O)$NHR_b$, —$NHR_b$, —$OR_b$, and —$NHCOR_b$; $R_b$ is selected from H, $C_{1-3}$ alkyl, halogenated $C_{1-3}$ alkyl, $C_{1-3}$ alkoxy, halogenated $C_{1-3}$ alkoxy, and $C_{1-7}$ alkylamine;

$R_2$ is selected from H, —$NHR_c$, —$N(R_c)_2$, —$OR_c$, and —$SR_c$; $R_c$ is selected from penta- to octa-aliphatic ring containing 1 to 3 heteroatoms selected from O and N, $C_{1-7}$ alkyl, $C_{1-7}$ hydroxyalkyl, $C_{1-7}$ alkylamino, and $C_{1-7}$ alkoxy;

$R_3$ is selected from halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, and halogenated $C_{1-3}$ alkylamino;

$R_4$ is selected from H, halogen, nitro, cyano, trifluoromethyl, $C_{1-3}$ alkyl, $C_{1-3}$ alkoxy, amide, substituted alkyl amide.

Preferably, the derivative of the general formula V of the present invention is selected from:

5-phenyl-$N^2$-(2-cyanopyridin-5-yl)-$N^4$-(piperidin-4-methyl)-2,4-diaminopyrimidine, 5-(3-fluorophenyl)-$N^2$-(2-cyanopyridin-5-yl)-$N^4$-(piperidin-4-methyl)-2,4-diaminopyrimidine, 5-(1-methyl-1H-pyrazol-4-yl)-$N^2$-(2-cyanopyridin-5-yl)-$N^4$-(piperidin-4-methyl)-2,4-diaminopyrimidine, 5-trifluoromethyl-$N^2$-(2-cyanopyridin-5-yl)-$N^4$-(piperidin-4-methyl)-2,4-diaminopyrimidine, 5-(3-fluorophenyl)-$N^2$-(2-cyanopyridin-5-yl)-$N^4$-aminoethyl-2,4-diaminopyrimidine, 5-(1-methyl-1H-pyrazol-4-yl)-$N^2$-(2-cyanopyridin-5-yl)-$N^4$-aminoethyl-2,4-diaminopyrimidine, 5-(3-fluorophenyl)-$N^2$-(2-cyanopyridin-5-yl)-$N^4$-(2-morpholinethyl)-2,4-diaminopyrimidine, 5-(1-methyl-1H-pyrazol-4-yl)-$N^2$-(2-cyanopyridin-5-yl)-$N^4$-(2-morpholinethyl)-2,4-diaminopyrimidine, 5-(3-fluorophenyl)-$N^2$-(2-cyanopyridin-5-yl)-$N^4$-(piperidin-4-yl)-2,4-diaminopyrimidine, 5-(1-methyl-1H-pyrazol-4-yl)-$N^2$-(2-cyanopyridin-5-yl)-$N^4$-(piperidin-4-yl)-2,4-diaminopyrimidine, 5-(thien-2-yl)-$N^2$-(2-cyanopyridin-5-yl)-$N^4$-(piperidin-4-yl)-2,4-diaminopyrimidine, 5-(furan-2-yl)-$N^2$-(2-cyanopyridin-5-yl)-$N^4$-(piperidin-4-yl)-2,4-diaminopyrimidine, 5-(5-methoxycarbonylthiophen-2-yl)-$N^2$-(2-cyanopyridin-5-yl)-$N^4$-(piperidin-4-yl)-2,4-diaminopyrimidine, 5-(5-methoxycarbonylfuran-2-yl)-$N^2$-(2-cyanopyridine-5-yl)-$N^4$-(piperidin-4-yl)-2,4-diaminopyrimidine, 5-trifluoromethyl-$N^2$-(2-cyanopyridin-5-yl)-$N^4$-(piperidin-4-yl)-2,4-diaminopyrimidine,
(R)-5-(1-methyl-1H-pyrazol-4-yl)-$N^2$-(2-cyanopyridin-5-yl)-$N^4$-(piperidin-3-yl)-2,4-diaminopyrimidine,
(S)-5-(1-Methyl-1H-pyrazol-4-yl)-$N^2$-(2-cyanopyridin-5-yl)-$N^4$-(piperidin-3-yl)-2,4-diaminopyrimidine,
(R)-5-trifluoromethyl-$N^2$-(2-cyanopyridin-5-yl)-$N^4$-(piperidin-3-yl)-2,4-diaminopyrimidine,
(R)-5-(1-methyl-1H-pyrazol-4-yl)-N-(2-cyanopyridin-5-yl)-4-(3-aminopiperidin-1-yl)-2-aminopyrimidine,
5-(3-fluorophenyl)-$N^2$-(2-cyanopyrimidin-5-yl)-$N^4$-(2-morpholinethyl)-2,4-diaminopyrimidine,
5-(1-methyl-1H-pyrazol-4-yl)-$N^2$-(2-cyanopyrimidin-5-yl)-$N^4$-(2-morpholinethyl)-2,4-diaminopyrimidine,
5-(1-methyl-1H-pyrazol-4-yl)-$N^2$-(pyridazin-5-yl)-$N^4$-(piperidin-4-yl)-2,4-diaminopyrimidine,
5-(1-methyl-1H-pyrazol-4-yl)-$N^2$-(3-cyanopyridin-6-yl)-$N^4$-(piperidin-4-yl)-2,4-diaminopyrimidine,
5-(1-methyl-1H-pyrazol-4-yl)-$N^2$-(2-cyanopyrazin-5-yl)-$N^4$-(piperidin-4-yl)-2,4-diaminopyrimidine,
5-bromo-$N^2$-(2-cyanopyridin-5-yl)-$N^4$-(piperidin-4-yl)-2,4-diaminopyrimidine,
5-(4-methylthiazol-2-yl)-$N^2$-(2-cyanopyridin-5-yl)-$N^4$-(piperidin-4-yl)-2,4-diaminopyrimidine,
5-bromo-N-(2-cyanopyridin-5-yl)-2-aminopyrimidine,
5-(2-aminophenyl)-N-(2-cyanopyridin-5-yl)-2-aminopyrimidine,
5-(2-(piperidin-4-yl)aminophenyl)-N-(2-cyanopyridin-5-yl)-2-aminopyrimidine,
5-(2-(piperidin-4-methyl)aminophenyl)-N-(2-cyanopyridin-5-yl)-2-aminopyrimidine, and
pharmaceutically acceptable salts or solvates of the above compounds.

The present invention adopts a method familiar to technicians in this field to prepare salt of 2-substituted pyrimidine derivatives described in the present invention. The salt may be an organic acid salt, a mineral acid salt and so on, and the organic acid salt includes a citrate, a fumarate, an oxalate, a malate, a L-malate, and a D-malate, lactate, camphorsulfonate, p-toluenesulfonate, methanesulfonate, benzoate, etc.; the inorganic acid salt includes a hydrohalide, a sulfate, a phosphate, a nitrate, and so on. For example, with a lower alkylsulfonic acid such as methanesulfonic acid, trifluoromethanesulfonic acid or the like may form a mesylate salt, a triflate salt; and an arylsulfonic acid such as benzenesulfonic acid or p-toluenesulfonic acid; with organic carboxylic acids such as acetic acid, fumaric acid, tartrate, L-tartaric acid, D-tartaric acid, oxalic acid, maleic acid, malate, L-malic acid, D-malic acid, succinic acid or citric acid and so on may form corresponding salts; and with an amino acid such as glutamic acid or aspartic acid may form a glutamate or an aspartate. Corresponding salts may also be formed with inorganic acids such as hydrohalic acids (e.g., hydrofluoric acid, hydrobromic acid, hydroiodic acid, hydrochloric acid), nitric acid, carbonic acid, sulfuric acid or phosphoric acid.

The second purpose of the present invention is to provide a pharmaceutical composition comprising at least one active ingredient together with one or more pharmaceutically acceptable carriers or excipients, said active ingredient may be one or more of a 2-substituted pyrimidine compound of the present invention, an optical isomer of the compound, a solvate of the compound or an optical isomer thereof in a pharmaceutically acceptable salt, the compound or an optical isomer thereof.

The carrier includes conventional diluents, excipients, fillers, binders, wetting agents, disintegrating agents, absorption enhancers, surfactants, adsorption carriers, lubricants, etc. in the pharmaceutical field, etc. and fragrances, sweetener may also be added if necessary. The medicament of the present invention can be prepared into various forms such as tablets, powders, granules, capsules, oral liquids and injectable preparations, and the medicaments of the above respective dosage forms can be prepared according to a conventional method in the pharmaceutical field.

The present invention also provides a compound of the general formula (I) to the general formula (V), and an optical isomer thereof, or a pharmaceutically acceptable salt or solvate thereof, and an optical isomer thereof, or a pharmaceutically acceptable compound thereof used alone and/or in combination with radiation therapy, other drugs, in the preparation of drugs for treating Chk1 mediate diseases. The proliferative diseases include tumors, and the tumors are breast cancer, ovarian cancer, narcoma, lung cancer, prostate cancer, colon cancer, rectal cancer, renal cancer, pancreatic cancer, blood cancer, lymphoma, neuroblastoma, and glioma, head cancer, neck cancer, thyroid cancer, liver cancer, vulvar cancer, cervical cancer, endometrial cancer, testicular cancer, bladder cancer, esophageal cancer, stomach cancer, nasopharyngeal cancer, buccal cancer, oral cancer, gastrointestinal stromal tumor, skin cancer, multiple myeloma. The antitumor agent which can be used in combination with the compound provided by the present invention or a pharmaceutically acceptable salt intended includes, but is not limited to, at least one of the following classes: antimetabolite (gemcitabine, 5-fluorouracil, hydroxyurea, pemetrexed); bioalkylatingagengts (eg cisplatin, carboplatin); topoisomerase inhibitors (irinotecan, doxorubicin); small molecular inhibitors (MEK inhibitors, PARP inhibitors, Scr kinase inhibitors, mTOR inhibitors, farnesyltransferase inhibitors, etc.).

Another object of the present invention is to provide a preparative method of the above target compounds, comprising steps of:

method I:
using 5-bromo-2,4-dichloropyrimidine as a starting material, substituting with an aliphatic amine group and an aromatic heterocyclic amine group in sequence, and obtaining a target compound by Suzuki coupling;

method II:
using 5-bromo-2,4-dichloropyrimidine as a starting material, substituting with an aliphatic amine group and aminating in sequence to obtain a 5-bromo-pyrimidine-2,4-diamine intermediate, and processing the intermediate with Suzuki coupling before reacting with a brominated aromatic heterocyclic compound to obtain a target compound;

method III:
using 5-bromo-2,4-dichloropyrimidine as a starting material, substituting with an aliphatic amine group and aminating in sequence to obtain a 5-bromo-pyrimidine-2,4-diamine intermediate, acting the intermediate with a brominated aromatic heterocyclic compound, and then processing with Suzuki coupling and deprotecting a Boc protective group to obtain a target compound;

method IV:
using 5-bromo-2-aminopyrimidine as a starting material, reacting with a brominated aromatic heterocyclic compound before Suzuki coupling, reductive amination and deprotecting a Boc protective group in sequence to obtain a target compound; or method V:
using 5-trifluoromethyl-2,4-dichloropyrimidine as a starting material, substituting with an aliphatic amine group and aminating in sequence to obtain a 5-trifluoromethyl-pyrimidine-2,4-diamine intermediate, then acting the intermediate with a brominated aromatic heterocyclic compound to obtain a target compound.
Compounds 1-6 are prepared according to the following synthetic route:
Compounds 7-27 are prepared according to the following synthetic route:
Compounds 28-29 are prepared according to the following synthetic route:
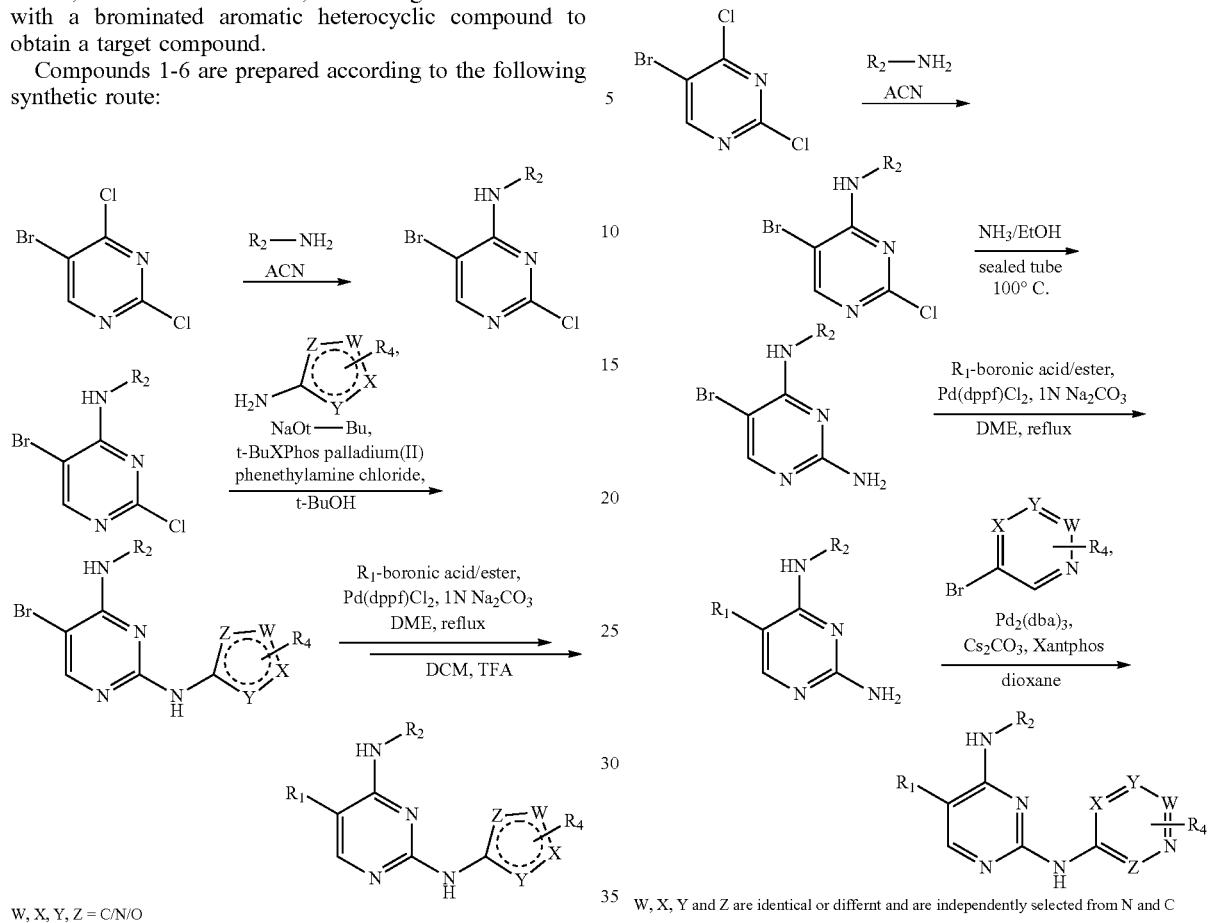
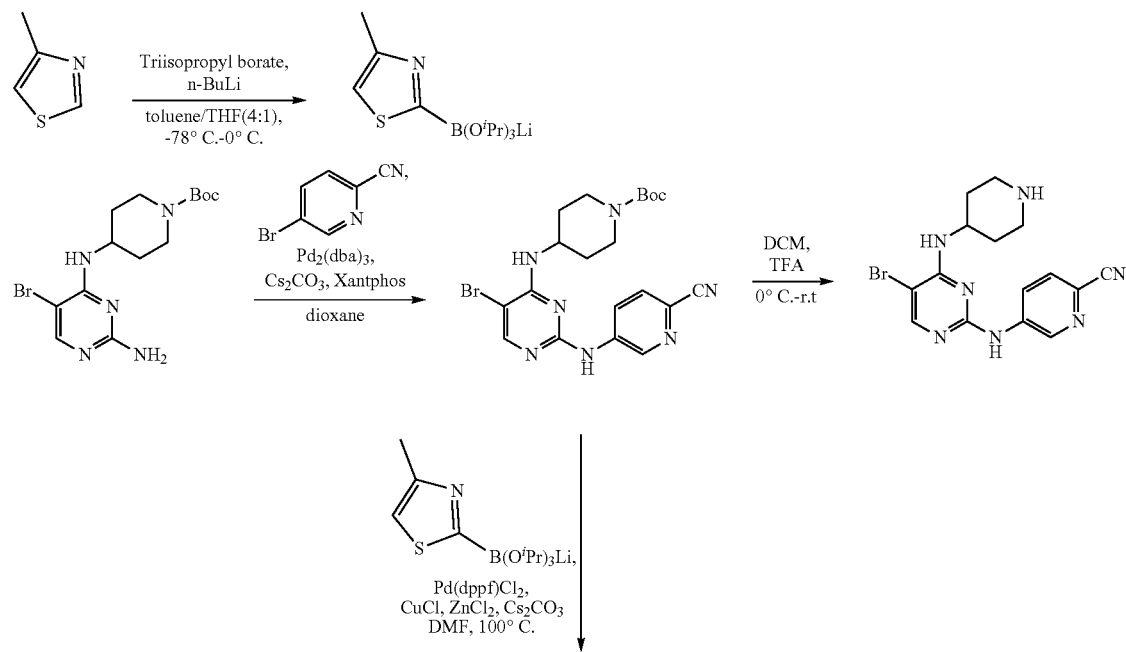

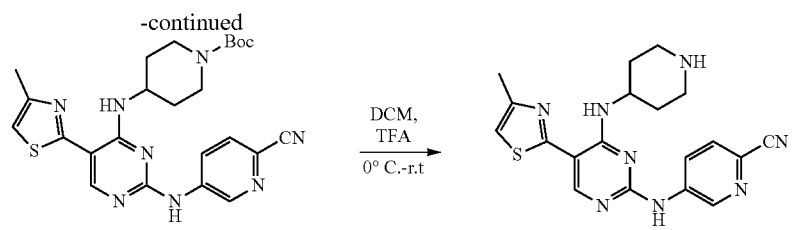

Compounds 30-33 are prepared according to the following synthetic route:

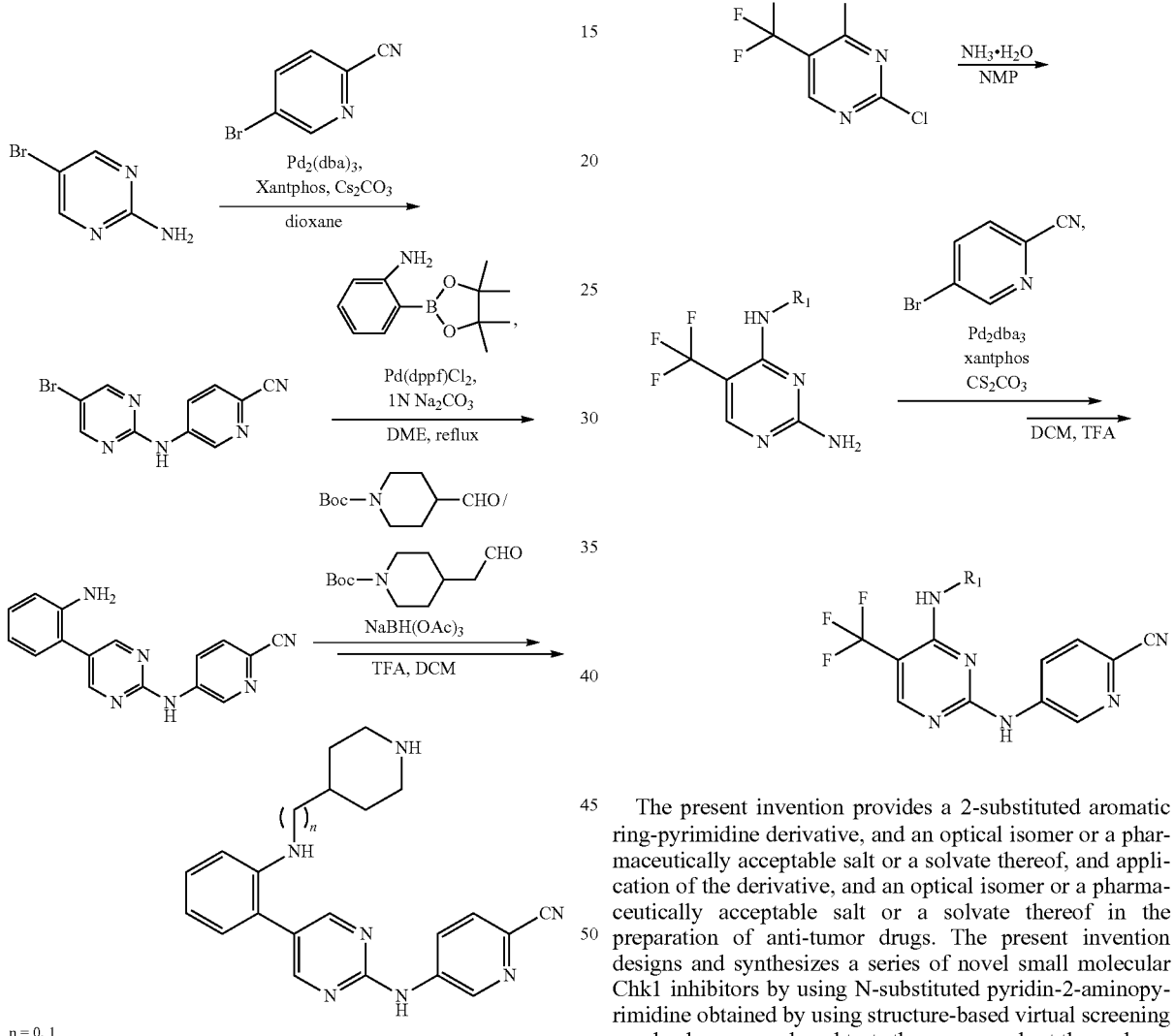

n = 0, 1

Compounds 34-36 are prepared according to the following synthetic route:

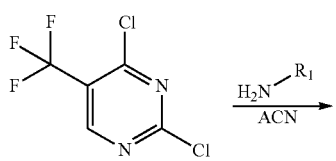

The present invention provides a 2-substituted aromatic ring-pyrimidine derivative, and an optical isomer or a pharmaceutically acceptable salt or a solvate thereof, and application of the derivative, and an optical isomer or a pharmaceutically acceptable salt or a solvate thereof in the preparation of anti-tumor drugs. The present invention designs and synthesizes a series of novel small molecular Chk1 inhibitors by using N-substituted pyridin-2-aminopyrimidine obtained by using structure-based virtual screening as a lead compound, and tests the compounds at the molecular level of Chk1 kinase inhibitory activity. The present invention proves by experiments that the compounds are promising Chk1 inhibitors with strong anti-cancer effect, and medium to strong Chk1 kinase inhibitory activity. The compounds are new cancer therapeutic drugs, which can be applied to treat solid tumors or blood cancers associated with cell proliferation in humans or animals.

BRIEF DESCRIPTION OF THE DRAWINGS

FIGURE is a diagram showing activity of CHK1 inhibitor combining with other drugs on MV 4 11 cell line.

DETAILED DESCRIPTION OF THE PREFERRED EMBODIMENT

Preparation Embodiment 1: 5-(1-methyl-1H-pyrazol-4-yl)-$N^2$-(3-methylpyrazol-5-yl)-$N^4$-(piperidin-4-yl)-2,4-diaminopyrimidine (Compound 1)

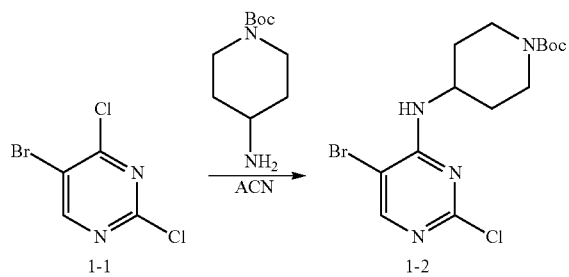

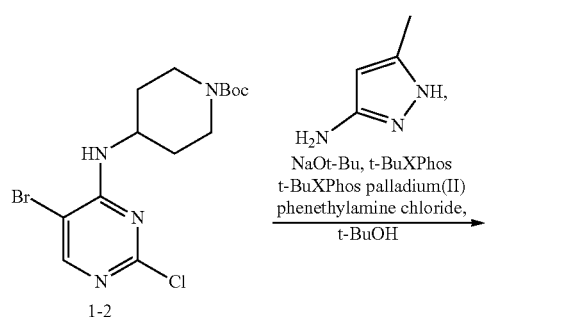

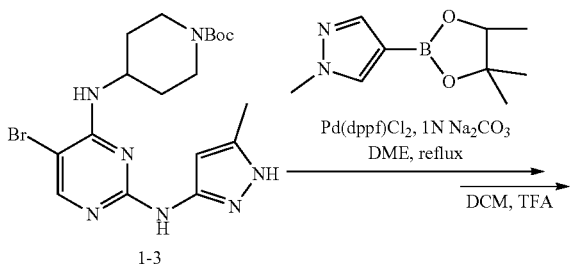

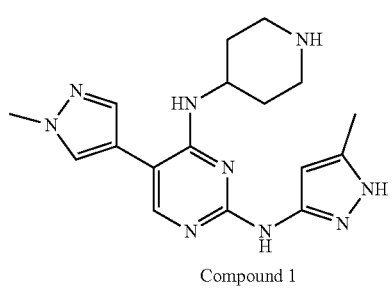

Step 1: Synthesis of 2-chloro-5-bromo-N-(N-tert-butoxycarbonylpiperidin-4-yl)-4-aminopyrimidine (Intermediate 1-2)

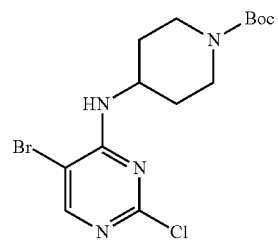 [SMILES: CC(C)(C)OC(=O)N1CCC(Nc2nc(Cl)ncc2Br)CC1]

To a solution of 5-bromo-2,4-dichloropyrimidine (100 mg, 0.44 mmol) in acetonitrile (6 mL), was added an acetonitrile solution (3 mL) of N-tert-butoxycarbonyl-4-aminopiperidine (88 mg, 0.48 mmol), and triethylamine (0.08 mL) dropwise. The reaction mixture was stirred at room temperature for 30 min; then was evaporated under reduced pressure to obtain a white solid. Yield: 82%; mp: 72-74° C.; $^1$H NMR (500 MHz, DMSO-$d_6$): δ 8.26 (s, Ar—H, 1H), 7.38 (d, J=10.0 Hz, NH, 1H), 4.17-4.08 (m, CH, 1H), 3.98-3.95 (m, CH$_2$, 2H), 2.82-2.79 (m, CH$_2$, 2H), 1.76-1.72 (m, CH$_2$, 2H), 1.61-1.51 (m, CH$_2$, 2H), 1.41 (s, CH$_3$×3, 9H); ESI-MS: m/z=391 [M+1]$^+$.

Step 2: Synthesis of 5-bromo-$N^2$-(3-methylpyrazol-5-yl)-$N^4$-(N-tert-butoxycarbonylpiperidin-4-yl)-2,4-diaminopyrimidine (Intermediate 1-3)

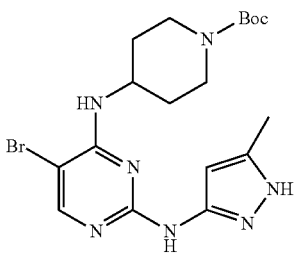 [SMILES: Cc1cc(Nc2ncc(Br)c(NC3CCN(C(=O)OC(C)(C)C)CC3)n2)n[nH]1]

Under nitrogen protection, to a mixture of 3-methyl-5-aminopyrazole (146 mg, 1.5 mmol), chloro(2-dicyclohexylphosphino-2',4',6'-triisopropyl-1,1'-biphenyl)[2-(2-aminoethylphenyl)]palladium(II) (10.3 mg, 0.015 mmol), 2-di-tert-butylphosphino-2',4',6'-triisopropylbiphenyl (6.4 mg, 0.015 mmol) and sodium tert-butoxide (303 mg, 3.15 mmol) was added a solution of the intermediate 1-2 (736 mg, 1.88 mmol) in tert-butanol (5 mL). The reaction mixture was stirred for 4 hrs at room temperature, then filtered. The filtrate was removed by evaporation. A saturated ammonium chloride solution was added and extracted with ethyl acetate. The organic layer was separated, dried over anhydrous sodium sulfate, and evaporated under reduced pressure to remove the solvent. The residue was purified by column chromatography on silica gel with CH$_2$Cl$_2$/EtOH (30:1) as an eluent to give a yellow oil. Yield: 35%; $^1$H NMR (500 MHz, DMSO-$d_6$): δ 11.65 (s, NH, 1H), 8.49 (s, NH, 1H), 7.86 (s, Ar—H, 1H), 7.24 (d, J=8.0 Hz, NH, 1H), 6.29 (s, Ar—H, 1H), 4.15-4.08 (m, CH, 1H), 4.02 (br, CH$_2$, 2H), 2.83 (br, CH$_2$, 2H), 2.31 (s, CH$_3$, 3H), 1.87-1.82 (m, CH$_2$, 2H), 1.60-1.52 (m, CH$_2$, 2H), 1.43 (s, CH$_3$×3, 9H); ESI-MS: m/z=474 [M+1]$^+$.

Step 3: Synthesis of 5-(1-methyl-1H-pyrazol-4-yl)-N$^2$-(3-methylpyrazol-5-yl)-N$^4$-(piperidin-4-yl)-2,4-diaminopyrimidine (Compound 1)

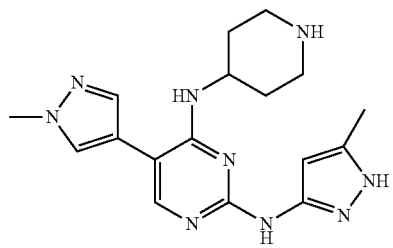 [SMILES: Cc1cc(Nc2ncc(-c3cnn(C)c3)c(NC3CCNCC3)n2)n[nH]1]

Under nitrogen protection, to a mixture of compound 1-3 (647 mg, 1.43 mmol), 1-methyl-1H-pyrazole-4-boronic acid pinacol ester (334 mg, 1.72 mmol), and Pd(dppf)Cl$_2$ (54 mg, 0.07 mmol) was added ethylene glycol dimethyl ether (14 mL) and 1N Na$_2$CO$_3$ (2.8 mL). The reaction mixture was stirred refluxing overnight, then was evaporated under reduced pressure to remove the solvent. The obtained residue was purified by column chromatography on silica gel with CH$_2$Cl$_2$/EtOH (25:1) as an eluent to give a white solid. Removal of the Boc protecting group with trifluoroacetic acid gave a white solid. Yield: 74%; $^1$H NMR (500 MHz, DMSO-d$_6$): δ 11.92 (s, NH, 1H), 10.30 (s, NH, 1H), 8.20 (s, Ar—H, 1H), 7.96 (s, Ar—H, 1H), 7.94 (s, Ar—H, 1H), 6.56 (d, J=7.0 Hz, NH, 1H), 6.29 (s, Ar—H, 1H), 4.15-4.09 (m, CH, 1H), 3.86 (s, CH$_3$, 3H), 3.35 (br, CH$_2$, 2H), 3.05-2.99 (m, CH$_2$, 2H), 2.30 (s, CH$_3$, 3H), 2.06-2.03 (m, CH$_2$, 2H), 1.92-1.86 (m, CH$_2$, 2H); ESI-MS: m/z=452 [M+1]$^+$.

Preparation Embodiment 2: 5-(1-methyl-1H-pyrazol-4-yl)-N$^2$-(5-methyloxazol-3-yl)-N$^4$-(piperidin-4-yl)-2,4-diaminopyrimidine (Compound 2)

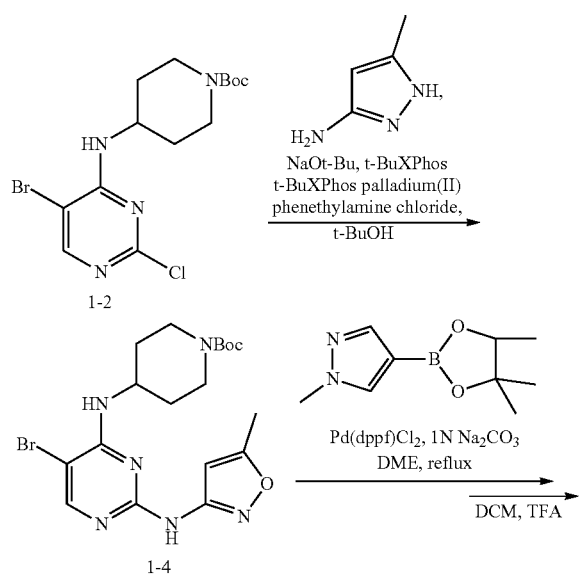

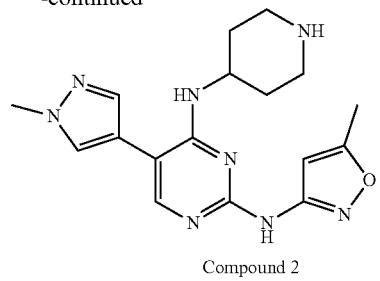

Compound 2

Step 1: Synthesis of 5-bromo-N$^2$-(3-methyloxazol-5-yl)-N$^4$-(N-tert-butoxycarbonylpiperidin-4-yl)-2,4-diaminopyrimidine (Intermediate 1-4)

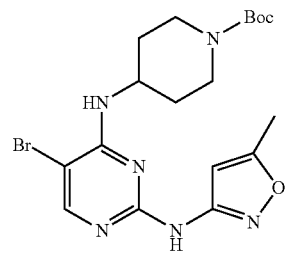 [SMILES: Cc1cc(Nc2ncc(Br)c(NC3CCN(C(=O)OC(C)(C)C)CC3)n2)no1]

wherein a synthetic procedure refers to the step 2 of the preparation embodiment 1; the intermediate 1-4 is synthesized by a synthetic method similar to that of the compound 1-3 with the intermediate 1-2 and 3-methyl-5-aminooxazole as starting materials. Yield: 28%; $^1$H NMR (500 MHz, DMSO-d$_6$): δ 8.48 (s, NH, 1H), 7.85 (s, Ar—H, 1H), 7.28 (d, J=8.0 Hz, NH, 1H), 6.54 (s, Ar—H, 1H), 4.13-4.08 (m, CH, 1H), 4.05 (br, CH$_2$, 2H), 2.83 (br, CH$_2$, 2H), 2.35 (s, CH$_3$, 3H), 1.86-1.80 (m, CH$_2$, 2H), 1.57-1.52 (m, CH$_2$, 2H), 1.42 (s, CH$_3$×3, 9H); ESI-MS: m/z=453 [M+1]$^+$.

Step 2: Synthesis of 5-(1-methyl-1H-pyrazol-4-yl)-N$^2$-(5-methyloxazol-3-yl)-N$^4$-(piperidin-4-yl)-2,4-diaminopyrimidine (Compound 2)

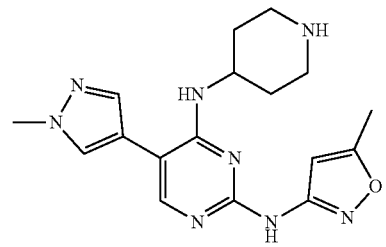 [SMILES: Cc1cc(Nc2ncc(-c3cnn(C)c3)c(NC3CCNCC3)n2)no1]

wherein a synthetic procedure refers to the step 3 of the preparation embodiment 1; the compound 2 is synthesized with the intermediate 1-4 and 1-methyl-1H-pyrazole-4-boronic acid pinacol ester as starting materials. Yield: 83%; $^1$H NMR (500 MHz, DMSO-d$_6$): δ 10.28 (s, NH, 1H), 8.20 (s, Ar—H, 1H), 7.96 (s, Ar—H, 1H), 7.95 (s, Ar—H, 1H), 6.58 (d, J=7.0 Hz, NH, 1H), 6.51 (s, Ar—H, 1H), 4.17-4.10 (m, CH, 1H), 3.92 (s, CH$_3$, 3H), 3.35 (br, CH$_2$, 2H), 3.05-2.98

(m, CH$_2$, 2H), 2.36 (s, CH$_3$, 3H), 2.09-2.07 (m, CH$_2$, 2H), 1.93-1.85 (m, CH$_2$, 2H); ESI-MS: m/z=355 [M+1]$^+$.

Preparation Embodiment 3: 5-(thien-2-yl)-N$^2$-(5-methylpyrazol-3-yl)-N$^4$-(piperidin-4-yl)-2,4-diaminopyrimidine (Compound 3)

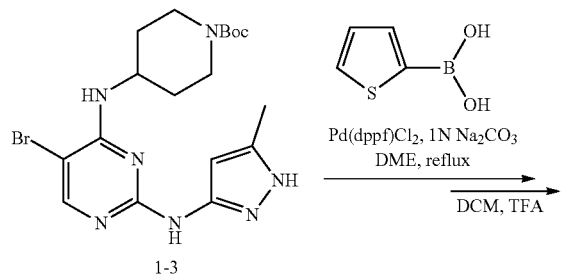

Step 1: Synthesis of 5-(thien-2-yl)-N$^2$-(5-methylpyrazol-3-yl)-N$^4$-(piperidin-4-yl)-2,4-diaminopyrimidine (Compound 3)

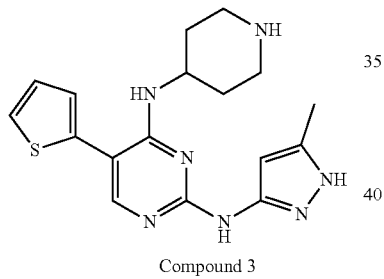

Compound 3 wherein a synthetic procedure refers to the step 3 of the preparation embodiment 1; the compound 3 is synthesized with the intermediate 1-3 and thiophene-2-boronic acid as starting materials. Yield: 83%; LCMS: m/z=356 [M+1]$^+$.

Preparation Embodiment 4: 5-(thien-2-yl)-N$^2$-(5-methyloxazol-3-yl)-N$^4$-(piperidin-4-yl)-2,4-diaminopyrimidine (Compound 4)

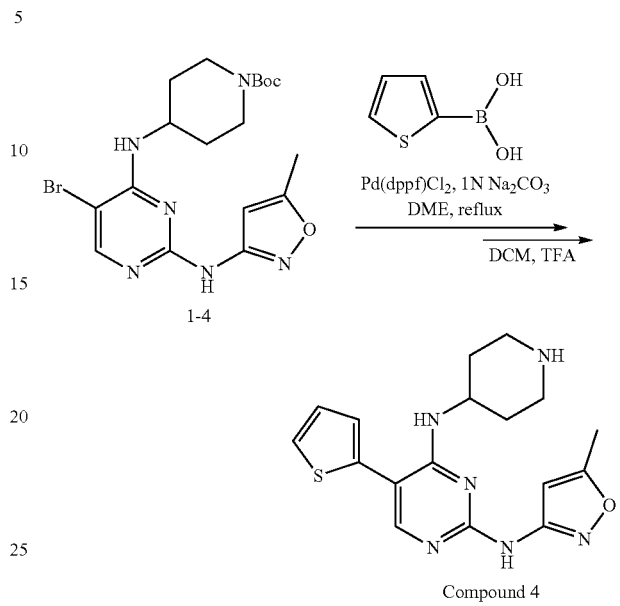

Compound 4

Step 1: Synthesis of 5-(thien-2-yl)-N$^2$-(5-methyloxazol-3-yl)-N$^4$-(piperidin-4-yl)-2,4-diaminopyrimidine (Compound 4)

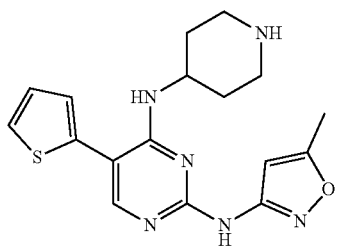 [SMILES: Cc1cc(Nc2ncc(-c3cccs3)c(NC3CCNCC3)n2)no1]

wherein a synthetic procedure refers to the step 3 of the preparation embodiment 1; the compound 4 is synthesized with the intermediates 1-4 and thiophene-2-boronic acid as starting materials. Yield: 83%; LCMS: m/z=357 [M+1]$^+$.

Preparation Embodiment 5: 5-(furan-2-yl)-N$^2$-(5-methylpyrazol-3-yl)-N$^4$-(piperidin-4-yl)-2,4-diaminopyrimidine (Compound 5)

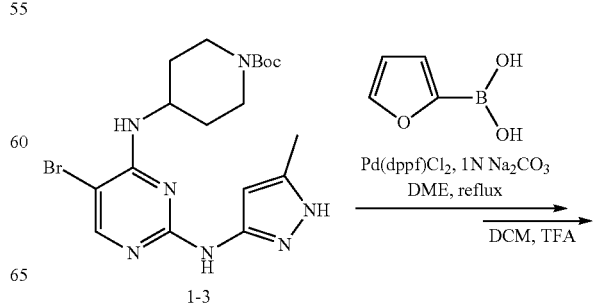

-continued

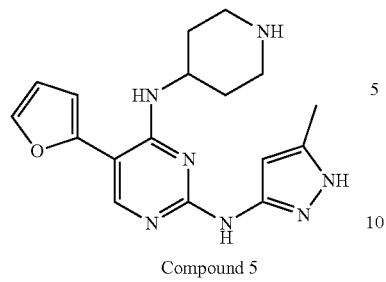

Compound 5

Step 1: Synthesis of 5-(furan-2-yl)-N²-(5-methyl-pyrazol-3-yl)-N⁴-(piperidin-4-yl)-2,4-diaminopyrimidine (Compound 5)

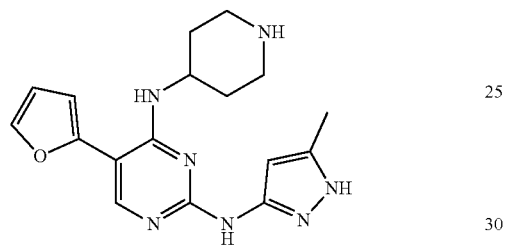

wherein a synthetic procedure refers to the step 3 of the preparation embodiment 1; the compound 5 is synthesized with the intermediates 1-3 and furan-2-boronic acid as starting materials. Yield: 83%; LCMS: m/z=340 [M+1]⁺.

Preparation Embodiment 6: 5-(furan-2-yl)-N²-(5-methyloxazol-3-yl)-N⁴-(piperidin-4-yl)-2,4-diaminopyrimidine (Compound 6)

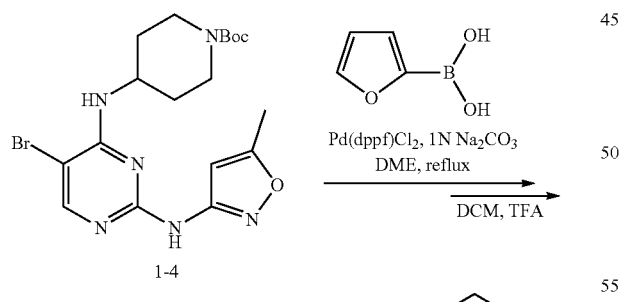

Step 1: Synthesis of 5-(furan-2-yl)-N²-(5-methyloxazol-3-yl)-N⁴-(piperidin-4-yl)-2,4-diaminopyrimidine (Compound 6)

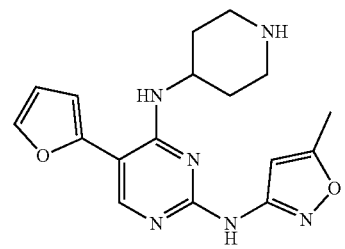 [SMILES: Cc1cc(Nc2ncc(-c3ccco3)c(NC3CCNCC3)n2)no1]

wherein a synthetic procedure refers to the step 3 of the preparation embodiment 1; the compound 5 is synthesized with the intermediates 1-4 and furan-2-boronic acid as starting materials. Yield: 83%; LCMS: m/z=341 [M+1]⁺.

Preparation Embodiment 7: 5-phenyl-N²-(2-cyanopyridin-5-yl)-N⁴-(piperidin-4-methyl)-2,4-diaminopyrimidine (Compound 7)

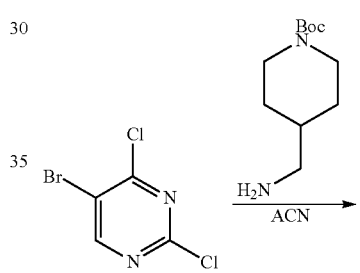

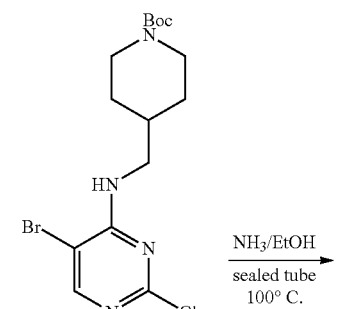

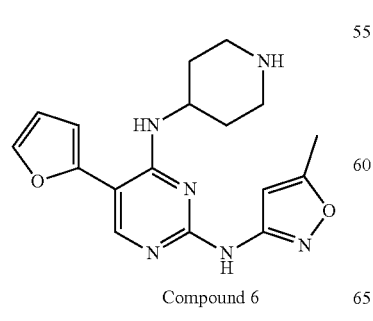

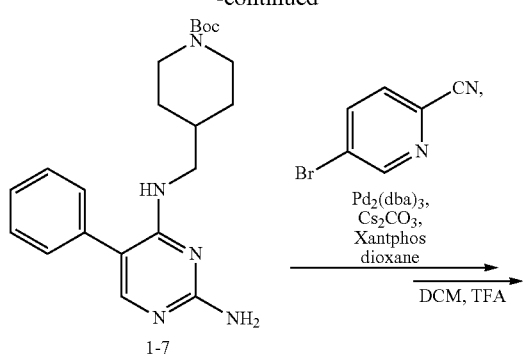

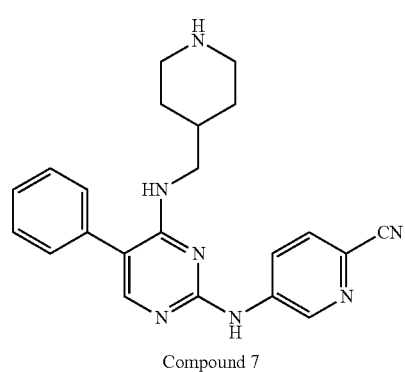

Compound 7

Step 1: Synthesis of 2-chloro-5-bromo-N-(N-tert-butoxycarbonylpiperidin-4-methyl)-4-aminopyrimidine (Intermediate 1-5)

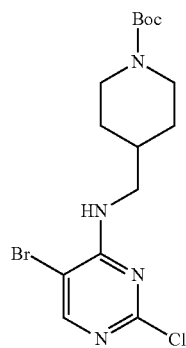 [SMILES: CC(C)(C)OC(=O)N1CCC(CNc2nc(Cl)ncc2Br)CC1]

wherein a synthetic procedure refers to the step 1 of the preparation embodiment 1; the intermediate 1-5 is synthesized by a synthetic method similar to that of the compound 1-2 with the intermediate 1-1 and N-tert-butoxycarbonyl-4-aminomethylpiperidine as starting materials. Yield: 92%; $^1$H NMR (500 MHz, CDCl$_3$): δ 8.12 (s, Ar—H, 1H), 5.64 (t, J=11.0 Hz, NH, 1H), 4.14-4.10 (m, CH$_2$, 2H), 3.46 (t, J 6.0 Hz, CH$_2$, 2H), 2.74 (t, J=11.0 Hz, CH$_2$, 2H), 1.85-1.76 (m, CH, 1H), 1.73-1.71 (m, CH$_2$, 2H), 1.46 (s, CH$_3$×3, 9H), 1.25-1.16 (m, CH$_2$, 2H); ESI-MS: m/z=405 [M+1]$^+$.

Step 2: Synthesis of 5-bromo-N$^4$-(N-tert-butoxycarbonylpiperidin-4-methyl)-2,4-diaminopyrimidine (Intermediate 1-6)

To intermediate 1-5 (500 mg, 1.23 mmol) in a sealed tube was added an ammonia-saturated ethanol solution (20 mL), and was stirred at 100° C. for 24 h; then cooled to room temperature, the mixture was evaporated under reduced pressure to remove the solvent. The residue was purified by column chromatography on silica gel with PE:EtOAc (2:1) as an eluent to obtain a white solid. Yield: 85%; $^1$H NMR (500 MHz, CDCl$_3$): δ 7.87 (s, Ar—H, 1H), 5.27 (t, J=11.0 Hz, NH, 1H), 4.81 (br, NH$_2$, 2H), 4.13 (br, CH$_2$, 2H), 3.35-3.33 (m, CH$_2$, 2H), 2.70 (br, CH$_2$, 2H), 1.78-1.74 (m, CH, 1H), 1.72-1.69 (m, CH$_2$, 2H), 1.46 (s, CH$_3$×3, 9H), 1.20-1.14 (m, CH$_2$, 2H); ESI-MS: m/z=386 [M+1]$^+$.

Step 3: Synthesis of 5-phenyl-N$^4$-(N-tert-butoxycarbonylpiperidin-4-methyl)-2,4-diaminopyrimidine (Intermediate 1-7)

wherein a synthetic procedure refers to the step 3 of the preparation embodiment 1; the intermediate 1-7 is synthesized with the intermediate 1-6 and phenylboronic acid as starting materials. Yield: 84%; $^1$H NMR (500 MHz, CDCl$_3$): δ 8.09 (s, Ar—H, 1H), 7.52 (s, Ar—H, 2H), 7.51 (s, Ar—H, 2H), 7.40 (s, Ar—H, 1H), 5.51 (t, J=5.5 Hz, NH, 1H), 4.91 (br, NH$_2$, 2H), 4.08 (br, CH$_2$, 2H), 3.21 (t, J=6.0 Hz, CH$_2$, 2H), 2.57 (br, CH$_2$, 2H), 1.67-1.59 (m, CH, 1H), 1.63-1.60 (m, CH$_2$, 2H), 1.39 (s, CH$_3$×3, 9H), 1.10-1.02 (m, CH$_2$, 2H); ESI-MS: m/z=384 [M+1]$^+$.

Step 4: Synthesis of 5-phenyl-N²-(2-cyanopyridin-5-yl)-N⁴-(piperidin-4-methyl)-2,4-diaminopyrimidine (Compound 7)

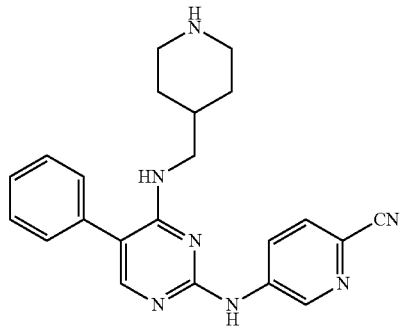 [SMILES: N#Cc1ccc(Nc2ncc(-c3ccccc3)c(NCC3CCNCC3)n2)cn1]

Under nitrogen protection, anhydrous dioxane (6 mL) was added to a mixture of the intermediate 1-7 (378 mg, 0.986 mmol), 5-bromo-2-cyanopyridine (180 mg, 0.986 mmol), tris(dibenzylideneacetone)dipalladium (9 mg, 0.00986 mmol), 4,5-bisdiphenylphosphino-9,9-dimethyloxaxan (15 mg, 0.026 mmol), and cesium carbonate (450 mg, 1.38 mmol). The reaction was stirred refluxing overnight. After cooling to room temperature, then was filtered. The filtrate was removed by evaporation. The obtained residue was purified by column chromatography on silica gel with $CH_2Cl_2$/EtOH (30:1) as an eluent to give a white solid. Deprotecting a Boc protective group with trifluoroacetic acid to obtain a white solid. Yield: 67%; mp: 239-241° C.; $^1$H NMR (500 MHz, DMSO-$d_6$): δ 9.97 (br, NH, 1H), 9.08 (d, J=2.5 Hz, Ar—H, 1H), 8.50 (dd, J=9.0 Hz, 3.0 Hz, Ar—H, 1H), 7.92 (d, J=8.5 Hz, Ar—H, 1H), 7.82 (s, Ar—H, 1H), 7.50-7.47 (m, Ar—H, 2H), 7.41-7.38 (m, Ar—H, 3H), 6.82 (t, J=6.0 Hz, NH, 1H), 3.29 (t, J=6.5 Hz, $CH_2$, 2H), 3.10 (d, J=12.5 Hz, $CH_2$, 2H), 2.61-2.56 (m, $CH_2$, 2H), 1.93-1.84 (m, CH, 1H), 1.72 (d, J=11.5 Hz, $CH_2$, 2H), 1.22-1.16 (m, $CH_2$, 2H); ESI-MS: m/z=386 [M+1]⁺.

Preparation Embodiment 8: 5-(3-fluorophenyl)-N²-(2-cyanopyridin-5-yl)-N⁴-(piperidin-4-methyl)-2,4-diaminopyrimidine (Compound 8)

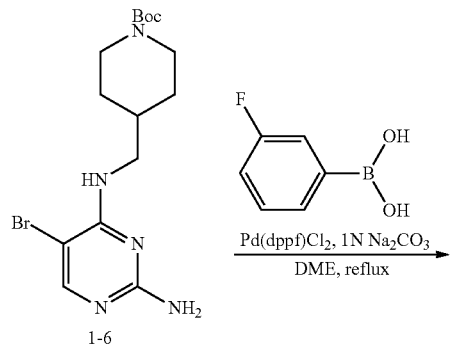

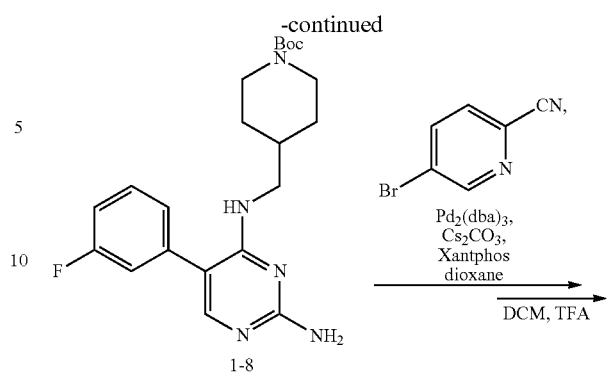

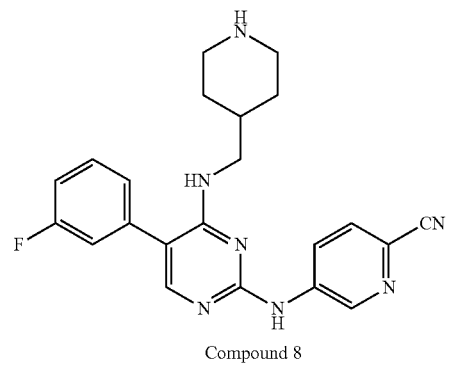

Compound 8

Step 1: Synthesis of 5-(3-fluorophenyl)-N⁴-(N-tert-butoxycarbonylpiperidin-4-methyl)-2,4-diaminopyrimidine (Intermediate 1-8)

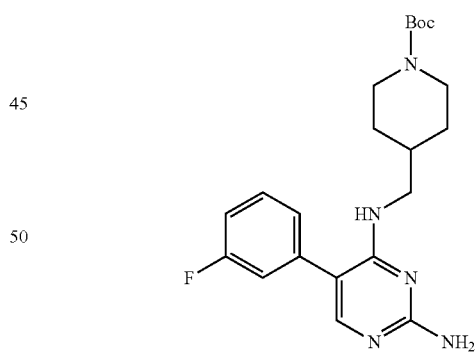

wherein a synthetic procedure refers to the step 3 of the preparation embodiment 1; the intermediate 1-8 is synthesized with the intermediate 1-6 and 3-fluorophenylboronic acid as starting materials. Yield: 87%; $^1$H NMR (500 MHz, $CDCl_3$): δ 8.14 (s, Ar—H, 1H), 7.48-7.45 (m, Ar—H, 2H), 7.26-7.23 (m, Ar—H, 1H), 7.18-7.16 (m, Ar—H, 1H), 5.59 (t, J=5.5 Hz, NH, 1H), 4.96 (br, $NH_2$, 2H), 4.15 (br, $CH_2$, 2H), 3.26 (t, J=6.0 Hz, $CH_2$, 2H), 2.59 (br, $CH_2$, 2H), 1.71-1.65 (m, CH, 1H), 1.73-1.70 (m, $CH_2$, 2H), 1.43 (s, $CH_3\times3$, 9H), 1.19-1.05 (m, $CH_2$, 2H); ESI-MS: m/z=402 [M+1]⁺.

Step 2: Synthesis of 5-(3-fluorophenyl)-$N^2$-(2-cyanopyridin-5-yl)-$N^4$-(piperidin-4-methyl)-2,4-diaminopyrimidine (Compound 8)

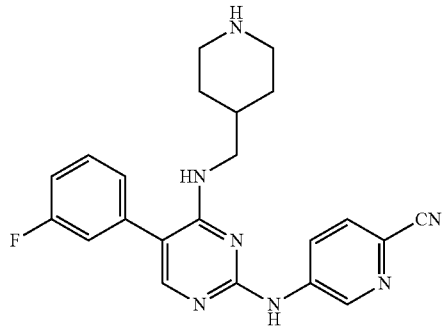 [SMILES: N#Cc1ccc(Nc2ncc(-c3cccc(F)c3)c(NCC3CCNCC3)n2)cn1]

wherein a synthetic procedure refers to the step 4 of the preparation embodiment 7; the compound 8 is synthesized with the intermediate 1-8 and 5-bromo-2-cyanopyridine as starting materials, so as to obtain a white solid. Yield: 65%; mp: 206-208° C.; $^1$H NMR (500 MHz, DMSO-$d_6$): δ 10.00 (br, NH, 1H), 9.08 (d, J=2.5 Hz, Ar—H, 1H), 8.49 (dd, J=8.5 Hz, 2.5 Hz, Ar—H, 1H), 7.93 (d, J=8.5 Hz, Ar—H, 1H), 7.86 (s, Ar—H, 1H), 7.54-7.50 (m, Ar—H, 1H), 7.24-7.20 (m, Ar—H, 3H), 6.97 (t, J=5.5 Hz, NH, 1H), 3.29 (t, J=6.5 Hz, $CH_2$, 2H), 3.09 (d, J=12.5 Hz, $CH_2$, 2H), 2.60-2.56 (m, $CH_2$, 2H), 1.94-1.85 (m, CH, 1H), 1.72 (d, J=12.5 Hz, $CH_2$, 2H), 1.22-1.17 (m, $CH_2$, 2H); ESI-MS: m/z=404 $[M+1]^+$.

Preparation Embodiment 9: 5-(1-methyl-1H-pyrazol-4-yl)-$N^2$-(2-cyanopyridin-5-yl)-$N^4$-(piperidin-4-methyl)-2,4-diaminopyrimidine (Compound 9)

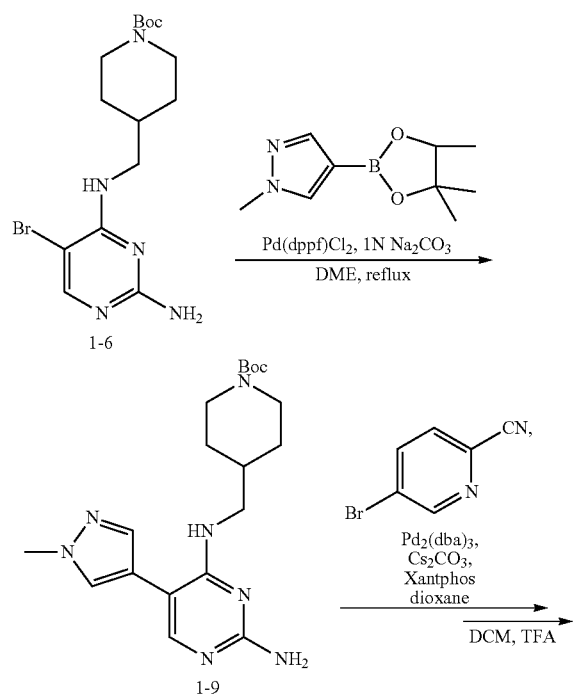

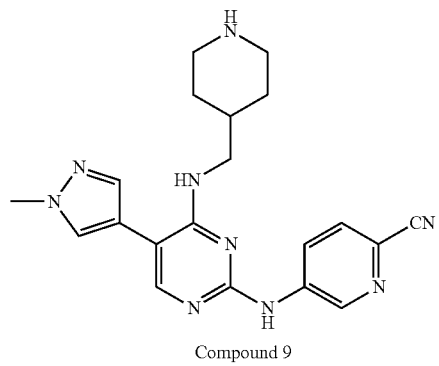

Compound 9

Step 1: Synthesis of 5-(1-methyl-1H-pyrazol-4-yl)-$N^4$-(N-tert-butoxycarbonylpiperidin-4-methyl)-2,4-diaminopyrimidine (Intermediate 1-9)

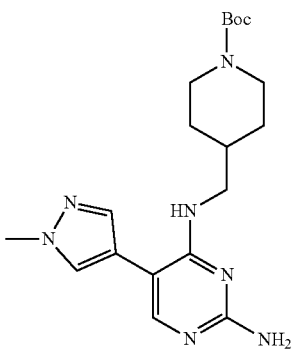 [SMILES: Cn1cc(-c2cnc(N)nc2NCC2CCN(C(=O)OC(C)(C)C)CC2)cn1]

wherein a synthetic procedure refers to the step 3 of the preparation embodiment 1; the intermediate 1-9 is synthesized with the intermediate 1-6 and 1-methyl-1H-pyrazol-4-boronic acid pinacol ester as starting materials. Yield: 70%; mp: 174-176° C.; $^1$H NMR (500 MHz, CDCl$_3$): δ 7.67 (s, Ar—H, 1H), 7.50 (s, Ar—H, 1H), 7.38 (s, Ar—H, 1H), 5.01 (t, J=5.5 Hz, NH, 1H), 4.81 (br, $NH_2$, 2H), 4.10 (br, $CH_2$, 2H), 3.96 (s, $CH_3$, 3H), 3.31 (t, J=6.0 Hz, $CH_2$, 2H), 2.68 (br, $CH_2$, 2H), 1.76-1.69 (m, CH, 1H), 1.67-1.64 (m, $CH_2$, 2H), 1.45 (s, $CH_3$×3, 9H), 1.17-1.09 (m, $CH_2$, 2H); ESI-MS: m/z=388 $[M+1]^+$.

Step 2: Synthesis of 5-(1-methyl-1H-pyrazol-4-yl)-N²-(2-cyanopyridin-5-yl)-N⁴-(piperidin-4-methyl)-2,4-diaminopyrimidine (Compound 9)

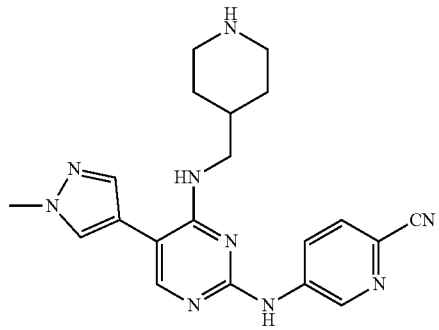 [SMILES: Cn1cc(-c2cnc(Nc3ccc(C#N)nc3)nc2NCC2CCNCC2)cn1]

wherein a synthetic procedure refers to the step 4 of the preparation embodiment 7; the compound 9 is synthesized with the intermediate 1-9 and 5-bromo-2-cyanopyridine as starting materials, so as to obtain a white solid. Yield: 69%; mp: 231-233° C.; ¹H NMR (500 MHz, DMSO-d₆): δ 9.94 (s, NH, 1H), 9.04 (d, J=2.5 Hz, Ar—H, 1H), 8.48 (dd, J=8.5 Hz, 2.5 Hz, Ar—H, 1H), 7.93-7.92 (m, Ar—H, 2H), 7.90 (s, Ar—H, 1H), 7.61 (s, Ar—H, 1H), 6.83 (t, J=6.0 Hz, NH, 1H), 3.89 (s, CH₃, 3H), 3.40-3.37 (m, CH₂, 2H), 3.26 (d, J=12.5 Hz, CH₂, 2H), 2.81-2.76 (m, CH₂, 2H), 2.01-1.96 (m, CH, 1H), 1.83 (d, J=12.5 Hz, CH₂, 2H), 1.45-1.36 (m, CH₂, 2H); ESI-MS: m/z=390 [M+1]⁺.

Preparation Embodiment 10: 5-(3-fluorophenyl)-N²-(2-cyanopyridin-5-yl)-N⁴-aminoethyl-2,4-diaminopyrimidine (Compound 10)

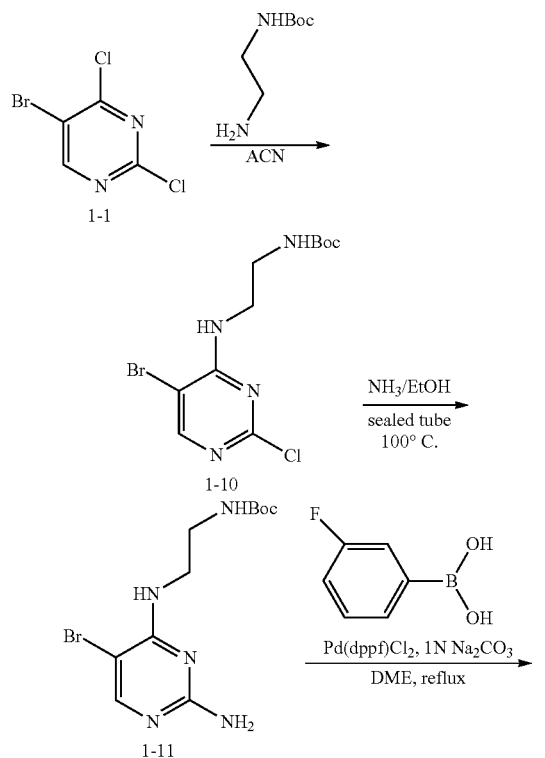

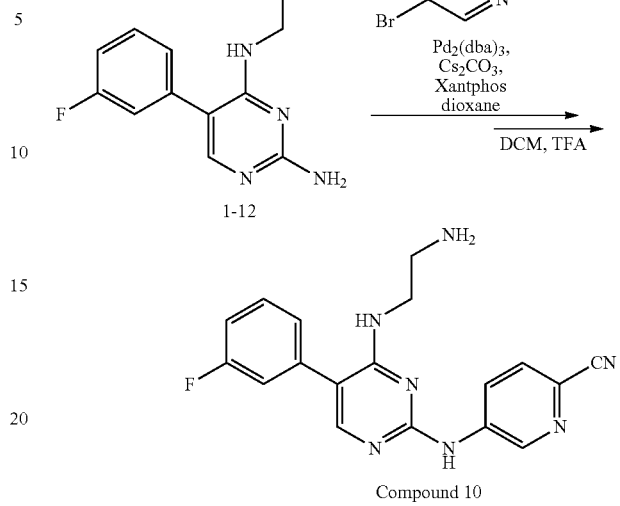

Compound 10

Step 1: Synthesis of 2-chloro-5-bromo-N-(N-tert-butoxycarbonylaminoethyl)-4-aminopyrimidine (Intermediate 1-10)

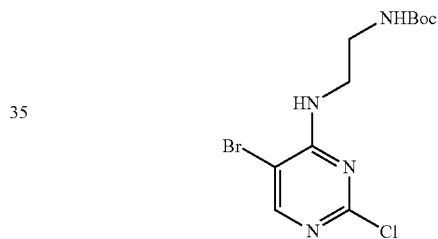

wherein a synthetic procedure refers to the step 1 of the preparation embodiment 1; the intermediate 1-10 is synthesized by a synthetic method similar to that of the compound 1-2 with the intermediate 1-1 and N-tert-butoxycarbonyl-1,2-ethanediamine as starting materials. Yield: 94%; mp: 115-117° C.; ¹H NMR (500 MHz, DMSO-d₆): δ 8.24 (s, Ar—H, 1H), 7.68 (t, J=5.0 Hz, NH, 1H), 6.96 (t, J=5.5 Hz, NH, 1H), 3.42-3.38 (m, CH₂, 2H), 3.16-3.13 (m, CH₂, 2H), 1.37 (s, CH₃×3, 9H); ESI-MS: m/z=351 [M+1]⁺.

Step 2: Synthesis of 5-bromo-N⁴-(N-tert-butoxycarbonylaminoethyl)-2,4-diaminopyrimidine (Intermediate 1-11)

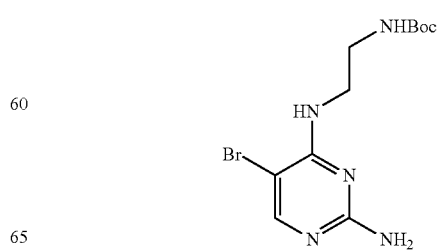

wherein a synthetic procedure refers to the step 2 of the preparation embodiment 7; the intermediate 1-11 is synthesized by a synthetic method similar to that of the compound 1-6. Yield: 81%; mp: 117-119° C.; $^1$H NMR (500 MHz, CDCl$_3$): δ 7.78 (s, Ar—H, 1H), 6.94 (t, J=5.5 Hz, NH, 1H), 6.57 (t, J=5.5 Hz, NH, 1H), 6.22 (s, NH$_2$, 2H), 3.37 (dd, J=11.5 Hz, 6.0 Hz, CH$_2$, 2H), 3.14 (dd, J=12.0 Hz, 6.0 Hz, CH$_2$, 2H), 1.38 (s, CH$_3$×3, 9H); ESI-MS: m/z=332 [M+1]$^+$.

Step 3: Synthesis of 5-(3-fluorophenyl)-N$^4$-(N-tert-butoxycarbonylaminoethyl)-2,4-diaminopyrimidine (Intermediate 1-12)

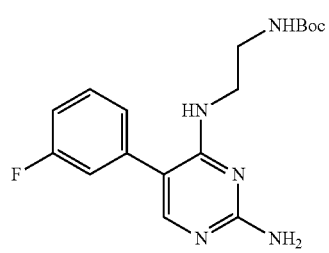 [SMILES: CC(C)(C)OC(=O)NCCNc1nc(N)ncc1-c1cccc(F)c1]

wherein a synthetic procedure refers to the step 3 of the preparation embodiment 1; the intermediate 1-12 is synthesized with the intermediate 1-11 and 3-fluorophenylboronic acid as starting materials. Yield: 78%; $^1$H NMR (500 MHz, DMSO-d$_6$): δ 7.60-7.57 (m, Ar—H, 1H), 7.46 (dd, J=14.5 Hz, 7.5 Hz, Ar—H, 1H), 7.17 (s, Ar—H, 1H), 7.16 (s, Ar—H, 1H), 7.15-7.11 (m, Ar—H, 1H), 6.86 (t, J=5.0 Hz, NH, 1H), 6.29 (t, J=5.0 Hz, NH, 1H), 6.12 (br, NH$_2$, 2H), 3.36-3.34 (m, CH$_2$, 2H), 3.13-3.10 (m, CH$_2$, 2H), 1.34 (s, CH$_3$×3, 9H); ESI-MS: m/z=348 [M+1]$^+$.

Step 4: Synthesis of 5-(3-fluorophenyl)-N$^2$-(2-cyanopyridin-5-yl)-N$^4$-aminoethyl-2,4-diaminopyrimidine (Compound 10)

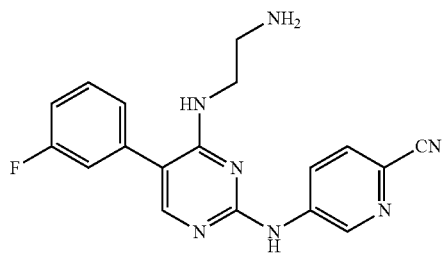 [SMILES: N#Cc1ccc(Nc2ncc(-c3cccc(F)c3)c(NCCN)n2)cn1]

wherein a synthetic procedure refers to the step 4 of the preparation embodiment 7; the compound 10 is synthesized with the intermediate 1-12 and 5-bromo-2-cyanopyridine as starting materials, so as to obtain a white solid. Yield: 68%; mp: 148-150° C.; $^1$H NMR (500 MHz, DMSO-d$_6$): δ 10.02 (br, NH, 1H), 9.06 (d, J=2.0 Hz, Ar—H, 1H), 8.52 (dd, J=9.0 Hz, 2.5 Hz, Ar—H, 1H), 7.93 (d, J=8.5 Hz, Ar—H, 1H), 7.88 (s, Ar—H, 1H), 7.54-7.49 (m, Ar—H, 1H), 7.30-7.25 (m, Ar—H, 2H), 7.24-7.20 (m, Ar—H, 1H), 6.81 (t, J=4.0 Hz, NH, 1H), 3.41-3.38 (m, CH$_2$, 2H), 2.77 (t, J=6.5 Hz, CH$_2$, 2H); ESI-MS: m/z=350 [M+1]$^+$.

Preparation Embodiment 11: 5-(1-methyl-1H-pyrazol-4-yl)-N$^2$-(2-cyanopyridin-5-yl)-N$^4$-aminoethyl-2,4-diaminopyrimidine (Compound 11)

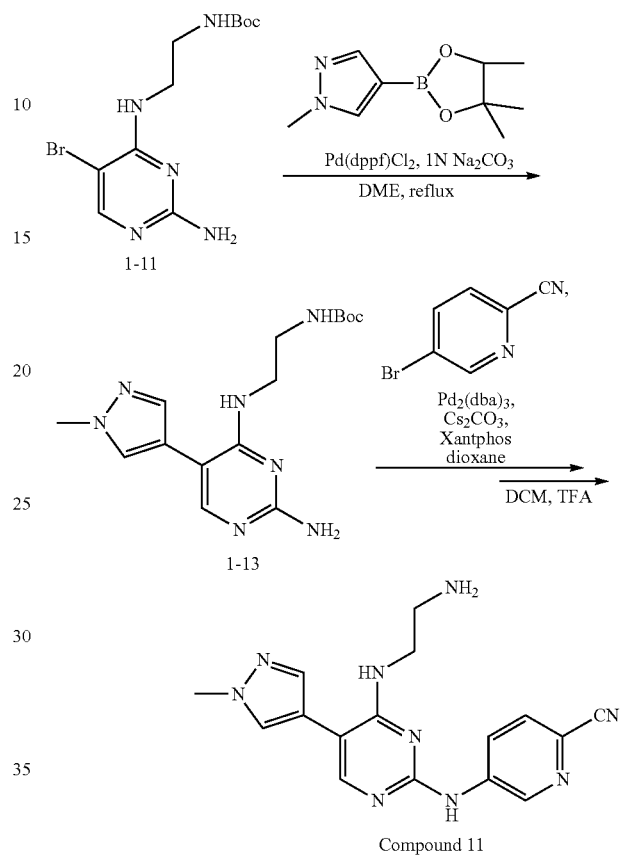

Step 1: Synthesis of 5-(1-methyl-1H-pyrazol-4-yl)-N$^4$-(N-tert-butoxycarbonylaminoethyl)-2,4-diaminopyrimidine (Intermediate 1-13)

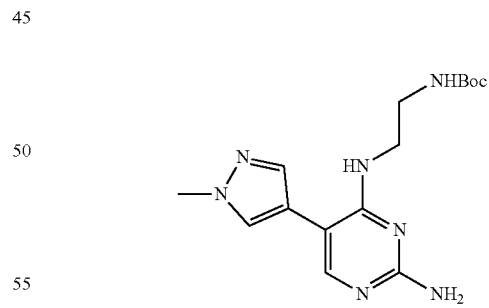

wherein a synthetic procedure refers to the step 3 of the preparation embodiment 1; the intermediate 1-13 is synthesized with the intermediate 1-11 and 1-methyl-1H-pyrazole-4-boronic acid pinacol ester as starting materials. Yield: 80%; mp: 52-54° C.; $^1$H NMR (500 MHz, DMSO-d$_6$): δ 7.78 (s, Ar—H, 1H), 7.60 (s, Ar—H, 1H), 7.50 (s, Ar—H, 1H), 6.92 (t, J=4.5 Hz, NH, 1H), 6.05 (t, J=4.5 Hz, NH, 1H), 5.97 (s, NH$_2$, 2H), 3.85 (s, CH$_3$, 3H), 3.36-3.35 (m, CH$_2$, 2H), 3.13 (dd, J=11.0 Hz, 5.5 Hz, CH$_2$, 2H), 1.35 (s, CH$_3$×3, 9H); ESI-MS: m/z=334 [M+1]$^+$.

Step 2: Synthesis of 5-(1-methyl-1H-pyrazol-4-yl)-N²-(2-cyanopyridin-5-yl)-N⁴-aminoethyl-2,4-diaminopyrimidine (Compound 11)

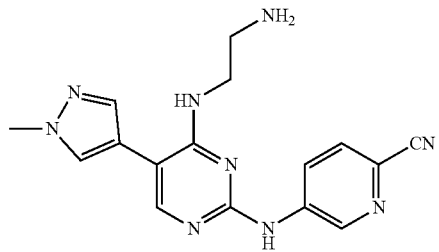 [SMILES: Cn1cc(-c2cnc(Nc3ccc(C#N)nc3)nc2NCCN)cn1]

wherein a synthetic procedure refers to the step 4 of the preparation embodiment 7; the compound 11 is synthesized with the intermediate 1-13 and 5-bromo-2-cyanopyridine as starting materials, so as to obtain a white solid. Yield: 64%; mp: 189-191° C. $^1$H NMR (500 MHz, DMSO-d$_6$) δ 9.91 (s, NH, 1H), 9.05 (d, J=2.5 Hz, Ar—H, 1H), 8.48 (dd, J=8.5 Hz, 2.5 Hz, Ar—H, 1H), 7.93 (s, Ar—H, 1H), 7.91 (s, Ar—H, 1H), 7.87 (d, J=8.5 Hz, Ar—H, 1H), 7.63 (s, Ar—H, 1H), 6.57 (t, J=5.5 Hz, NH, 1H), 3.90 (s, CH$_3$, 3H), 3.58 (t, J=4.5 Hz, CH$_2$×2, 4H), 3.54-3.50 (m, CH$_2$, 2H), 2.55 (t, J=7.0 Hz, CH$_2$, 2H), 2.42 (br, CH$_2$×2, 4H); $^{13}$C NMR (125 MHz, DMSO-d$_6$, ppm) δ 159.51, 157.62, 153.20, 141.26, 137.42, 129.18, 129.10, 123.40, 122.38, 118.35, 113.92, 104.46, 66.33, 56.34, 53.07, 38.67, 37.37. ESI-MS: m/z=406 [M+1]⁺.

Preparation Embodiment 12: 5-(1-methyl-1H-pyrazol-4-yl)-N²-(2-cyanopyridin-5-yl)-N⁴-(piperidin-4-methyl)-2,4-diaminopyrimidine (Compound 12)

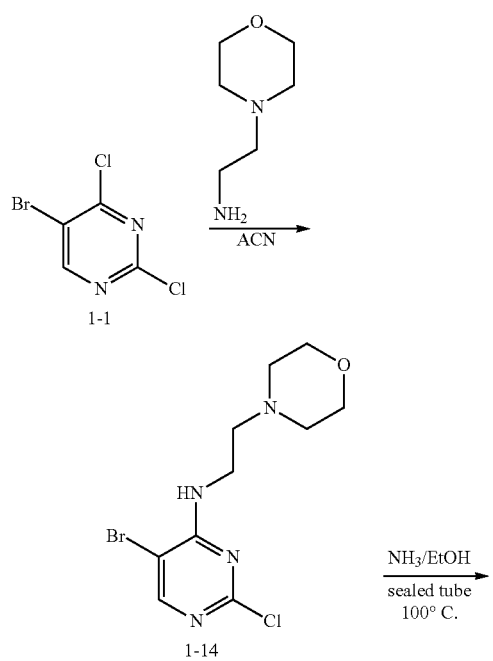

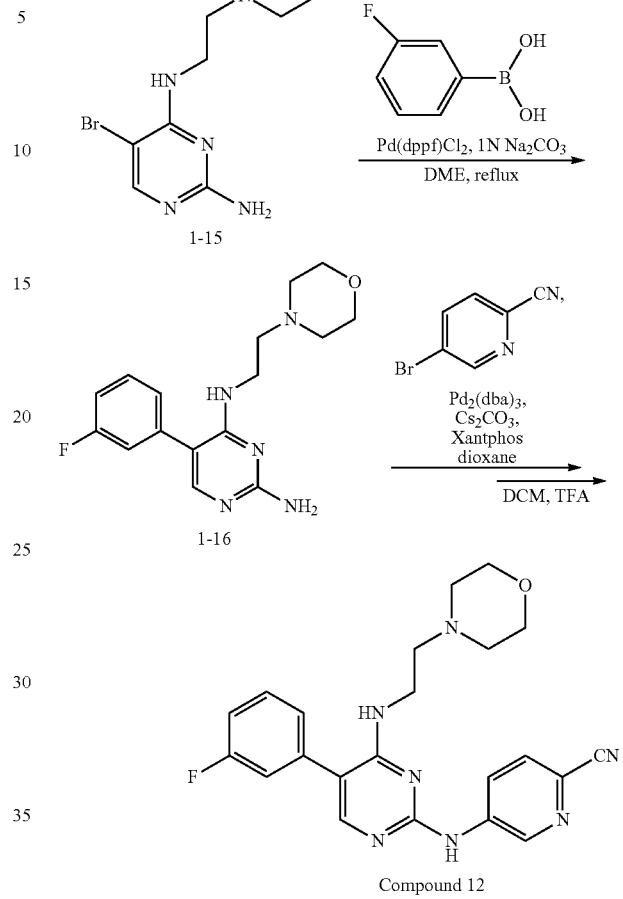

Step 1: Synthesis of 2-chloro-5-bromo-N-(2-morpholinethyl)-4-aminopyrimidine (Intermediate 1-14)

wherein a synthetic procedure refers to the step 1 of the preparation embodiment 1; the intermediate 1-14 is synthesized by a synthetic method similar to that of the compound 1-2 with the intermediate 1-1 and 2-morpholinethylamine as starting materials. Yield: 95%; $^1$H NMR (500 MHz, CDCl$_3$): δ 8.12 (s, Ar—H, 1H), 6.46 (br, NH, 1H), 3.76 (br, CH$_2$×2, 4H), 3.58 (br, CH$_2$, 2H), 2.66 (br, CH$_2$, 2H), 2.55 (br, CH$_2$×2, 4H); ESI-MS: m/z=321 [M+1]⁺.

Step 2: Synthesis of 5-bromo-N⁴-(2-morpholinethyl)-2,4-diaminopyrimidine (Intermediate 1-15)

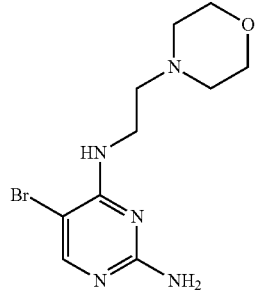 [SMILES: Nc1ncc(Br)c(NCCN2CCOCC2)n1]

wherein a synthetic procedure refers to the step 2 of the preparation embodiment 7; the intermediate 1-15 is synthesized by a synthetic method similar to that of the compound 1-6. Yield: 78%; ¹H NMR (500 MHz, CDCl₃): δ 7.87 (s, Ar—H, 1H), 5.96 (br, NH, 1H), 4.79 (br, NH₂, 2H), 3.75 (t, J=4.5 Hz, CH₂×2, 4H), 3.50 (dd, J=11.0 Hz, 6.0 Hz, CH₂, 2H), 2.62 (t, J=6.0 Hz, CH₂, 2H), 2.52-2.51 (m, CH₂×2, 4H); ESI-MS: m/z=302 [M+1]⁺.

Step 3: Synthesis of 5-(3-fluorophenyl)-N⁴-(2-morpholinethyl)-2,4-diaminopyrimidine (Intermediate 1-16)

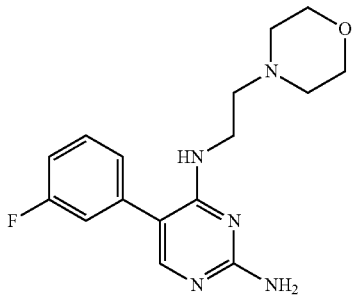 [SMILES: Nc1ncc(-c2cccc(F)c2)c(NCCN2CCOCC2)n1]

wherein a synthetic procedure refers to the step 3 of the preparation embodiment 1; the intermediate 1-16 is synthesized with the intermediate 1-15 and 3-fluorophenylboronic acid as starting materials. Yield: 79%; ¹H NMR (500 MHz, CDCl₃) δ 7.58-7.55 (m, Ar—H, 1H), 7.44-7.40 (m, Ar—H, 1H), 7.15 (s, Ar—H, 1H), 7.13 (s, Ar—H, 1H), 7.11-7.09 (m, Ar—H, 1H), 5.71 (br, NH, 1H), 4.88 (s, NH₂, 2H), 3.63 (t, J=4.0 Hz, CH₂×2, 4H), 3.47 (dd, J=11.0 Hz, 6.0 Hz, CH₂, 2H), 2.55 (t, J=6.0 Hz, CH₂, 2H), 2.42 (br, CH₂×2, 4H); ESI-MS: m/z=318 [M+1]⁺.

Step 4: Synthesis of 5-(3-fluorophenyl)-N²-(2-cyanopyridin-5-yl)-N⁴-(2-morpholinethyl)-2,4-diaminopyrimidine (Compound 12)

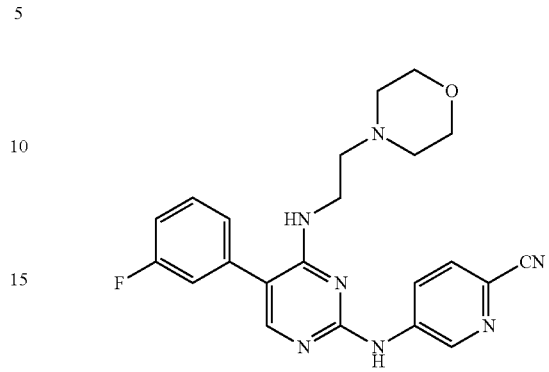

wherein a synthetic procedure refers to the step 4 of the preparation embodiment 7; the compound 12 is synthesized with the intermediate 1-16 and 5-bromo-2-cyanopyridine as starting materials, so as to obtain a white solid. Yield: 81%; mp: 188-190° C.; ¹H NMR (500 MHz, DMSO-d₆): δ 10.01 (br, NH, 1H), 9.08 (d, J=2.5 Hz, Ar—H, 1H), 8.50 (dd, J=9.0 Hz, 2.5 Hz, Ar—H, 1H), 7.91 (s, Ar—H, 1H), 7.90 (d, J=8.5 Hz, Ar—H, 1H), 7.56-7.52 (m, Ar—H, 1H), 7.32-7.29 (m, Ar—H, 1H), 7.29 (d, J=7.5 Hz, Ar—H, 1H), 7.26-7.22 (m, Ar—H, 1H), 6.69 (t, J=5.0 Hz, NH, 1H), 3.55 (t, J=4.0 Hz, CH₂×2, 4H), 3.53-3.49 (m, CH₂, 2H), 2.54-2.51 (m, CH₂, 2H), 2.40 (br, CH₂×2, 4H); ESI-MS: m/z=420 [M+1]⁺.

Preparation Embodiment 13: 5-(1-methyl-1H-pyrazol-4-yl)-N²-(2-cyanopyridin-5-yl)-N⁴-aminoethyl-2,4-diaminopyrimidine (Compound 13)

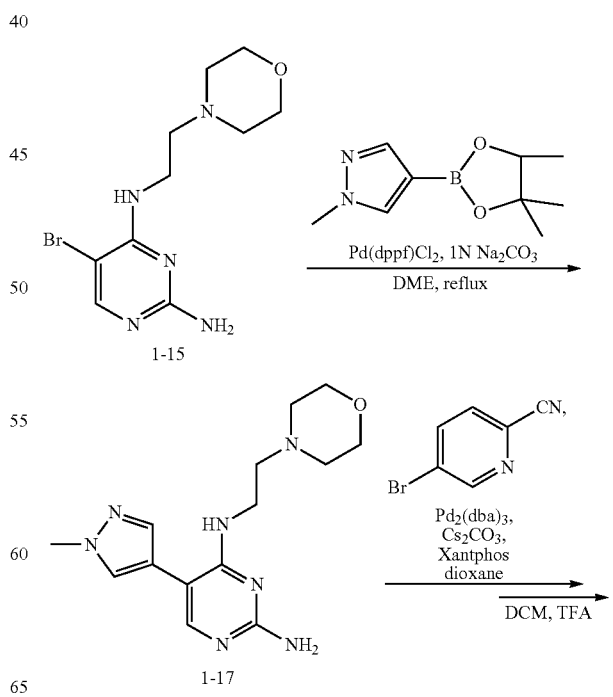

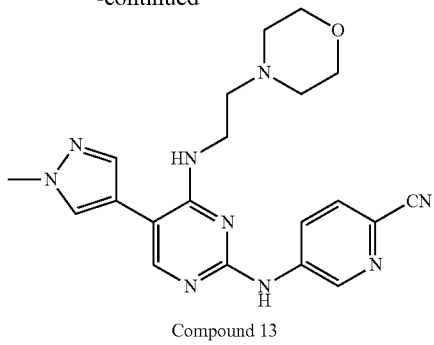

Compound 13

Step 1: Synthesis of 5-(1-methyl-1H-pyrazol-4-yl)-N⁴-(2-morpholinethyl)-2,4-diaminopyrimidine (Intermediate 1-17)

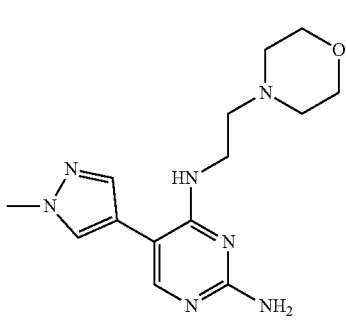 [SMILES: Cn1cc(-c2cnc(N)nc2NCCN2CCOCC2)cn1]

wherein a synthetic procedure refers to the step 3 of the preparation embodiment 1; the intermediate 1-17 is synthesized with the intermediate 1-15 and 1-methyl-1H-pyrazol-4-boronic acid pinacol ester as starting materials. Yield: 76%; ¹H NMR (500 MHz, CDCl₃): δ 7.70 (s, Ar—H, 1H), 7.56 (s, Ar—H, 1H), 7.42 (s, Ar—H, 1H), 5.75 (br, NH, 1H), 4.91 (s, NH₂, 2H), 3.97 (s, CH₃, 3H), 3.68 (t, J=4.0 Hz, CH₂×2, 4H), 3.49 (dd, J=11.0 Hz, 6.0 Hz, CH₂, 2H), 2.57 (t, J=6.0 Hz, CH₂, 2H), 2.46 (br, CH₂×2, 4H); ESI-MS: m/z=304 [M+1]⁺.

Step 2: Synthesis of 5-(1-methyl-1H-pyrazol-4-yl)-N²-(2-cyanopyridin-5-yl)-N⁴-aminoethyl-2,4-diaminopyrimidine (Compound 13)

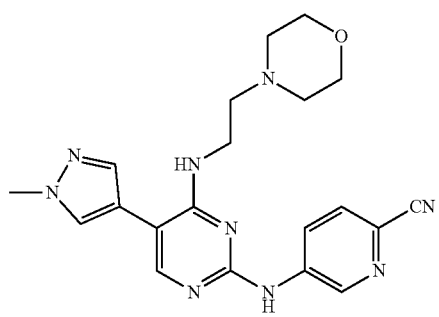

wherein a synthetic procedure refers to the step 4 of the preparation embodiment 7; the compound 13 is synthesized with the intermediate 1-17 and 5-bromo-2-cyanopyridine as starting materials, so as to obtain a white solid. Yield: 84%; mp: 189-191° C.; ¹H NMR (500 MHz, DMSO-d): δ 9.91 (s, NH, 1H), 9.05 (d, J=2.5 Hz, Ar—H, 1H), 8.48 (dd, J=8.5 Hz, 2.5 Hz, Ar—H, 1H), 7.93 (s, Ar—H, 1H), 7.91 (s, Ar—H, 1H), 7.87 (d, J=8.5 Hz, Ar—H, 1H), 7.63 (s, Ar—H, 1H), 6.57 (t, J=5.5 Hz, NH, 1H), 3.90 (s, CH₃, 3H), 3.58 (t, J=4.5 Hz, CH₂×2, 4H), 3.54-3.50 (m, CH₂, 2H), 2.55 (t, J=7.0 Hz, CH₂, 2H), 2.42 (br, CH₂×2, 4H); ¹³C NMR (125 MHz, DMSO-d₆): δ 159.51, 157.62, 153.20, 141.26, 137.42, 129.18, 129.10, 123.40, 122.38, 118.35, 113.92, 104.46, 66.33, 56.34, 53.07, 38.67, 37.37; ESI-MS: m/z=406 [M+1]⁺.

Preparation Embodiment 14: Synthesis of Compounds 14-19

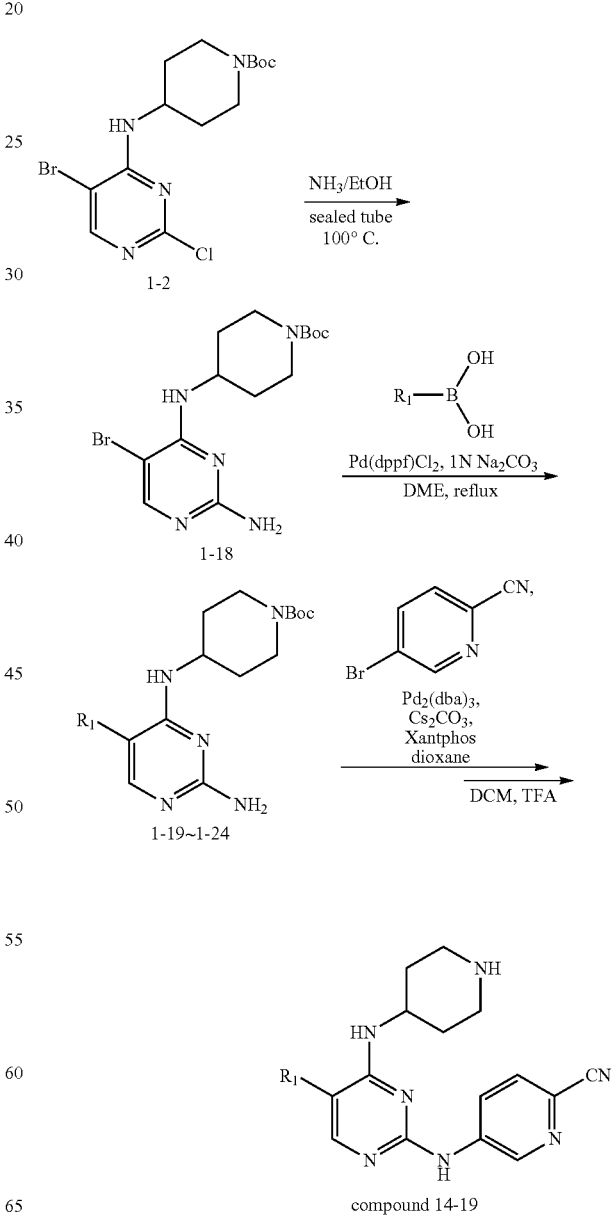

compound 14-19

-continued 1-19: R₁ = 3-fluorophenyl
1-20: R₁ = 1-methyl-1H-pyrazol-4-yl
1-21: R₁ = thien-2-yl
1-22: R₁ = furan-2-yl
1-23: R₁ = 5-methoxycarbonylthiophen-2-yl
1-24: R₁ = 5-methoxycarbonylfuran-2-yl
compound 14: R₁ = 3-fluorophenyl
compound 15: R₁ = 1-methyl-1H-pyrazol-4-yl
compound 16: R₁ = thien-2-yl
compound 17: R₁ = thien-2-yl
compound 18: R₁ = 5-methoxycarbonylthiophen-2-yl
compound 19: R₁ = 5-methoxycarbonylfuran-2-yl Step 1: Synthesis of 2-chloro-5-bromo-N-(N-tert-butoxycarbonylpiperidin-4-yl)-4-aminopyrimidine (Intermediate 1-18)

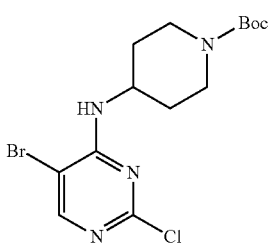 [SMILES: CC(C)(C)OC(=O)N1CCC(Nc2nc(Cl)ncc2Br)CC1]

wherein a synthetic procedure refers to the step 2 of the preparation embodiment 7; the intermediate 1-18 is synthesized by a synthetic method similar to that of the compound 1-6. Yield: 82%; mp: 72-74° C.; $^1$H NMR (500 MHz, DMSO-d$_6$): δ 8.26 (s, Ar—H, 1H), 7.38 (d, J=10.0 Hz, NH, 1H), 4.17-4.08 (m, CH, 1H), 3.98-3.95 (m, CH$_2$, 2H), 2.82-2.79 (m, CH$_2$, 2H), 1.76-1.72 (m, CH$_2$, 2H), 1.61-1.51 (m, CH$_2$, 2H), 1.41 (s, CH$_3$×3, 9H); ESI-MS: m/z=391 [M+1]$^+$.

Step 2: Synthesis of Intermediates 1-19~1-24 wherein a synthetic procedure refers to the step 3 of the preparation embodiment 1; the intermediates 1-19~1-24 are synthesized with the intermediate 1-2 and corresponding boric acid or boronic acid pinacol ester as starting materials.

Step 3: Synthesis of Compounds 14-19 wherein a synthetic procedure refers to the step 4 of the preparation embodiment 7; the compounds 14-19 are synthesized with the intermediates 1-19~1-24 and 5-bromo-2-cyanopyridine as starting materials, so as to obtain white solid.

Preparation Embodiment 15: (R)-5-(1-methyl-1H-pyrazol-4-yl)-N²-(2-cyanopyridin-5-yl)-N⁴-(piperidin-3-yl)-2,4-diaminopyrimidine (Compound 20)

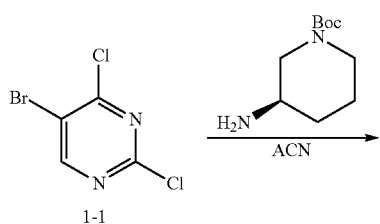

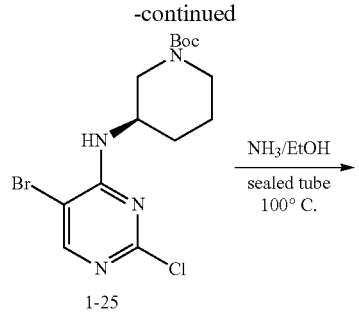

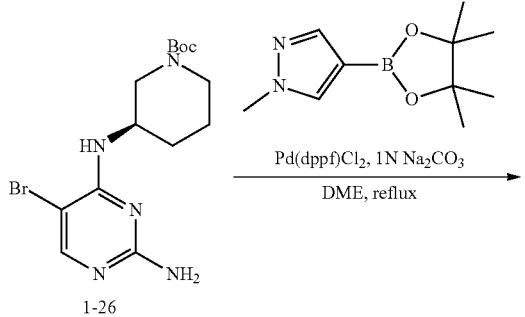

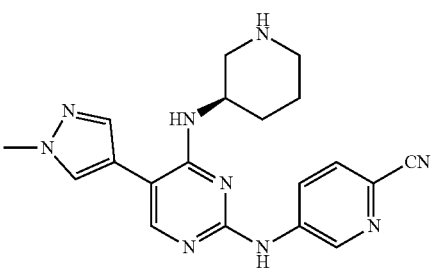

Compound 20

Step 1: Synthesis of (R)-2-chloro-5-bromo-N-(N-tert-butoxycarbonylpiperidin-3-yl)-4-aminopyrimidine (Intermediate 1-25)

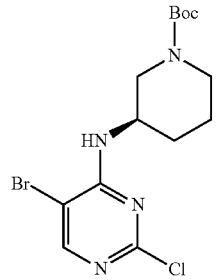 [SMILES: CC(C)(C)OC(=O)N1CCC[C@@H](Nc2nc(Cl)ncc2Br)C1]

wherein a synthetic procedure refers to the step 1 of the preparation embodiment 1; the intermediate 1-25 is synthesized by a synthetic method similar to that of the compound 1-2 with the intermediate 1-1 and (R)—N-tert-butoxycarbonyl-3-aminopiperidine as starting materials. Yield: 85%; $^1$H NMR (500 MHz, DMSO-d$_6$): δ 8.24 (s, Ar—H, 1H), 7.35 (d, J=10.0 Hz, NH, 1H), 4.13-4.06 (m, CH, 1H), 3.94-3.91 (m, CH$_2$, 2H), 2.81-2.75 (m, CH$_2$, 2H), 1.73-1.69 (m, CH$_2$, 2H), 1.60-1.49 (m, CH$_2$, 2H), 1.39 (s, CH$_3$×3, 9H); ESI-MS: m/z=391 [M+1]$^+$.

Step 2: Synthesis of (R)-5-bromo-N$^4$-(N-tert-butoxycarbonylpiperidin-3-yl)-2,4-diaminopyrimidine (Intermediate 1-26)

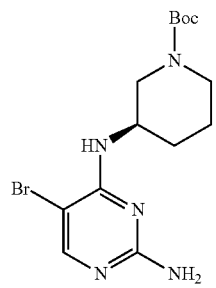 [SMILES: CC(C)(C)OC(=O)N1CCC[C@@H](Nc2nc(N)ncc2Br)C1]

wherein a synthetic procedure refers to the step 2 of the preparation embodiment 7; the intermediate 1-26 is synthesized by a synthetic method similar to that of the compound 1-6. Yield: 79%; $^1$H NMR (500 MHz, DMSO-d$_6$): δ 7.82 (s, Ar—H, 1H), 6.24 (s, NH$_2$, 2H), 5.99 (br, NH, 1H), 3.99 (br, CH, 1H), 3.62-3.57 (m, CH$_2$, 2H), 3.00 (br, CH$_2$, 2H), 1.83-1.80 (m, CH$_2$, 1H), 1.68-1.63 (m, CH$_2$, 2H), 1.41-1.37 (m, CH$_2$, 1H), 1.37 (s, CH$_3$×3, 9H); ESI-MS: m/z=372 [M+1]$^+$.

Step 3: Synthesis of (R)-5-(1-methyl-1H-pyrazol-4-yl)-N$^4$-(N-tert-butoxycarbonylpiperidin-3-yl)-2,4-diaminopyrimidine (Intermediate 1-27)

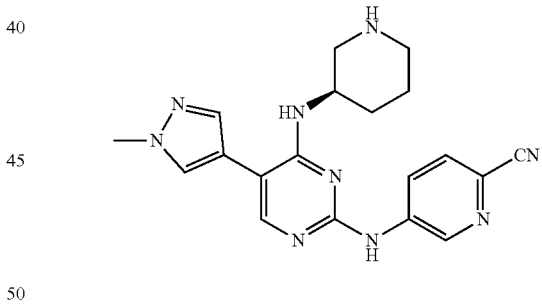

wherein a synthetic procedure refers to the step 3 of the preparation embodiment 1; the intermediate 1-27 is synthesized with the intermediate 1-26 and 1-methyl-1H-pyrazol-4-boronic acid pinacol ester as starting materials. Yield: 81%; $^1$H NMR (500 MHz, DMSO-d$_6$): δ 7.75 (s, Ar—H, 1H), 7.62 (s, Ar—H, 1H), 7.47 (s, Ar—H, 1H), 5.98 (s, NH$_2$, 2H), 5.49 (br, NH, 1H), 4.05-3.99 (br, CH, 1H), 3.71-3.43 (m, CH$_2$, 2H), 3.03 (br, CH$_2$, 2H), 1.81-1.78 (m, CH$_2$, 1H), 1.59-1.56 (m, CH$_2$, 2H), 1.42-1.33 (m, CH$_2$, 1H), 1.33 (s, CH$_3$×3, 9H); ESI-MS: m/z=374 [M+1]$^+$.

Step 4: Synthesis of (R)-5-(1-methyl-1H-pyrazol-4-yl)-N$^2$-(2-cyanopyridin-5-yl)-N$^4$-(piperidin-3-yl)-2,4-diaminopyrimidine (Compound 20)

wherein a synthetic procedure refers to the step 4 of the preparation embodiment 7; the compound 20 is synthesized with the intermediate 1-27 and 5-bromo-2-cyanopyridine as starting materials, so as to obtain a white solid. Yield: 68%; mp: 82-84° C.; $^1$H NMR (500 MHz, DMSO-d$_6$): δ 9.91 (br, NH, 1H), 9.04 (d, J=2.5 Hz, Ar—H, 1H), 8.48 (dd, J=8.5 Hz, 2.5 Hz, Ar—H, 1H), 7.91 (s, Ar—H, 2H), 7.90 (d, J=8.5 Hz, Ar—H, 1H), 7.63 (s, Ar—H, 1H), 6.17 (d, J=8.0 Hz, NH, 1H), 4.08-4.04 (m, CH, 1H), 3.90 (s, CH$_3$, 3H), 2.97-2.94 (m, CH$_2$, 1H), 2.73-2.69 (m, CH$_2$, 1H), 2.61-2.54 (m, CH$_2$, 2H), 1.82-1.78 (m, CH$_2$, 1H), 1.68-1.63 (m, CH$_2$, 1H), 1.61-1.55 (m, CH$_2$, 1H), 1.48-1.41 (m, CH$_2$, 1H); $^{13}$C NMR (125 MHz, DMSO-d$_6$): δ 158.86, 157.64, 153.50, 141.28, 141.19, 137.32, 129.24, 129.17, 123.32, 122.36, 118.33, 113.92, 104.44, 50.81, 47.08, 45.98, 38.69, 29.50, 24.13; ESI-MS: m/z=376 [M+1]$^+$.

Preparation Embodiment 16: (S)-5-(1-methyl-1H-pyrazol-4-yl)-N²-(2-cyanopyridin-5-yl)-N⁴-(piperidin-3-yl)-2,4-diaminopyrimidine (Compound 21)

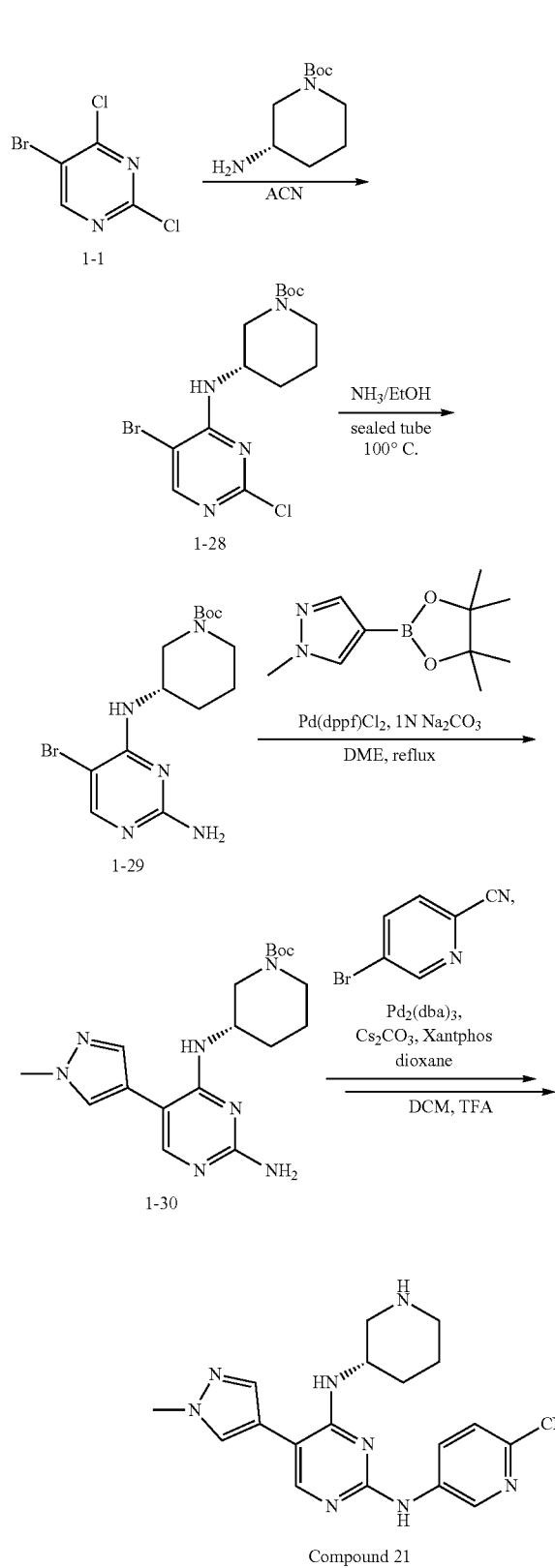

Step 1: Synthesis of (S)-2-chloro-5-bromo-N-(N-tert-butoxycarbonylpiperidin-3-yl)-4-aminopyrimidine (Intermediate 1-28)

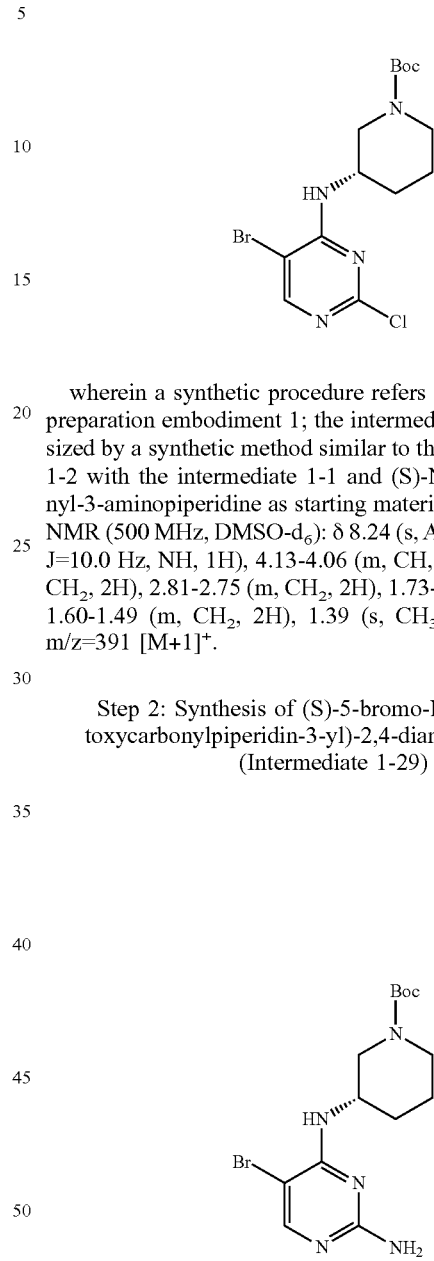

wherein a synthetic procedure refers to the step 1 of the preparation embodiment 1; the intermediate 1-28 is synthesized by a synthetic method similar to that of the compound 1-2 with the intermediate 1-1 and (S)-N-tert-butoxycarbonyl-3-aminopiperidine as starting materials. Yield: 82%; $^1$H NMR (500 MHz, DMSO-d$_6$): δ 8.24 (s, Ar—H, 1H), 7.35 (d, J=10.0 Hz, NH, 1H), 4.13-4.06 (m, CH, 1H), 3.94-3.91 (m, CH$_2$, 2H), 2.81-2.75 (m, CH$_2$, 2H), 1.73-1.69 (m, CH$_2$, 2H), 1.60-1.49 (m, CH$_2$, 2H), 1.39 (s, CH$_3$×3, 9H); ESI-MS: m/z=391 [M+1]$^+$.

Step 2: Synthesis of (S)-5-bromo-N⁴-(N-tert-butoxycarbonylpiperidin-3-yl)-2,4-diaminopyrimidine (Intermediate 1-29)

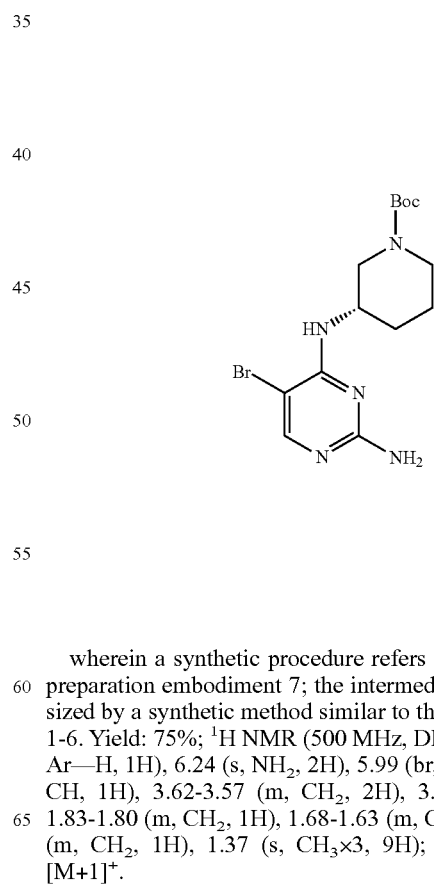

wherein a synthetic procedure refers to the step 2 of the preparation embodiment 7; the intermediate 1-29 is synthesized by a synthetic method similar to that of the compound 1-6. Yield: 75%; $^1$H NMR (500 MHz, DMSO-d$_6$): δ 7.82 (s, Ar—H, 1H), 6.24 (s, NH$_2$, 2H), 5.99 (br, NH, 1H), 3.99 (br, CH, 1H), 3.62-3.57 (m, CH$_2$, 2H), 3.00 (br, CH$_2$, 2H), 1.83-1.80 (m, CH$_2$, 1H), 1.68-1.63 (m, CH$_2$, 2H), 1.41-1.37 (m, CH$_2$, 1H), 1.37 (s, CH$_3$×3, 9H); ESI-MS: m/z=372 [M+1]$^+$.

Step 3: Synthesis of (S)-5-(1-methyl-1H-pyrazol-4-yl)-N⁴-(N-tert-butoxycarbonylpiperidin-3-yl)-2,4-diaminopyrimidine (Intermediate 1-30)

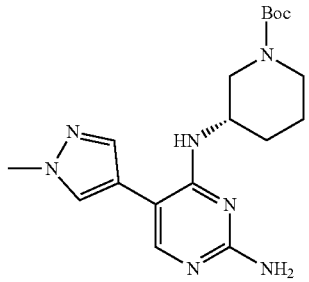 [SMILES: Cn1cc(-c2cnc(N)nc2N[C@H]2CCCN(C(=O)OC(C)(C)C)C2)cn1]

wherein a synthetic procedure refers to the step 3 of the preparation embodiment 1; the intermediate 1-30 is synthesized with the intermediate 1-29 and 1-methyl-1H-pyrazol-4-boronic acid pinacol ester as starting materials. Yield: 78%; ¹H NMR (500 MHz, DMSO-d₆): δ 7.75 (s, Ar—H, 1H), 7.62 (s, Ar—H, 1H), 7.47 (s, Ar—H, 1H), 5.98 (s, NH₂, 2H), 5.49 (br, NH, 1H), 4.05-3.99 (br, CH, 1H), 3.71-3.43 (m, CH₂, 2H), 3.03 (br, CH₂, 2H), 1.81-1.78 (m, CH₂, 1H), 1.59-1.56 (m, CH₂, 2H), 1.42-1.33 (m, CH₂, 1H), 1.33 (s, CH₃×3, 9H); ESI-MS: m/z=374 [M+1]⁺.

Step 4: Synthesis of (S)-5-(1-methyl-1H-pyrazol-4-yl)-N²-(2-cyanopyridin-5-yl)-N⁴-(piperidin-3-yl)-2,4-diaminopyrimidine (Compound 21)

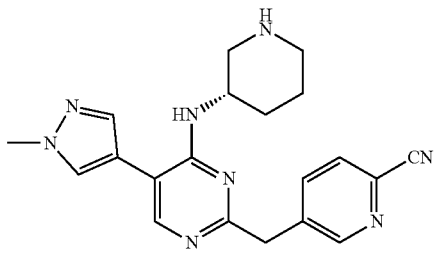 [SMILES: Cn1cc(-c2cnc(Cc3ccc(C#N)nc3)nc2N[C@H]2CCCNC2)cn1]

wherein a synthetic procedure refers to the step 4 of the preparation embodiment 7; the compound 21 is synthesized with the intermediate 1-30 and 5-bromo-2-cyanopyridine as starting materials, so as to obtain a white solid. Yield: 63%; mp: 206-208° C.; ¹H NMR (500 MHz, DMSO-d₆): δ 9.92 (br, NH, 1H), 9.05 (d, J=2.5 Hz, Ar—H, 1H), 8.49 (dd, J=8.5 Hz, 2.5 Hz, Ar—H, 1H), 7.92 (s, Ar—H, 2H), 7.90 (d, J=9.0 Hz, Ar—H, 1H), 7.63 (s, Ar—H, 1H), 6.17 (d, J=8.0 Hz, NH, 1H), 4.09-4.06 (m, CH, 1H), 3.90 (s, CH₃, 3H), 2.98-2.95 (m, CH₂, 1H), 2.74-2.71 (m, CH₂, 1H), 2.62-2.56 (m, CH₂, 2H), 1.83-1.79 (m, CH₂, 1H), 1.69-1.64 (m, CH₂, 1H), 1.61-1.58 (m, CH₂, 1H), 1.48-1.42 (m, CH₂, 1H); ¹³C NMR (125 MHz, DMSO-d₆): δ 158.86, 157.64, 153.50, 141.28, 141.19, 137.32, 129.24, 129.17, 123.32, 122.36, 118.33, 113.92, 104.44, 50.81, 47.08, 45.98, 38.69, 29.50, 24.13; ESI-MS: m/z=376 [M+1]⁺.

Preparation Embodiment 17: (R)-5-(1-methyl-1H-pyrazol-4-yl)-N-(2-cyanopyridin-5-yl)-4-(3-aminopiperidin-1-yl)-2-aminopyrimidine (Compound 22)

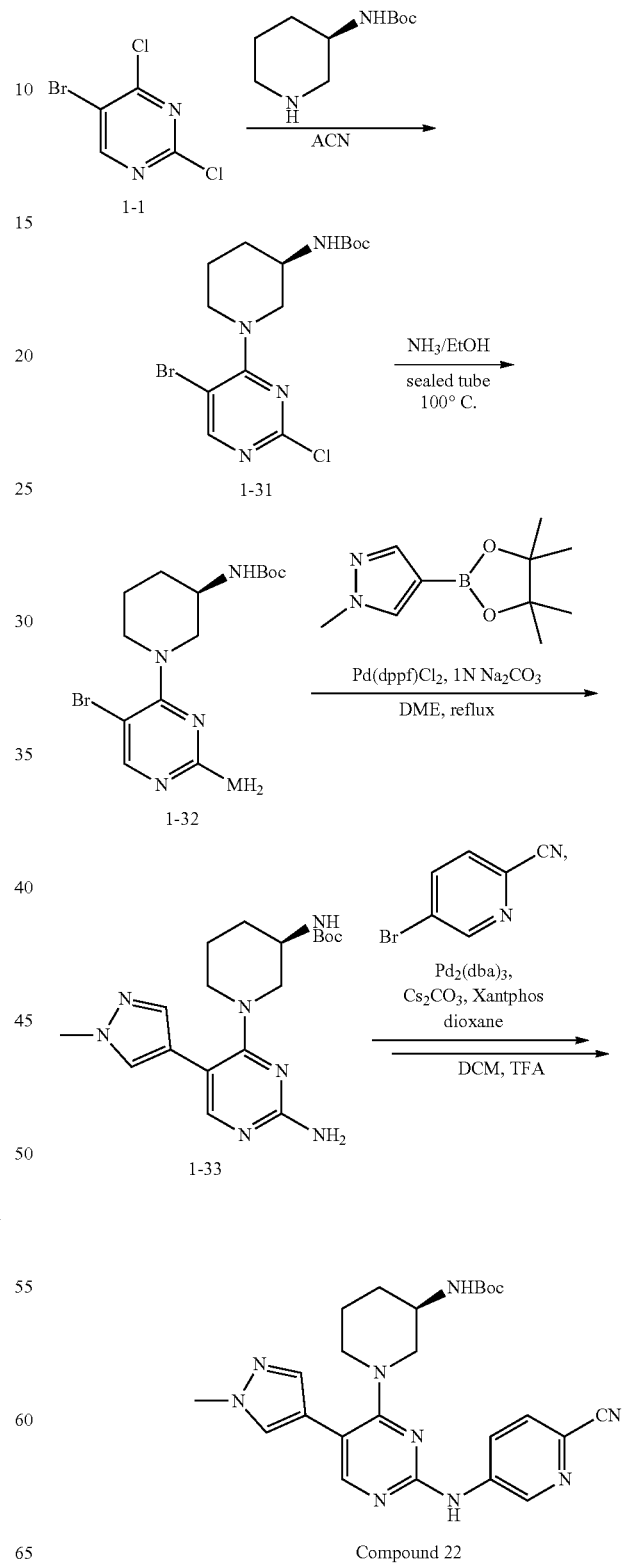

Compound 22

Step 1: Synthesis of (R)-2-chloro-5-bromo-4-(3-tert-butoxycarbonylaminopiperidin-1-yl)pyrimidine (Intermediate 1-31)

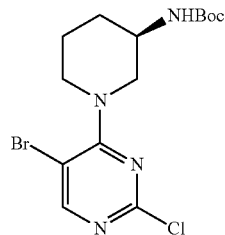

wherein a synthetic procedure refers to the step 1 of the preparation embodiment 1; the intermediate 1-31 is synthesized by a synthetic method similar to that of the compound 1-2 with the intermediate 1-1 and (R)-(3-tert-butoxycarbonylamino)piperidine as starting materials. Yield: 81%; $^1$H NMR (500 MHz, DMSO-d$_6$): δ 8.01 (s, Ar—H, 1H), 3.60-2.56 (m, CH, 1H), 3.31-3.06 (m, CH$_2$, 2H), 2.98-2.94 (m, CH$_2$, 2H), 1.85-1.60 (m, CH$_2$, 2H), 1.53-1.43 (m, CH$_2$, 2H), 1.38 (s, CH$_3$×3, 9H); ESI-MS: m/z=391 [M+1]$^+$.

Step 2: Synthesis of (R)-5-bromo-4-(3-tert-butoxycarbonylaminopiperidin-1-yl)-2-aminopyrimidine (Intermediate 1-32)

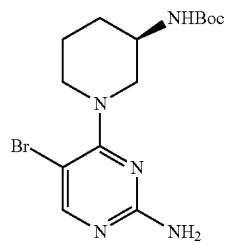 [SMILES: CC(C)(C)OC(=O)N[C@@H]1CCCN(c2nc(N)ncc2Br)C1]

wherein a synthetic procedure refers to the step 2 of the preparation embodiment 7; the intermediate 1-32 is synthesized by a synthetic method similar to that of the compound 1-6. Yield: 72%; mp: 87-89° C.; $^1$H NMR (500 MHz, CDCl$_3$): δ 7.97 (s, Ar—H, 1H), 6.89 (d, J=8.0 Hz, NH, 1H), 6.49 (s, NH$_2$, 2H), 3.95-3.88 (m, CH$_2$, 2H), 2.77-2.67 (m, CH$_2$, 2H), 1.87-1.84 (m, CH, 1H), 1.76-1.73 (m, CH$_2$, 1H), 1.61-1.52 (m, CH$_2$, 1H), 1.39 (s, CH$_3$×3, 9H), 1.38-1.34 (m, CH$_2$, 2H); ESI-MS: m/z=372 [M+1]$^+$.

Step 3: Synthesis of (R)-5-(1-methyl-1H-pyrazol-4-yl)-4-(3-tert-butoxycarbonylaminopiperidin-1-yl)-2-aminopyrimidine (Intermediate 1-33)

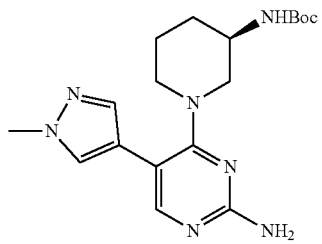

wherein a synthetic procedure refers to the step 3 of the preparation embodiment 1; the intermediate 1-33 is synthesized with the intermediate 1-32 and 1-methyl-1H-pyrazol-4-boronic acid pinacol ester as starting materials. Yield: 68%; $^1$H NMR (500 MHz, DMSO-d$_6$): δ 7.75 (s, Ar—H, 1H), 7.62 (s, Ar—H, 1H), 7.56 (s, Ar—H, 1H), 6.93 (d, J=8.0 Hz, NH, 1H), 3.88 (s, CH$_3$, 3H), 3.64-3.61 (m, CH$_2$, 1H), 3.44-3.41 (m, CH, 1H), 2.71-2.69 (m, CH$_2$, 1H), 2.62-2.60 (m, CH$_2$, 1H), 1.81-1.79 (m, CH$_2$, 1H), 1.63-1.61 (m, CH$_2$, 1H), 1.57-1.54 (m, CH$_2$, 1H), 1.39 (s, CH$_3$×3, 9H), 1.32-1.21 (m, CH$_2$, 2H); ESI-MS: m/z=374 [M+1]$^+$.

Step 4: Synthesis of (R)-5-(1-methyl-1H-pyrazol-4-yl)-N-(2-cyanopyridin-5-yl)-4-(3-aminopiperidin-1-yl)-2-aminopyrimidine (Compound 22)

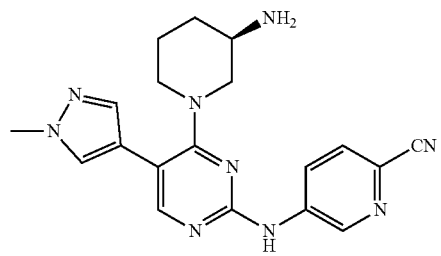 [SMILES: Cn1cc(-c2cnc(Nc3ccc(C#N)nc3)nc2N2CCC[C@@H](N)C2)cn1]

wherein a synthetic procedure refers to the step 4 of the preparation embodiment 7; the compound 22 is synthesized with the intermediate 1-33 and 5-bromo-2-cyanopyridine as starting materials, so as to obtain a white solid. Yield: 60%; mp: 182-184° C.; $^1$H NMR (500 MHz, DMSO-d$_6$): δ 10.10 (br, NH, 1H), 9.04 (d, J=2.5 Hz, Ar—H, 1H), 8.46 (dd, J=9.0 Hz, 2.5 Hz, Ar—H, 1H), 8.12 (s, Ar—H, 1H), 7.93-7.91 (m, Ar—H, 2H), 7.64 (s, Ar—H, 1H), 3.88 (s, CH$_3$, 3H), 3.79-3.76 (m, CH$_2$, 1H), 3.67-3.65 (m, CH$_2$, 1H), 2.74-2.70 (m, CH$_2$, 2H), 1.87-1.82 (m, CH$_2$, 1H), 1.64-1.60 (m, CH$_2$, 2H), 1.51-1.43 (m, CH$_2$, 1H), 1.20-1.13 (m, CH$_2$, 1H); ESI-MS: m/z=376 [M+1]$^+$.

Preparation Embodiment 18: 5-(3-fluorophenyl)-N$^2$-(2-cyanopyrimidin-5-yl)-N$^4$-(2-morpholinethyl)-2,4-diaminopyrimidine (Compound 23)

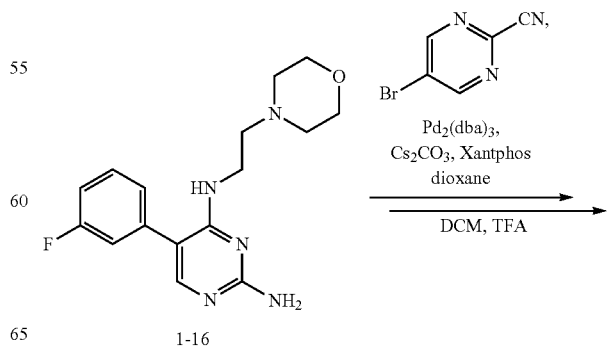

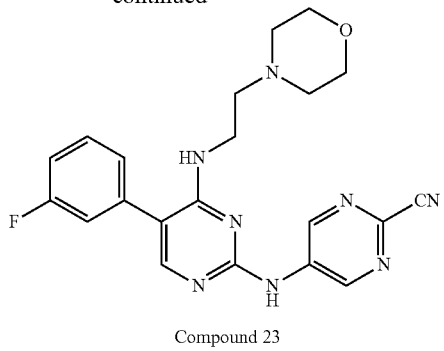

Compound 23

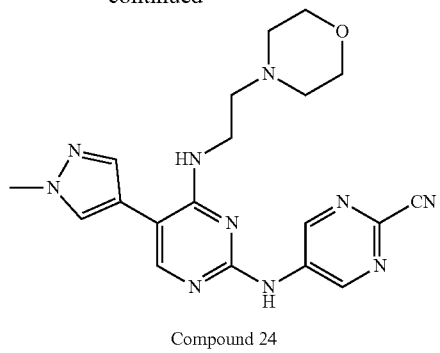

Compound 24

Step 1: Synthesis of 5-(3-fluorophenyl)-$N^2$-(2-cyanopyrimidin-5-yl)-$N^4$-(2-morpholinethyl)-2,4-diaminopyrimidine (Compound 23)

Step 1: Synthesis of 5-(1-methyl-1H-pyrazol-4-yl)-$N^2$-(2-cyanopyrimidin-5-yl)-$N^4$-(2-morpholinethyl)-2,4-diaminopyrimidine (Compound 24)

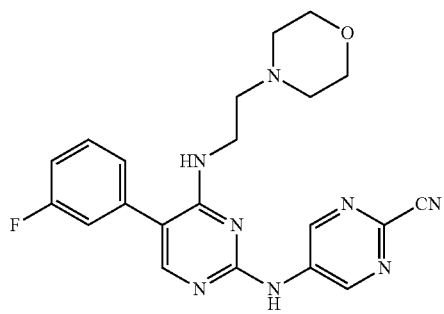 [SMILES: N#Cc1ncc(Nc2ncc(-c3cccc(F)c3)c(NCCN3CCOCC3)n2)cn1]

wherein a synthetic procedure refers to the step 4 of the preparation embodiment 7; the compound 23 is synthesized with the intermediate 1-16 and 5-bromo-2-cyanopyrimidine as starting materials, so as to obtain a white solid. Yield: 82%; mp: 214-216° C.; $^1$H NMR (500 MHz, DMSO-$d_6$): δ 10.19 (s, NH, 1H), 9.36 (s, Ar—H, 2H), 7.94 (s, Ar—H, 1H), 7.57 (dd, J=14.5 Hz, 8.0 Hz, Ar—H, 1H), 7.32-7.23 (m, Ar—H, 3H), 6.76 (t, J=5.0 Hz, NH, 1H), 3.56 (t, J=4.5 Hz, $CH_2 \times 2$, 4H), 3.52 (dd, J=12.0 Hz, 6.0 Hz, $CH_2$, 2H), 2.55 (t, J=6.5 Hz, $CH_2$, 2H), 2.41 (br, $CH_2 \times 2$, 4H); ESI-MS: m/z=421 $[M+1]^+$.

wherein a synthetic procedure refers to the step 4 of the preparation embodiment 7; the compound 24 is synthesized with the intermediate 1-17 and 5-bromo-2-cyanopyrimidine as starting materials, so as to obtain a white solid. Yield: 80%; mp: 170-172° C.; $^1$H NMR (500 MHz, DMSO-$d_6$): δ 10.10 (s, NH, 1H), 9.34 (s, Ar—H, 2H), 7.95 (s, Ar—H, 1H), 7.92 (s, Ar—H, 1H), 7.64 (s, Ar—H, 1H), 6.64 (t, J=5.5 Hz, NH, 1H), 3.90 (s, $CH_3$, 3H), 3.58 (t, J=4.5 Hz, $CH_2 \times 2$, 4H), 3.54 (dd, J=12.5 Hz, 5.5 Hz, $CH_2$, 2H), 2.56 (t, J=6.5 Hz, $CH_2$, 2H), 2.43 (br, $CH_2 \times 2$, 4H); $^{13}$C NMR (125 MHz, DMSO-$d_6$): δ 159.54, 157.13, 153.15, 145.76, 138.76, 137.42, 133.96, 129.15, 116.71, 113.74, 104.93, 66.31, 56.24, 53.07, 38.68, 37.45; ESI-MS: m/z=407 $[M+1]^+$.

Preparation Embodiment 19: 5-(1-methyl-1H-pyrazol-4-yl)-$N^2$-(2-cyanopyrimidin-5-yl)-$N^4$-(2-morpholinethyl)-2,4-diaminopyrimidine (Compound 24)

Preparation Embodiment 20: 5-(1-methyl-1H-pyrazol-4-yl)-$N^2$-(pyridazin-5-yl)-$N^4$-(piperidin-4-yl)-2,4-diaminopyrimidine (Compound 25)

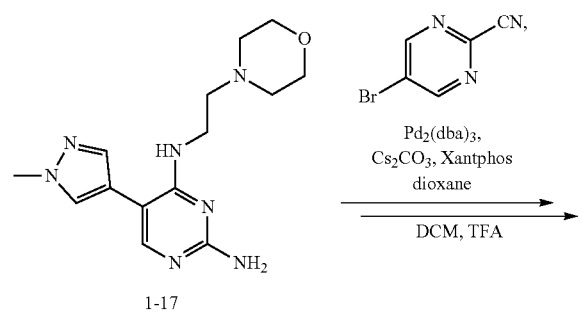

1-17

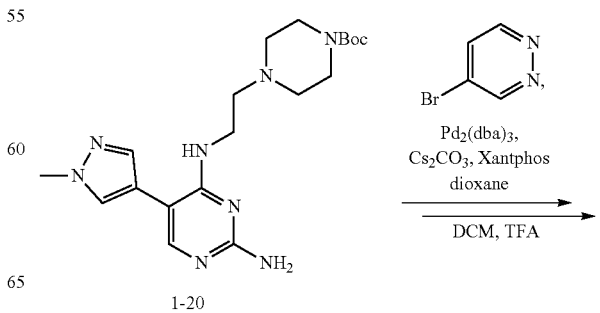

1-20

-continued

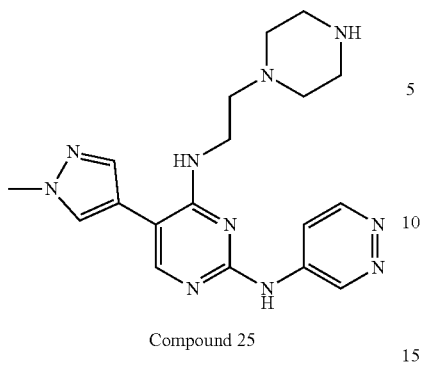

Compound 25

Step 1: Synthesis of 5-(1-methyl-1H-pyrazol-4-yl)-N²-(pyridazin-5-yl)-N⁴-(piperidin-4-yl)-2,4-diaminopyrimidine (Compound 25)

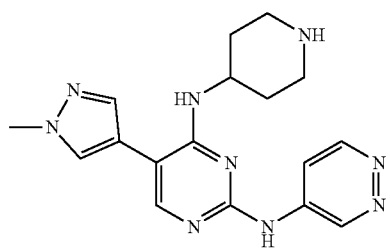 [SMILES: Cn1cc(-c2cnc(Nc3ccnnc3)nc2NC2CCNCC2)cn1]

wherein a synthetic procedure refers to the step 4 of the preparation embodiment 7; the compound 25 is synthesized with the intermediate 1-20 and 5-bromopyridazine as starting materials, so as to obtain a white solid. Yield: 40%; $^1$H NMR (500 MHz, DMSO-$d_6$): δ 10.05 (s, NH, 1H), 9.26 (d, J=9.0 Hz, Ar—H, 1H), 9.18 (s, Ar—H, 1H), 8.20 (s, Ar—H, 1H), 7.96 (s, Ar—H, 1H), 7.95 (s, Ar—H, 1H), 7.06 (d, J=9.0 Hz, Ar—H, 1H), 6.98 (d, J=7.5 Hz, NH, 1H), 3.91 (s, CH$_3$, 3H), 3.60 (t, J=4.5 Hz, CH$_2$×2, 4H), 3.56 (dd, J=12.5 Hz, 5.5 Hz, CH$_2$, 2H), 2.58 (t, J=6.5 Hz, CH$_2$, 2H), 2.45 (br, CH$_2$×2, 4H); ESI-MS: m/z=352 [M+1]$^+$.

Preparation Embodiment 21: 5-(1-methyl-1H-pyrazol-4-yl)-N²-(3-cyanopyridin-6-yl)-N⁴-(piperidin-4-yl)-2,4-diaminopyrimidine (Compound 26)

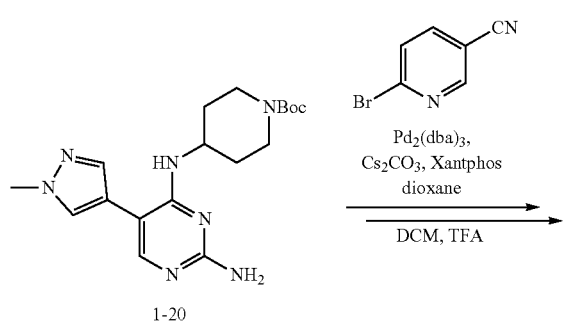

-continued

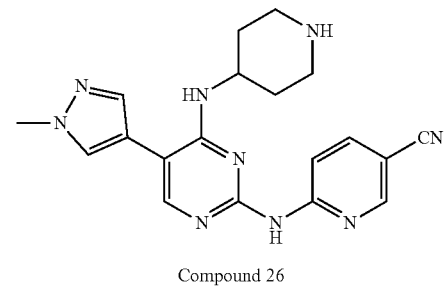

Compound 26

Step 1: Synthesis of 5-(1-methyl-1H-pyrazol-4-yl)-N²-(3-cyanopyridin-6-yl)-N⁴-(piperidin-4-yl)-2,4-diaminopyrimidine (Compound 26)

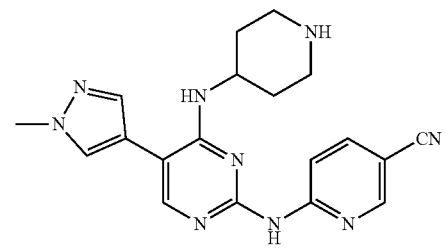 [SMILES: Cn1cc(-c2cnc(Nc3ccc(C#N)cn3)nc2NC2CCNCC2)cn1]

wherein a synthetic procedure refers to the step 4 of the preparation embodiment 7; the compound 26 is synthesized with the intermediate 1-20 and 6-bromo-3-cyanopyridine as starting materials, so as to obtain a white solid. Yield: 57%; $^1$H NMR (500 MHz, DMSO-$d_6$): δ 10.12 (s, NH, 1H), 8.74 (s, Ar—H, 1H), 8.22 (d, J=9.0 Hz, Ar—H, 1H), 8.20 (s, Ar—H, 1H), 7.96 (s, Ar—H, 1H), 7.95 (s, Ar—H, 1H), 7.06 (d, J=9.0 Hz, Ar—H, 1H), 6.65 (d, J=7.0 Hz, NH, 1H), 4.18-4.09 (m, CH, 1H), 3.92 (s, CH$_3$, 3H), 3.36 (br, CH$_2$, 2H), 3.09-2.99 (m, CH$_2$, 2H), 2.11-2.08 (m, CH$_2$, 2H), 1.92-1.85 (m, CH$_2$, 2H); ESI-MS: m/z=376 [M+1]$^+$.

Preparation Embodiment 22: 5-(1-methyl-1H-pyrazol-4-yl)-N²-(2-cyanopyrazin-5-yl)-N⁴-(piperidin-4-yl)-2,4-diaminopyrimidine (Compound 27)

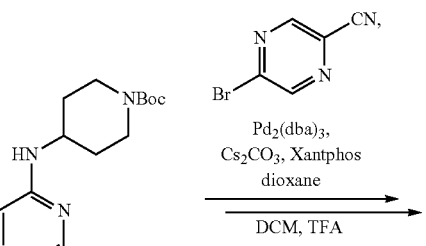

-continued

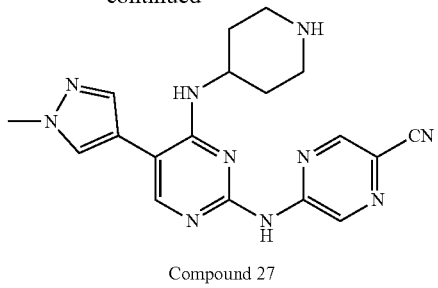

Compound 27

Step 1: Synthesis of 5-(1-methyl-1H-pyrazol-4-yl)-N²-(2-cyanopyrazin-5-yl)-N⁴-(piperidin-4-yl)-2,4-diaminopyrimidine (Compound 27)

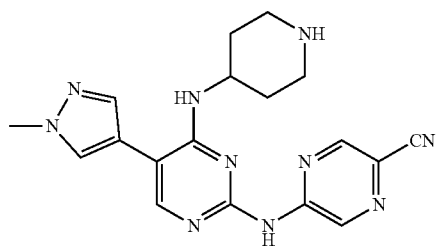 [SMILES: Cn1cc(-c2cnc(Nc3cnc(C#N)cn3)nc2NC2CCNCC2)cn1]

wherein a synthetic procedure refers to the step 4 of the preparation embodiment 7; the compound 27 is synthesized with the intermediate 1-20 and 5-bromo-2-cyanopyrimidine as starting materials, so as to obtain a white solid. Yield: 42%; $^1$H NMR (500 MHz, DMSO-d$_6$): δ 10.28 (s, NH, 1H), 8.36 (s, Ar—H, 1H), 8.28 (s, Ar—H, 1H), 8.20 (s, Ar—H, 1H), 7.96 (s, Ar—H, 1H), 795 (s, Ar—H, 1H), 6.56 (d, J=7.0 Hz, NH, 1H), 4.17-4.10 (m, CH, 1H), 3.92 (s, CH$_3$, 3H), 3.35 (br, CH$_2$, 2H), 3.05-2.98 (m, CH$_2$, 2H), 2.09-2.07 (m, CH$_2$, 2H), 1.93-1.85 (m, CH$_2$, 2H); ESI-MS: m/z=377 [M+1]$^+$.

Preparation Embodiment 23: 5-bromo-N²-(2-cyano-pyridine-5-yl)-N⁴-(piperidin-4-yl)-2,4-diaminopyrimidine (Compound 28)

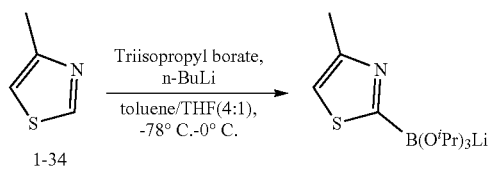

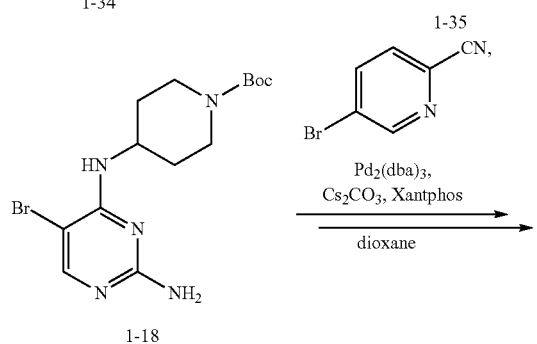

-continued

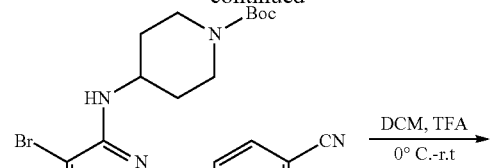

1-36

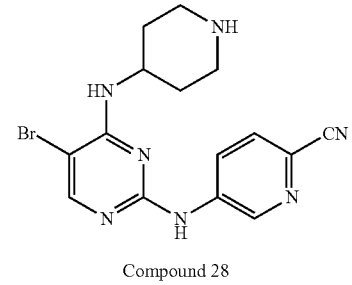

Compound 28

Step 1: Synthesis of lithium(4-methylthiazol-2-yl)borate Triisopropyl Ester (Intermediate 1-35)

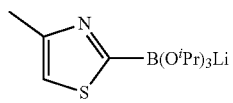

Under nitrogen protection, 4-methylthiazole (1 g, 10.09 mmol) and triisopropyl borate (2.35 mL, 10.09 mmol) were dissolved in a mixed solution of anhydrous toluene and THF (32 mL, v/v, 4:1). The solution was cooled to −78° C. and n-butyl lithium (3.83 mL, 2.5 mol/L, 9.58 mmol) was added dropwise slowly for about 85 min, then stirred for 135 min. The reaction was slowly warmed to 0° C. (about 1.5 h), isopropanol (2.84 mL) was added, then stirred overnight. The reaction was evaporated under reduced pressure to remove the solvent, and anhydrous acetone (17 mL) was added, then was evaporated under reduced pressure to homogeneity, and cooled to room temperature. The residue was filtered under nitrogen protection, washed with acetonitrile (55° C.). The filter cake was dried on vacuum to obtain a white solid used directly in next step without purification.

Step 2: Synthesis of 5-bromo-N²-(2-cyanopyridin-5-yl)-N⁴-(N-tert-butoxycarbonylpiperidin-4-yl)-2,4-diaminopyrimidine (Intermediate 1-36)

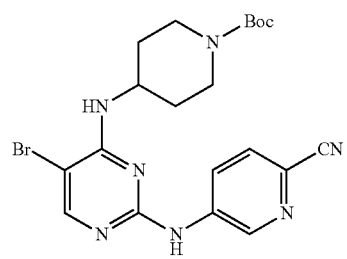 [SMILES: CC(C)(C)OC(=O)N1CCC(Nc2nc(Nc3ccc(C#N)nc3)ncc2Br)CC1]

Under nitrogen protection, to a mixture of the compound 1-18 (367 mg, 0.986 mmol), 5-bromo-2-cyanopyridine (180 mg, 0.986 mmol), tris(dibenzylideneacetone) dipalladium (9 mg, 0.00986 mmol), 4,5-bisdiphenylphosphino-9,9-dimethyloxaxan (15 mg, 0.026 mmol), and cesium carbonate (450 mg, 1.38 mmol), anhydrous dioxane (6 mL) was added. The reaction was stirred refluxing overnight, then was filtered and evaporated under reduced pressure to remove the solvent. The residue was purified by column chromatography on silica gel with $CH_2Cl_2$/EtOH (30:1) as an eluent, so as to obtain a yellow oil. Yield: 77%; $^1$H NMR (500 MHz, DMSO-$d_6$): δ 10.06 (s, NH, 1H), 8.95 (d, J=2.5 Hz, Ar—H, 1H), 8.42 (dd, J=9.0 Hz, 2.5 Hz, Ar—H, 1H), 8.16 (s, Ar—H, 1H), 7.97 (d, J=9.0 Hz, Ar—H, 1H), 6.91 (d, J=8.0 Hz, NH, 1H), 4.17-4.09 (m, CH, 1H), 4.03 (br, $CH_2$, 2H), 2.83 (br, $CH_2$, 2H), 1.85-1.82 (m, $CH_2$, 2H), 1.61-1.52 (m, $CH_2$, 2H), 1.43 (s, $CH_3$×3, 9H); ESI-MS: m/z=474 [M+1]$^+$.

Step 3: Synthesis of 5-bromo-$N^2$-(2-cyanopyridin-5-yl)-$N^4$-(piperidin-4-yl)-2,4-diaminopyrimidine (Compound 28)

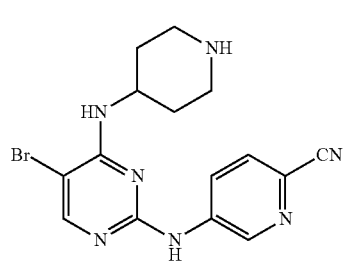 [SMILES: N#Cc1ccc(Nc2ncc(Br)c(NC3CCNCC3)n2)cn1]

To solution of compound 1-36 (123 mg, 0.26 mmol) in dichloromethane (3 mL), trifluoroacetic acid (3 mL) was added dropwise an ice bath. Maintaining the temperature, the reaction was stirred for 30 minutes; then stirred for 4.5 hours at room temperature. Later the reaction was neutralized to pH 9 with saturated sodium bicarbonate, ethyl acetate (40 mL) was added. The organic layer was separated and washed with saturated sodium chloride solution and dried over anhydrous sodium sulfate. The filtrate was evaporated under reduced pressure to give a residue, which was purified by column chromatography on silica gel with $CH_2Cl_2$/EtOH (NH$_3$) (100:3) as an eluent, so as to obtain a white solid. Yield: 79%; mp: 228-230° C.; $^1$H NMR (500 MHz, DMSO-$d_6$): δ 10.01 (br, NH, 1H), 9.02 (d, J=2.5 Hz, Ar—H, 1H), 8.37 (dd, J=8.5 Hz, 2.5 Hz, Ar—H, 1H), 8.14 (s, Ar—H, 1H), 7.91 (d, J=8.5 Hz, Ar—H, 1H), 6.78 (d, J=8.0 Hz, NH, 1H), 4.03-3.95 (m, CH, 1H), 3.00-2.98 (m, $CH_2$, 2H), 2.58-2.53 (m, $CH_2$, 2H), 1.80-1.78 (m, $CH_2$, 2H), 1.57-1.49 (m, $CH_2$, 2H); ESI-MS: m/z=374 [M+1]$^+$.

Preparation Embodiment 24: 5-(4-methylthiazol-2-yl)-$N^2$-(2-cyanopyridin-5-yl)-$N^4$-(piperidin-4-yl)-2,4-diaminopyrimidine (Compound 29)

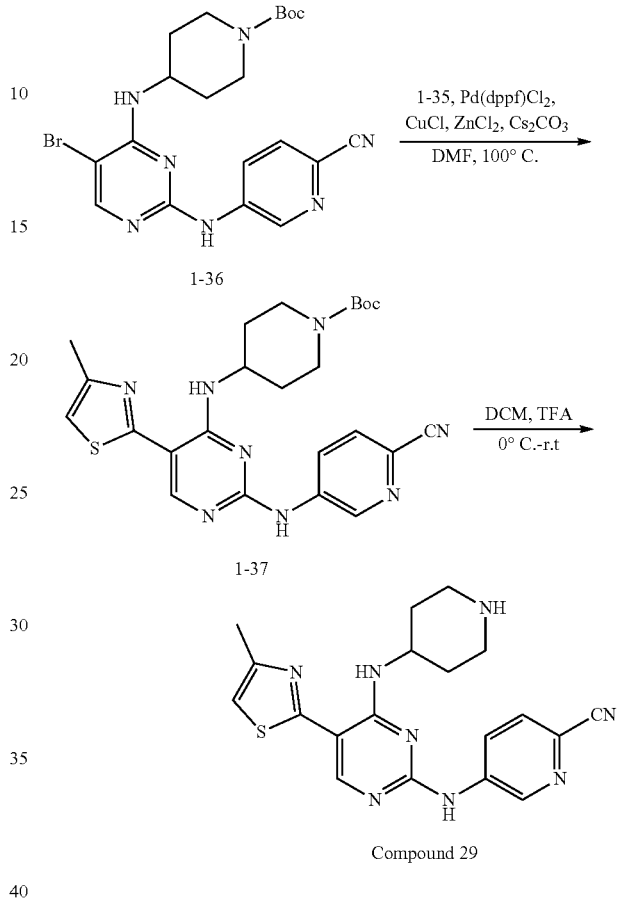

Step 1: Synthesis of 5-(4-methylthiazol-2-yl)-$N^2$-(2-cyanopyridin-5-yl)-$N^4$-(N-tert-butoxycarbonylpiperidin-4-yl)-2,4-diaminopyrimidine (Intermediate 1-37)

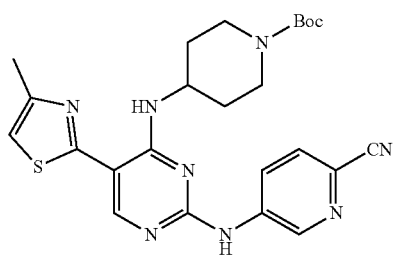 [SMILES: Cc1csc(-c2cnc(Nc3ccc(C#N)nc3)nc2NC2CCN(C(=O)OC(C)(C)C)CC2)n1]

Under nitrogen protection, to a mixture of the compound 1-36 (100 mg, 0.211 mmol), the compound 1-35 (124 mg, 0.422 mmol), Pd(dppf)Cl$_2$ (7.7 mg, 0.011 mmol), CuCl (2.1 mg, 0.021 mmol), ZnCl$_2$ (28.8 mg, 0.211 mmol), and Cs$_2$CO$_3$ (137.5 mg, 0.422 mmol), anhydrous DMF (10 mL) was added. The reaction was heated to 100° C. and stirred overnight. After filteration, the filtrate was evaporated under reduced pressure to give a residue which was purified by column chromatography on silica gel with CH$_2$Cl$_2$/EtOH (30:1) as an eluent, so as to obtain a white solid. Yield: 45%; mp: 208-210° C.; $^1$H NMR (500 MHz, DMSO-d$_6$): δ 10.33 (s, NH, 1H), 9.65 (d, J=7.5 Hz, NH, 1H), 9.03 (d, J=2.5 Hz, Ar—H, 1H), 8.59 (s, Ar—H, 1H), 8.51 (dd, J=8.5 Hz, 2.5 Hz, Ar—H, 1H), 8.00 (d, J=8.5 Hz, Ar—H, 1H), 7.24 (s, Ar—H, 1H), 4.26-4.19 (m, CH, 1H), 3.86-3.83 (m, CH$_2$, 2H), 3.18-3.10 (m, CH$_2$, 2H), 2.42 (s, CH$_3$, 3H), 2.06-2.03 (m, CH$_2$, 2H), 1.53-1.45 (m, CH$_2$, 2H), 1.42 (s, CH$_3$×3, 9H); ESI-MS: m/z=493 [M+1]$^+$.

Step 2: Synthesis of 5-(4-methylthiazol-2-yl)-N$^2$-(2-cyanopyridin-5-yl)-N$^4$-(piperidin-4-yl)-2,4-diaminopyrimidine (Compound 29)

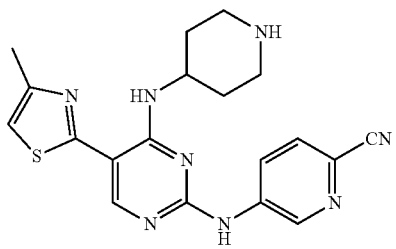 [SMILES: Cc1csc(-c2cnc(Nc3ccc(C#N)nc3)nc2NC2CCNCC2)n1]

wherein the compound 29 is synthesized referring to the step 3 of the preparation embodiment 23, so as to obtain a yellow solid. Yield: 77%; mp: >250° C.; $^1$H NMR (500 MHz, DMSO-d$_6$): δ 10.29 (br, NH, 1H), 9.63 (d, J=7.0 Hz, NH, 1H), 9.09 (d, J=2.5 Hz, Ar—H, 1H), 8.57 (s, Ar—H, 1H), 8.45 (dd, J=9.0 Hz, 2.5 Hz, Ar—H, 1H), 7.95 (d, J=8.5 Hz, Ar—H, 1H), 7.23 (s, Ar—H, 1H), 4.15-4.10 (m, CH, 1H), 3.00-2.96 (m, CH$_2$, 2H), 2.70-2.65 (m, CH$_2$, 2H), 2.42 (s, CH$_3$, 3H), 2.01-1.98 (m, CH$_2$, 2H), 1.48-1.40 (m, CH$_2$, 2H); $^{13}$C NMR (125 MHz, DMSO-d$_6$): δ 163.97, 158.33, 156.83, 155.37, 151.03, 141.67, 140.62, 129.25, 124.25, 123.37, 118.19, 111.59, 103.55, 47.75, 44.42, 32.57, 16.64; ESI-MS: m/z=393 [M+1]$^+$.

Preparation Embodiment 25: 5-bromo-N-(2-cyanopyridin-5-yl)-2-aminopyrimidine (Compound 30)

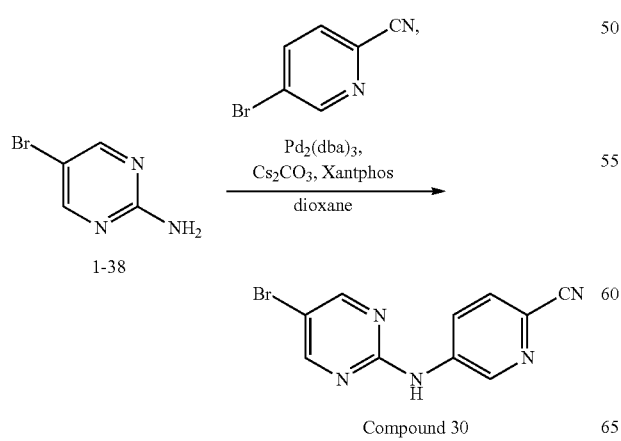

Step 1: Synthesis of 5-bromo-N-(2-cyanopyridin-5-yl)-2-aminopyrimidine (Compound 30)

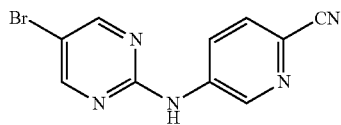 [SMILES: N#Cc1ccc(Nc2ncc(Br)cn2)cn1]

wherein a synthetic procedure refers to the step 4 of the preparation embodiment 7; the compound 30 is synthesized with the intermediate 1-38 and 5-bromo-2-cyanopyrimidine as starting materials, so as to obtain a white solid. Yield: 70%; $^1$H NMR (400 MHz, DMSO-d$_6$): δ 10.64 (s, NH, 1H), 8.98 (s, Ar—H, 1H), 8.76 (s, Ar—H, 2H), 8.43 (d, J=11.0 Hz, Ar—H, 1H), 7.98 (d, J=10.5 Hz, Ar—H, 1H); ESI-MS: m/z=276 [M+1]$^+$.

Preparation Embodiment 26: 5-(2-aminophenyl)-N-(2-cyanopyridin-5-yl)-2-aminopyrimidine (Compound 31)

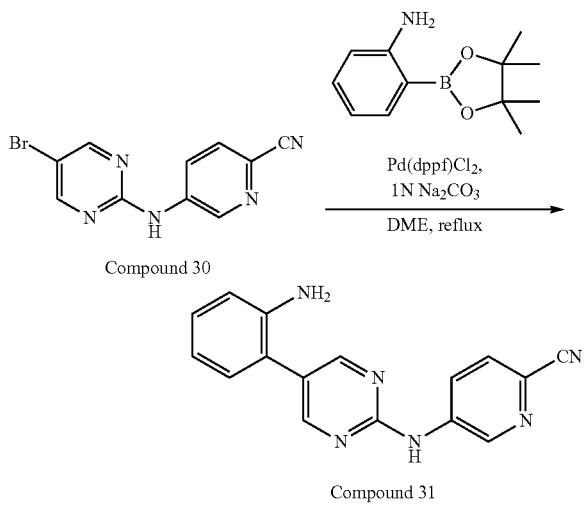

Step 1: Synthesis of 5-(2-aminophenyl)-N-(2-cyanopyridin-5-yl)-2-aminopyrimidine (Compound 31)

wherein a synthetic procedure refers to the step 3 of the preparation embodiment 1; the compound 31 is synthesized with the compound 30 and 2-aminophenylboronic acid pinacol ester as starting materials, so as to obtain a white solid. Yield: 70%; mp: 193-195° C.; $^1$H NMR (500 MHz, DMSO-d$_6$): δ 10.54 (s, NH, 1H), 9.06 (d, J=3.0 Hz, Ar—H, 1H), 8.64 (s, Ar—H, 2H), 8.57 (dd, J=10.5 Hz, 3.0 Hz, Ar—H, 1H), 7.97 (d, J=11.0 Hz, Ar—H, 1H), 7.11 (t, J=10.5 Hz, Ar—H, 1H), 7.05 (d, J=9.0 Hz, Ar—H, 1H), 6.78 (d, J=10.0 Hz, Ar—H, 1H), 6.67 (t, J=9.5 Hz, Ar—H, 1H), 5.04 (br, NH$_2$, 2H); ESI-MS: m/z=289 [M+1]$^+$.

Preparation Embodiment 27: 5-(2-(piperidin-4-yl)aminophenyl)-N-(2-cyanopyridin-5-yl)-2-aminopyrimidine (Compound 32)

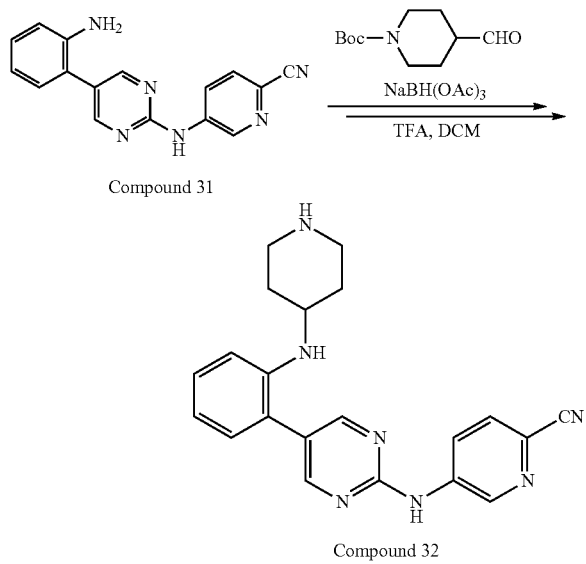

Step 1: Synthesis of 5-(2-(piperidin-4-yl)aminophenyl)-N-(2-cyanopyridin-5-yl)-2-aminopyrimidine (Compound 32)

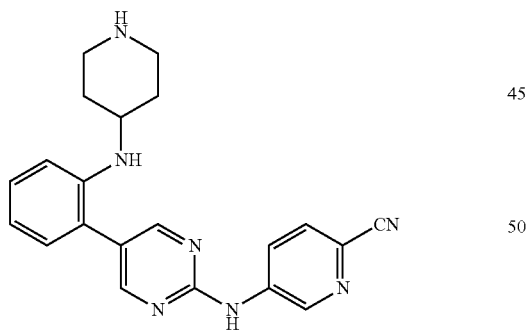

To solution of the compound 31 (175 mg, 0.607 mmol) and N-tert-butoxycarbonyl-4-piperidone (145 mg, 0.728 mmol) in anhydrous CH$_2$Cl$_2$ (4.8 mL), acetic acid (0.056 mL) and sodium triacetoxyborohydride (579 mg, 2.73 mmol) in batches were added. The reaction was stirred for 3 hrs at room temperature. Then saturated ammonium chloride solution was added for quenching the reaction. Ethyl acetate (30 mL) was added, and the organic layer was separated and washed with saturated NaCl solution (30 mL), dried over anhydrous Na$_2$SO$_4$, filtered and evaporated under reduced pressure to give a residue which was purified by column chromatography on silica gel with petroleum ether/acetone (3:1) as an eluent, and deprotecting a Boc protective group with trifluoroacetate, so as to obtain a white solid. Yield: 69%; mp: 213-215° C.; $^1$H NMR (500 MHz, DMSO-d$_6$): δ 10.54 (br, NH, 1H), 9.05 (d, J=3.0 Hz, Ar—H, 1H), 8.60 (s, Ar—H, 2H), 8.58 (dd, J=11.0 Hz, 3.0 Hz, Ar—H, 1H), 7.97 (d, J=11.0 Hz, Ar—H, 1H), 7.21 (t, J=9.0 Hz, Ar—H, 1H), 7.04 (dd, J=9.0 Hz, 2.0 Hz, Ar—H, 1H), 6.77 (d, J=10.5 Hz, Ar—H, 1H), 6.69 (t, J=9.0 Hz, Ar—H, 1H), 4.65 (d, J=10.0 Hz, NH), 3.31-3.27 (m, CH, 1H), 2.92-2.89 (m, CH$_2$, 2H), 2.56-2.49 (m, CH$_2$, 2H), 1.83-1.80 (m, CH$_2$, 2H), 1.30-1.20 (m, CH$_2$, 2H); ESI-MS: m/z=372 [M+1]$^+$.

Preparation Embodiment 28: 5-(2-(piperidin-4-methyl)aminophenyl)-N-(2-cyanopyridin-5-yl)-2-aminopyrimidine (Compound 33)

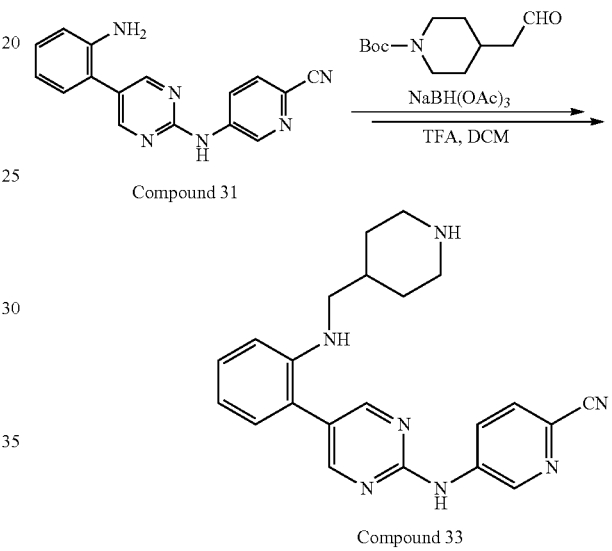

Step 1: Synthesis of 5-(2-(piperidin-4-methyl)aminophenyl)-N-(2-cyanopyridin-5-yl)-2-aminopyrimidine (Compound 33)

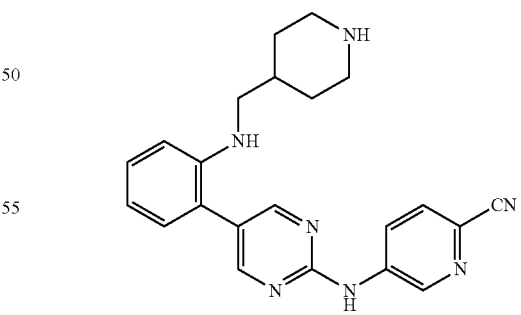

wherein a synthetic procedure refers to the step 1 of the preparation embodiment 27; the compound 32 is synthesized with the compound 31 and N-tert-butoxycarbonyl piperidine formaldehyde as starting materials, so as to obtain a yellow oil. Yield: 69%; $^1$H NMR (500 MHz, DMSO-d$_6$): δ 10.57 (br, NH, 1H), 9.05 (d, J=3.0 Hz, Ar—H, 1H), 8.60 (s, Ar—H, 2H), 8.58 (dd, J=11.0 Hz, 3.0 Hz, Ar—H, 1H), 7.98 (d, J=11.0 Hz, Ar—H, 1H), 7.20 (t, J=9.0 Hz, Ar—H, 1H), 7.04 (dd, J=9.0 Hz, 2.0 Hz, Ar—H, 1H), 6.77 (d, J=10.5 Hz, Ar—H, 1H), 6.69 (t, J=9.0 Hz, Ar—H, 1H), 4.53 (t, J=10.0 Hz, NH), 3.74-3.72 (m, CH$_2$, 2H), 2.72 (t, J=6.0 Hz, CH$_2$, 2H), 2.47-2.42 (m, CH$_2$, 2H), 1.59-1.52 (m, CH, 1H), 1.49-1.46 (m, CH$_2$, 2H), 1.02-0.94 (m, CH$_2$, 2H); ESI-MS: m/z=386 [M+1]$^+$.

Preparation Embodiment 29: Synthesis of Compounds 34-36

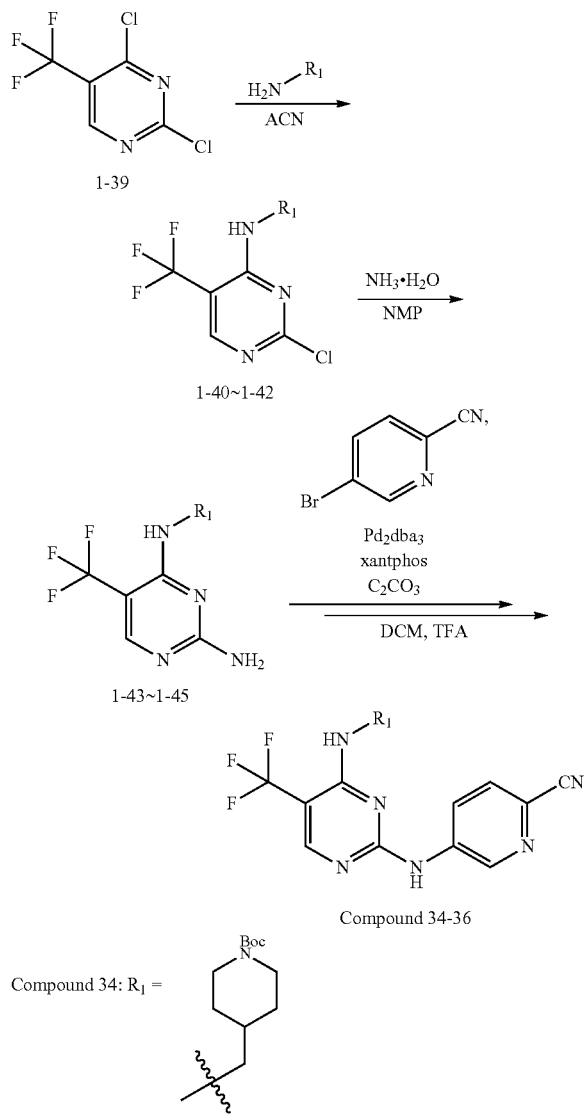

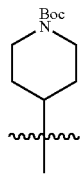

Compound 35: R$_1$ =

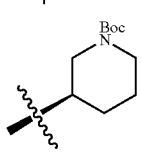

Compound 36: R$_1$ =

Step 1: Synthesis of Intermediates 1-40~1-42 wherein a synthetic procedure refers to the step 1 of the preparation embodiment 1; the intermediates 1-40~1-42 are synthesized by a synthetic method similar to that of the compound 1-2 with the intermediate 1-39 and aminopiperidine as starting materials. Mass spectrometry data are LC-MS: m/z=395 [M+1]$^+$; LC-MS: m/z=381 [M+1]$^+$; LC-MS: m/z=381 [M+1]$^+$, respectively.

Step 2: Synthesis of Intermediates 1-43~1-45

The intermediates 1-40~1-42 (1.23 mmol) were placed in a sealed tube, ammonia (10 mL) and N-methylpyrrolidone (10 mL) were added. The reaction was stirred at 120° C. for 24 h, then cooled to room temperature, and evaporated under reduced pressure to give a residue which was purified by column chromatography on silica gel with PE:EtOAc (2:1) as an eluent, so as to obtain white solid. Mass spectrometry data are LC-MS: m/z=376 [M+1]$^+$; LC-MS: m/z=362 [M+1]$^+$; LC-MS: m/z=362 [M+1]$^+$, respectively.

Step 3: Synthesis of Compounds 34-36 wherein a synthetic procedure refers to the step 4 of the preparation embodiment 7; the compounds 34-36 are synthesized with the intermediates 1-43~1-45 and 5-bromo-2-cyanopyridine as starting materials, so as to obtain white solid. Mass spectrometry data are LC-MS: m/z=378[M+1]$^+$; LC-MS: m/z=364 [M+1]$^+$; LC-MS: m/z=364 [M+1]$^+$, respectively.

The nuclear magnetic and mass spectrometry data of the intermediates 1-19~1-24 and the compound 14-19 are shown in Tables 1-1 and 1-2.

TABLE 1-1

| compound No. | compound name | nuclear magnetic and mass spectrometry data |
|---|---|---|
| intermediate 1-19 | 5-(3-fluorophenyl)-N$^4$-(N-tert-butoxycarbonylpiperidin-4-yl)-2,4-diaminopyrimidine | $^1$H NMR (500 MHz, CDCl$_3$): δ 7.70 (s, Ar—H, 1H), 7.43-7.39 (m, Ar—H, 1H), 7.10 (d, J = 8.0 Hz, Ar—H, 1H), 7.08-7.01 (m, Ar—H, 2H), 4.91 (br, NH$_2$, 2H), 4.76 (d, J = 7.5 Hz, NH, 1H), 4.18-4.09 (m, CH, 1H), 4.02 (br, CH$_2$, 2H), 2.93 (t, J = 10.5 Hz, CH$_2$, 2H), 1.99-1.97 (m, CH$_2$, 2H), 1.45 (s, CH$_3$ × 3, |

TABLE 1-1-continued

| compound No. | compound name | nuclear magnetic and mass spectrometry data |
|---|---|---|
| | | 9H), 1.32-1.27 (m, $CH_2$, 2H); ESI-MS: m/z = 388 [M + 1]$^+$ |
| intermediate 1-20 | 5-(1-methyl-1H-pyrazol-4-yl)-$N^4$-(N-tert-butoxycarbonylpiperidin-4-yl)-2,4-diaminopyrimidine | $^1$H NMR (500 MHz, CDCl$_3$): δ 7.66 (s, Ar—H, 1H), 7.49 (s, Ar—H, 1H), 7.37 (s, Ar—H, 1H), 4.89 (s, $NH_2$, 2H), 4.83 (d, J = 8.0 Hz, NH, 1H), 4.15-4.08 (m, CH, 1H), 4.04 (br, $CH_2$, 2H), 3.96 (s, $CH_3$, 3H), 2.93 (t, J = 12.5 Hz, $CH_2$, 2H), 1.99-1.97 (m, $CH_2$, 2H), 1.46 (s, $CH_3$ × 3, 9H), 1.33-1.25 (m, $CH_2$, 2H); ESI-MS: m/z = 374 [M + 1]$^+$ |
| intermediate 1-21 | 5-(thien-2-yl)-$N^4$-(N-tert-butoxycarbonylpiperidin-4-yl)-2,4-diaminopyrimidine | $^1$H NMR (500 MHz, DMSO-d$_6$): δ 7.73 (br, Ar—H, 1H), 7.51 (d, J = 6.0 Hz, Ar—H, 1H), 7.13-7.11 (m, Ar—H, 1H), 7.08 (s, Ar—H, 1H), 6.22 (br, $NH_2$, 2H), 5.91 (d, J = 10.0 Hz, NH, 1H), 4.15-4.09 (m, CH, 1H), 3.91-3.88 (m, $CH_2$, 2H), 2.82 (br, $CH_2$, 2H), 1.80-1.78 (m, $CH_2$, 2H), 1.45-1.39 (m, $CH_2$, 2H), 1.38 (s, $CH_3$ × 3, 9H); ESI-MS: m/z = 376 [M + 1]$^+$ |
| intermediate 1-22 | 5-(furan-2-yl)-$N^4$-(N-tert-butoxycarbonylpiperidin-4-yl)-2,4-diaminopyrimidine | $^1$H NMR (500 MHz, DMSO-d$_6$): δ 7.98 (br, Ar—H, 1H), 7.66 (s, Ar—H, 1H), 6.54 (br, Ar—H, 1H), 6.28 (br, $NH_2$, 2H), 6.12 (d, J = 10.0 Hz, NH, 1H), 4.22-4.15 (m, CH, 1H), 3.93-3.91 (m, $CH_2$, 2H), 2.84 (br, $CH_2$, 2H), 1.86-1.83 (m, $CH_2$, 2H), 1.49-1.40 (m, $CH_2$, 2H), 1.40 (s, $CH_3$ × 3, 9H); ESI-MS: m/z = 360 [M + 1]$^+$ |
| intermediate 1-23 | 5-(5-methoxycarbonylthiophen-n-2-yl)-$N^4$-(N-tert-butoxycarbonylpiperidin-4-yl)-2,4-diaminopyrimidine | $^1$H NMR (400 MHz, DMSO-d$_6$) δ 7.80 (br, Ar—H, 1H), 7.77 (d, J = 2.8 Hz, Ar—H, 1H), 7.16 (d, J = 2.8 Hz, Ar—H, 1H), 6.39 (br, $NH_2$, 2H), 6.22 (d, J = 6.4 Hz, NH, 1H), 4.20-4.12 (m, CH, 1H), 3.93-3.91 (m, $CH_2$, 2H), 3.82 (s, $CH_3$, 3H), 2.80 (br, $CH_2$, 2H), 1.80-1.78 (m, $CH_2$, 2H), 1.49-1.41 (m, $CH_2$, 2H), 1.39 (s, $CH_3$ × 3, 9H); ESI-MS: m/z = 434 [M + 1]$^+$ |
| intermediate 1-24 | 5-(5-methoxycarbonylfuran-2-yl)-$N^4$-(N-tert-butoxycarbonylpiperidin-4-yl)-2,4-diaminopyrimidine | $^1$H NMR (400 MHz, DMSO-d$_6$) δ 8.21 (s, Ar—H, 1H), 7.39 (d, J = 3.2 Hz, Ar—H, 1H), 6.82 (d, J = 2.8 Hz, Ar—H, 1H), 6.55 (br, $NH_2$, 2H), 6.51 (d, J = 6.0 Hz, NH, 1H), 4.27-4.20 (m, CH, 1H), 3.83 (br, $CH_2$, 2H), 3.81 (s, $CH_3$, 3H), 3.02 (br, $CH_2$, 2H), 1.90-1.87 (m, $CH_2$, 2H), 1.47-1.44 (m, $CH_2$, 2H), 1.41 (s, $CH_3$ × 3, 9H); ESI-MS: m/z = 418 [M + 1]$^+$ |

TABLE 1-2

| compound No. | compound name | nuclear magnetic and mass spectrometry data |
|---|---|---|
| compound 14 | 5-(3-fluorophenyl)-$N^2$-(2-cyanopyridin-5-yl)-$N^4$-(piperidin-4-yl)-2,4-diaminopyrimidine | $^1$H NMR (500 MHz, DMSO-d$_6$): δ 10.02 (s, NH, 1H), 9.09 (d, J = 2.5 Hz, Ar—H, 1H), 8.45 (dd, J = 8.5 Hz, 2.5 Hz, Ar—H, 1H), 7.93 (d, J = 8.5 Hz, Ar—H, 1H), 7.89 (s, Ar—H, 1H), 7.53 (dd, J = 14.5 Hz, 8 Hz, Ar—H, 1H), 7.26-7.24 (m, Ar—H, 2H), 7.23-7.19 (m, Ar—H, 1H), 6.63 (d, J = 7.5 Hz, NH, 1H), 4.13-4.06 (m, CH, 1H), 3.14-3.11 (m, $CH_2$, 2H), 2.78-2.74 (m, $CH_2$, 2H), 1.93-1.91 (m, $CH_2$, 2H), 1.61-1.54 (m, $CH_2$, 2H); ESI-MS: m/z = 390 [M + 1]$^+$ |
| compound 15 | 5-(1-methyl-1H-pyrazol-4-yl)-$N^2$-(2-cyanopyridin-5-yl)-$N^4$-(piperidin-4-yl)-2,4-diaminopyrimidine | $^1$H NMR (500 MHz, DMSO-d$_6$): δ 10.01 (s, NH, 1H), 9.06 (d, J = 2.5 Hz, Ar—H, 1H), 8.44 (dd, J = 9.0 Hz, 2.5 Hz, Ar—H, 1H), 7.94 (d, J = 9.0 Hz, Ar—H, 2H), 7.91 (s, Ar—H, 1H), 7.62 (s, Ar—H, 1H), 6.56 (d, J = 7.0 Hz, NH, 1H), 4.16-4.09 (m, CH, 1H), 3.89 (s, $CH_3$, 3H), 3.35 (br, $CH_2$, 2H), 3.04-2.98 (m, $CH_2$, 2H), 2.07-2.05 (m, $CH_2$, 2H), 1.92-1.86 (m, $CH_2$, 2H); ESI-MS: m/z = 376 [M + 1]$^+$ |

TABLE 1-2-continued

| compound No. | compound name | nuclear magnetic and mass spectrometry data |
|---|---|---|
| compound 16 | 5-(thien-2-yl)-$N^2$-(2-cyanopyridin-5-yl)-$N^4$-(piperidin-4-yl)-2,4-diaminopyrimidine | $^1$H NMR (500 MHz, DMSO-$d_6$): δ 10.06 (br, NH, 1H), 9.09 (s, Ar—H, 1H), 8.46 (d, J = 11.0 Hz, Ar—H, 1H), 7.99 (s, Ar—H, 1H), 7.92 (d, J = 11.0 Hz, Ar—H, 1H), 7.63 (d, J = 6.5 Hz, Ar—H, 1H), 7.24 (d, J = 4.5 Hz, Ar—H, 1H), 7.21-7.18 (m, Ar—H, 1H), 6.38 (d, J = 10.0 Hz, NH, 1H), 4.07-4.00 (m, CH, 1H), 2.98-2.95 (m, CH$_2$, 2H), 2.62-2.56 (m, CH$_2$, 2H), 1.87-1.84 (m, CH$_2$, 2H), 1.49-1.41 (m, CH$_2$, 2H); $^{13}$C NMR (125 M-Hz, DMSO-$d_6$): δ 158.61, 158.06, 155.00, 141.42, 141.02, 135.62, 129.20, 128.20, 126.39, 126.02, 123.75, 122.83, 118.28, 105.78, 48.83, 45.22, 32.38; ESI-MS: m/z = 378 [M + 1]$^+$ |
| compound 17 | 5-(furan-2-yl)-$N^2$-(2-cyanopyridin-5-yl)-$N^4$-(piperidin-4-yl)-2,4-diaminopyrimidine | $^1$H NMR (500 MHz, DMSO-$d_6$): δ 10.09 (br, NH, 1H), 9.08 (d, J = 2.5 Hz, Ar—H, 1H), 8.45 (dd, J = 10.5 Hz, 2.5 Hz, Ar—H, 1H), 8.29 (s, Ar—H, 1H), 7.92 (d, J = 11.0 Hz, Ar—H, 1H), 7.79 (s, Ar—H, 1H), 6.78 (d, J = 4.0 Hz, Ar—H, 1H), 6.63-6.62 (m, Ar—H, 1H), 6.58 (d, J = 9.0 Hz, NH, 1H), 4.09-4.06 (in, CH, 1H), 3.01-2.98 (m, CH$_2$, 2H), 2.65 (t, J = 14.0 Hz, CH$_2$, 2H), 1.93-1.91 (m, CH$_2$, 2H), 1.52-1.44 (m, CH$_2$, 2H); $^{13}$C NMR(125 MHz, DMSO-$d_6$): δ 157.73, 157.02, 153.53, 148.83, 142.36, 141.42, 140.90, 129.17, 123.76, 122.89, 118.25, 111.56, 106.23, 102.46, 48.68, 45.16, 32.57; ESI-MS: m/z = 362 [M + 1]$^+$ |
| compound 18 | 5-(5-methoxycarbonylthiophen-2-yl)-$N^2$-(2-cyanopyridin-5-yl)-$N^4$-(piperidin-4-yl)-2,4-diaminopyrimidine | $^1$H NMR (500 MHz, DMSO-$d_6$): δ 10.13 (br, NH, 1H), 9.08 (s, Ar—H, 1H), 8.44 (d, J = 11.0 Hz, Ar—H, 1H), 8.06 (s, Ar—H, 1H), 7.94 (d, J = 10.5 Hz, Ar—H, 1H), 7.84 (d, J = 5.0 Hz, Ar—H, 1H), 7.30 (d, J = 4.5 HZ, Ar—H, 1H), 6.77 (d, J = 9.5 Hz, NH, 1H), 4.05-4.02 (m, CH, 1H), 3.85 (s, CH$_3$, 3H), 2.99-2.96 (m, CH$_2$, 2H), 2.60 (t, J = 14.5 Hz, CH$_2$, 2H), 1.85-1.82 (m, CH$_2$, 2H), 1.50-1.41 (m, CH$_2$, 2H); $^{13}$C NMR (125 MHz, DMSO-$d_6$): δ 157.73, 157.02, 153.53, 148.83, 142.36, 141.42, 140.90, 129.17, 123.76, 122.89, 118.25, 111.56, 106.23, 102.46, 48.68, 45.16, 32.57; ESI-MS: m/z = 436 [M + 1]$^+$ |
| compound 19 | 5-(5-methoxycarbonylfuran-2-yl)-$N^2$-(2-cyanopyridin-5-yl)-$N^4$-(piperidin-4-yl)-2,4-diaminopyrimidine | $^1$H NMR (500 MHz, DMSO-$d_6$): δ 10.23 (br, NH, 1H), 9.08 (d, J = 2.5 Hz, Ar—H, 1H), 8.48 (s, Ar—H, 1.11), 8.43 (dd, J = 9.0 Hz, 2.5 Hz, Ar—H, 1H), 7.94 (d, J = 9.0 Hz, Ar—H, 1H), 7.45 (d, J = 4.0 Hz, Ar—H, 1H), 7.02 (d, J = 4.0 Hz, Ar—H, 1H), 6.93 (d, J = 7.5 Hz, NH, 1H), 4.15-4.07 (m, CH, 1H), 3.84 (s, CH$_3$, 3H), 3.01-2.99 (m, CH$_2$, 2H), 2.67-2.62 (m, CH$_2$, 2H), 1.96-1.93 (m, CH$_2$, 2H), 1.50-1.42 (m, CH$_2$, 2H); ESI-MS: m/z = 420 [M + 1]$^+$ |

Chk1 Inhibition of the Compounds Disclosed in the Present Invention

Saurosporine is used as a positive control, the Chk1 enzyme inhibitory activity (IC$_{50}$) was evaluated using the ADP-Glo kit. The compound acts on Chk1 protein kinase and inhibits its phosphorylation substrate Cdc25C. The phosphorylation process consumes ATP. After the reaction, ADP-Glo™ Reagent consumes the remaining ATP, wherein ADP produced during the reaction can be transformed to ATP by ADP-Glo Detection Reagent. ATP acts as a substrate for the Ultra-Glo™ luciferase catalytic reaction, producing an optical signal. The test compound was dissolved in DMSO to prepare a 10 mM stock solution and diluted to 12 different concentrations in a certain ratio for testing. 1 μL of the test compound and 2 μL of 2.5× Chk1 kinase were added to each well of a 384-well plate, and 2 μL of 1× buffer was added to the control group. After incubation for 10 min at room temperature, 2 μL of 2.5× substrate was added. Ater incubation for 1 h at 37° C., 5 μL. of ADP-Glo™ Reagent was added and the reaction was stopped before incubating again for 1 h at 37° C. 10 μL of ADP-Glo Detection Reagent was added before incubating for 30 min at 37° C., and three parallel wells were set for each sample. Absorbance was measured by luminescence fluorescence microplate reader, and data were calculated using GraphPad Prism 5 software to calculate IC$_{50}$ values.

Inhibitory Activity of the Compounds Disclosed in the Present Invention on Chk1 Kinase

TABLE 2

IC$_{50}$(μM) of compounds on Chk1 kinase

| Compd. | Chk1 (IC$_{50}$, μM) |
|---|---|
| 1 | >10 μM |
| 2 | >10 μM |
| 3 | >10 μM |
| 4 | >10 μM |
| 5 | >10 μM |
| 6 | >10 μM |
| 7 | 87 |
| 8 | 184 |
| 9 | 35 |
| 10 | 346 |
| 11 | 43 |
| 12 | 1551 |
| 13 | 165 |
| 14 | 118 |
| 15 | 26 |
| 16 | 29.9 |
| 17 | 3.6 |
| 18 | 45.8 |
| 19 | 19.4 |
| 20 | 98.6 |
| 21 | 8.9 |
| 22 | 315 |
| 23 | 1734 |
| 24 | 170 |
| 25 | 65 |
| 26 | >10 μM |
| 27 | >10 μM |
| 28 | 90 |
| 29 | 3.8 |
| 30 | >10 μM |
| 31 | >10 μM |
| 32 | >10 μM |
| 33 | >10 μM |
| 34 | <1 μM |
| 35 | <1 μM |
| 36 | <1 μM |
| Staurosporine | 1.2 |

As can be seen from the data in Table 2, most of the compounds are potent inhibitors of Chk1 protein kinase, and the Chk1 inhibitory activity of three compounds is comparable to the positive compound Staurosporine. Therefore, the 2-substituted pyrimidine derivatives of the present invention used as Chk1 inhibitor have broad antitumor application prospects.

Proliferation Inhibitory Activity of the Compounds Disclosed in the Present Invention on Various Tumor Cells Cell lines: human multiple myeloma cells RPMI 8226, human mantle cell lymphoma cells Mino, Jeko-1, human lymphoma cells Romas, human acute monocytic leukemia cells MV-4-11, human breast cancer cells MCF-7 Human lung cancer cell A549, human prostate cancer cell LnCAP, human gastric cancer cell BGC-823, human colon cancer cell HCT116, Colo205, and human ovarian cancer cell OVCAR-8. Experimental method: using MTS method for in vitro proliferation Inhibitory activity (IC$_{50}$) of compounds against different tumor cell lines.

The cells in the logarithmic growth phase were trypsinized, counted, and seeded at a density of 1×10$^4$ cells/well in a 96-well plate at 100 μL per well before placing in a 37° C. incubator containing 5% CO$_2$ overnight. Six concentration gradients were set for each compound, and three sets of duplicate wells were set for each concentration. After the addition, the cells were cultured for 72 hours, and 20 μL of MTS was added. After incubating for 2 hours at 37° C., the absorbance at 490 nm (L1) was measured with a SpectraMAX 340 microplate reader. The reference wavelength was 690 nm (L2), and the (L1-L2) value was plotted against the different concentrations of the inhibitor. The half inhibitory concentration IC$_{50}$ was fitted by the formula.

TABLE 3-1

Inhibition of proliferation of compounds on each tumor cell line

| | IC$_{50}$(μM)[a] | | | | |
|---|---|---|---|---|---|
| Cpd. | RPMI8226 | Mino | Romas | Jeko-1 | MV-4-11 |
| 17 | 3.339 | 0.708 | 0.536 | 0.342 | 0.044 |
| 21 | 3.597 | 0.608 | 0.401 | 0.253 | 0.035 |
| 39 | 2.781 | 0.503 | 0.550 | 0.184 | 0.035 |

TABLE 3-2

| | IC$_{50}$(μM)[a] | | | | | | |
|---|---|---|---|---|---|---|---|
| Cpd. | MCF-7 | A549 | LnCAP | BGC-823 | HCT116 | OVCAR-8 | Colo205 |
| 17 | 1.796 | 0.774 | 1.440 | 3.172 | 2.677 | 4.705 | 2.770 |
| 21 | 2.561 | 1.023 | 0.842 | 2.106 | 1.392 | 3.241 | 1.542 |
| 39 | 0.986 | 0.847 | 0.889 | 0.642 | 0.998 | 1.612 | 0.987 |

[a]IC$_{50}$: average of three experiments

The Activity of the Compound Disclosed in the Present Invention in Combination with Other Drugs MV 4-11 cells were seeded at 5000/well into 96-well plates. When used in combination, the drug composition is determined according to the ratio of IC$_{50}$ of the two drugs. The concentration range of each drug is IC$_{20}$~IC$_{80}$ (or ⅛, ¼, ½, 1, 2 and 4 of IC$_{50}$). After 72 hours, cell viability was measured by adding MTS reagent, and the inhibition rate Fa was calculated using the unmedicated group as 100%. The Chou-Talalay method was used to input the inhibition rate Fa and the corresponding drug concentration into CompuSyn software for analysis, so as to obtain the CI value and Fa-CI curve of single concentration drug. CI (combination index) is calculated as CI=DA/ICX,A+DB/ICX,B (A, B stands for two different drugs, ICX,A and ICX,B are the proliferation inhibition rate when the drug concentration reaches X and the two drugs are used alone; DA and DB are the concentrations of the two drugs when the proliferation inhibition rate reaches X when the two drugs are combined. The results are shown in FIGURE. Note: CHK1 inhibitor (17); Stat5 inhibitor Pimozide (PMZ); FLT3 inhibitor TCS359 (TCS); Akt inhibitor Hu7151 (Hu); CI=combination index, according to the judgment method of Soriano et al., 0.9≤CI≤1.1 indicates superposition, 0.8≤CI<0.9 indicates low synergy, 0.6≤CI<0.8 indicates moderate synergy, 0.4≤CI<0.6 indicates high synergy, and 0.2≤CI<0.4 indicates strong synergy.

What is claimed is:

1. A compound of formula I, and an optical isomer or a pharmaceutically acceptable salt:

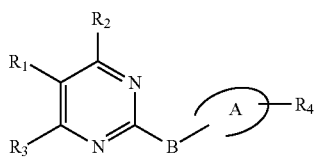

I wherein ring A comprises 1 to 3 substituted penta- or hexa-heterocyclic aryl selected from O, N and S; and a substituent is $R_4$;

B is —NH;

$R_1$ is a penta- or hexa-aromatic ring or aromatic heterocyclic ring containing 1 to 3 hetero atoms selected from O, N and S, and substituted with one, two or three substituents selected from $R_a$;

$R_a$ is selected from H, halogen, nitro, cyano, $C_{1-3}$ alkyl, halogenated $C_{1-3}$ alkyl, —C(=O)$OR_b$, —C(=O)$NHR_b$, —$NHR_b$, —$OR_b$, and —$NHCOR_b$; $R_b$ is selected from H, $C_{1-3}$ alkyl, halogenated $C_{1-3}$ alkyl, $C_{1-3}$ alkoxy, halogenated $C_{1-3}$ alkoxy, and $C_{1-7}$ alkylamine;

$R_2$ is selected from H, —$NHR_c$, —$N(R_c)_2$, —$OR_c$, and —$SR_c$; $R_c$ is selected from penta- to octa-aliphatic ring containing 1 to 3 heteroatoms selected from O and N, $C_{1-7}$ alkyl, $C_{1-7}$ hydroxyalkyl, $C_{1-7}$ alkylamino, and $C_{1-7}$ alkoxy;

$R_3$ is selected from halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, and halogenated $C_{1-3}$ alkylamino;

$R_4$ is selected from H, halogen, nitro, cyano, trifluoromethyl, $C_{1-3}$ alkyl, $C_{1-3}$ alkoxy, C(=O)$NR_dR_e$, $R_d$ and $R_e$ are independently hydrogen, $C_{1-3}$ alkyl.

2. The compound, and the optical isomer or the pharmaceutically acceptable salt, as recited in claim 1, wherein the 2-substituted aromatic ring-pyrimidine has a structure as shown in a formula II:

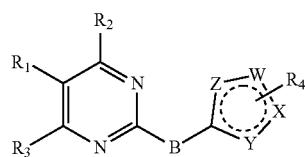

II wherein W, X, Y and Z are identical or different and are independently selected from N, C and O;

B is —NH;

$R_1$ is penta- or hexa-aromatic ring or aromatic heterocyclic ring, containing 1 to 3 hetero atoms selected from O, N and S, and substituted with one, two or three substituents selected from $R_a$;

$R_a$ is selected from H, halogen, nitro, cyano, $C_{1-3}$ alkyl, halogenated $C_{1-3}$ alkyl, —C(=O)$OR_b$, —C(=O)$NHR_b$, —$NHR_b$, —$OR_b$, and —$NHCOR_b$; $R_b$ is selected from H, $C_{1-3}$ alkyl, halogenated $C_{1-3}$ alkyl, $C_{1-3}$ alkoxy, halogenated $C_{1-3}$ alkoxy, and $C_{1-7}$ alkylamine;

$R_2$ is selected from H, —$NHR_c$, —$N(R_c)_2$, —$OR_c$, and —$SR_c$; $R_c$ is selected from penta- to octa-aliphatic ring containing 1 to 3 heteroatoms selected from O and N, $C_{1-7}$ alkyl, $C_{1-7}$ hydroxyalkyl, $C_{1-7}$ alkylamino, and $C_{1-7}$ alkoxy;

$R_3$ is selected from halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, and halogenated $C_{1-3}$ alkylamino;

$R_4$ is selected from H, halogen, nitro, cyano, trifluoromethyl, $C_{1-3}$ alkyl, $C_{1-3}$ alkoxy, C(=O)$NR_dR_e$, $R_d$ and $R_e$ are independently hydrogen, $C_{1-3}$ alkyl.

3. The compound, and the optical isomer or the pharmaceutically acceptable salt, as recited in claim 1, wherein the 2-substituted aromatic ring-pyrimidine has a structure as shown in a formula III:

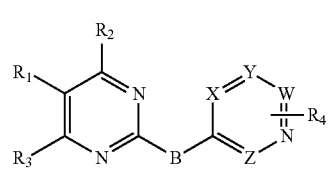

III wherein W, X, Y and Z are identical or different and are independently selected from N and C;

B is —NH $R_1$ is a penta- or hexa-aromatic ring or aromatic heterocyclic ring, containing 1 to 3 hetero atoms selected from O, N and S, and substituted with one, two or three substituents selected from $R_a$;

$R_a$ is selected from H, halogen, nitro, cyano, $C_{1-3}$ alkyl, halogenated $C_{1-3}$ alkyl, —C(=O)$OR_b$, —C(=O)$NHR_b$, —$NHR_b$, —$OR_b$, and —$NHCOR_b$; $R_b$ is selected from H, $C_{1-3}$ alkyl, halogenated $C_{1-3}$ alkyl, $C_{1-3}$ alkoxy, halogenated $C_{1-3}$ alkoxy, and $C_{1-7}$ alkylamine;

$R_2$ is selected from H, —$NHR_c$, —$N(R_c)_2$, —$OR_c$, and —$SR_c$; $R_c$ is selected from penta- to octa-aliphatic ring containing 1 to 3 heteroatoms selected from O and N, $C_{1-7}$ alkyl, $C_{1-7}$ hydroxyalkyl, $C_{1-7}$ alkylamino, and $C_{1-7}$ alkoxy;

$R_3$ is selected from halogen, nitro, cyano, $C_{1-3}$ alkyl, halogenated $C_{1-3}$ alkyl, $C_{1-3}$ alkoxy, halogenated $C_{1-3}$ alkoxy, $C_{1-3}$ alkylamino, and halogenated $C_{1-3}$ alkylamino;

$R_4$ is selected from H, halogen, nitro, cyano, trifluoromethyl, $C_{1-3}$ alkyl, $C_{1-3}$ alkoxy, C(=O)$NR_dR_e$, $R_d$ and $R_e$ are independently hydrogen, $C_{1-3}$ alkyl.

4. The compound, and the optical isomer or the pharmaceutically acceptable salt, as recited in claim 2, wherein the 2-substituted aromatic ring-pyrimidine has a structure as shown in a formula IV:

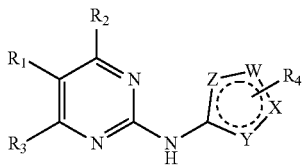

wherein W, X, Y and Z are identical or different and are independently selected from N, C and O;

R$_1$ is a penta- or hexa-aromatic ring or aromatic heterocyclic ring, containing 1 to 3 hetero atoms selected from O, N and S, and substituted with one, two or three substituents selected from R$_a$;

R$_a$ is selected from H, halogen, nitro, cyano, C$_{1-3}$ alkyl, halogenated C$_{1-3}$ alkyl, —C(═O)OR$_b$, —C(═O)NHR$_b$, —NHR$_b$, —OR$_b$, and —NHCOR$_b$; R$_b$ is selected from H, C$_{1-3}$ alkyl, halogenated C$_{1-3}$ alkyl, C$_{1-3}$ alkoxy, halogenated C$_{1-3}$ alkoxy, and C$_{1-7}$ alkylamine;

R$_2$ is selected from H, —NHR$_c$, —N(R$_c$)$_2$, —OR$_c$, and —SR$_c$; R$_c$ is selected from penta- to octa-aliphatic ring containing 1 to 3 heteroatoms selected from O and N, C$_{1-7}$ alkyl, C$_{1-7}$ hydroxyalkyl, C$_{1-7}$ alkylamino, and C$_{1-7}$ alkoxy;

R$_3$ is selected from halogen, nitro, cyano, C$_{1-3}$ alkyl, halogenated C$_{1-3}$ alkyl, C$_{1-3}$ alkoxy, halogenated C$_{1-3}$ alkoxy, C$_{1-3}$ alkylamino, and halogenated C$_{1-3}$ alkylamino;

R$_4$ is selected from H, halogen, nitro, cyano, trifluoromethyl, C$_{1-3}$ alkyl, C$_{1-3}$ alkoxy, C(═O)NR$_d$R$_e$, R$_d$ and R$_e$ are independently hydrogen, C$_{1-3}$ alkyl.

5. The compound, and the optical isomer or the pharmaceutically acceptable salt, as recited in claim 4, wherein the 2-substituted aromatic ring-pyrimidine is selected from:
   5-(1-methyl-1H-pyrazol-4-yl)-N$^2$-(3-methylpyrazol-5-yl)-N$^4$-(piperidin-4-yl)-2,4-diaminopyrimidine,
   5-(1-methyl-1H-pyrazol-4-yl)-N$^2$-(5-methyloxazol-3-yl)-N$^4$-(piperidin-4-yl)-2,4-diaminopyrimidine,
   5-(thien-2-yl)-N$^2$-(5-methylpyrazol-3-yl)-N$^4$-(piperidin-4-yl)-2,4-diaminopyrimidine,
   5-(thien-2-yl)-N$^2$-(5-methyloxazol-3-yl)-N$^4$-(piperidin-4-yl)-2,4-diaminopyrimidine,
   5-(furan-2-yl)-N$^2$-(5-methylpyrazol-3-yl)-N$^4$-(piperidin-4-yl)-2,4-diaminopyrimidine, and
   5-(furan-2-yl)-N$^2$-(5-methyloxazol-3-yl)-N$^4$-(piperidin-4-yl)-2,4-diaminopyrimidine.

6. The compound, and the optical isomer or the pharmaceutically acceptable salt, as recited in claim 3, wherein the 2-substituted aromatic ring-pyrimidine has a structure as shown in a formula V:

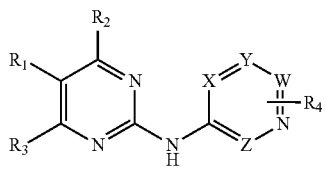

wherein W, X, Y and Z are identical or different and are independently selected from N and C;

R$_1$ is a penta- or hexa-aromatic ring or aromatic heterocyclic ring, containing 1 to 3 hetero atoms selected from O, N and S, and substituted with one, two or three substituents selected from R$_a$;

R$_a$ is selected from H, halogen, nitro, cyano, C$_{1-3}$ alkyl, halogenated C$_{1-3}$ alkyl, —C(═O)OR$_b$, —C(═O)NHR$_b$, —NHR$_b$, —OR$_b$, and —NHCOR$_b$; R$_b$ is selected from H, C$_{1-3}$ alkyl, halogenated C$_{1-3}$ alkyl, C$_{1-3}$ alkoxy, halogenated C$_{1-3}$ alkoxy, and C$_{1-7}$ alkylamine;

R$_2$ is selected from H, —NHR$_c$, —N(R$_c$)$_2$, —OR$_c$, and —SR$_c$; R$_c$ is selected from penta- to octa-aliphatic ring containing 1 to 3 heteroatoms selected from O and N, C$_{1-7}$ alkyl, C$_{1-7}$ hydroxyalkyl, C$_{1-7}$ alkylamino, and C$_{1-7}$ alkoxy;

R$_3$ is selected from halogen, nitro, cyano, C$_{1-3}$ alkyl, halogenated C$_{1-3}$ alkyl, C$_{1-3}$ alkoxy, halogenated C$_{1-3}$ alkoxy, C$_{1-3}$ alkylamino, and halogenated C$_{1-3}$ alkylamino;

R$_4$ is selected from H, halogen, nitro, cyano, trifluoromethyl, C$_{1-3}$ alkyl, C$_{1-3}$ alkoxy, C(═O)NR$_d$R$_e$, R$_d$ and R$_e$ are independently hydrogen, C$_{1-3}$ alkyl.

7. The compound, and the optical isomer or the pharmaceutically acceptable salt, as recited in claim 6, wherein the 2-substituted aromatic ring-pyrimidine is selected from:
   5-phenyl-N$^2$-(2-cyanopyridin-5-yl)-N$^4$-(piperidin-4-methyl)-2,4-diaminopyrimidine,
   5-(3-fluorophenyl)-N$^2$-(2-cyanopyridin-5-yl)-N$^4$-(piperidin-4-methyl)-2,4-diaminopyrimidine,
   5-(1-methyl-1H-pyrazol-4-yl)-N$^2$-(2-cyanopyridin-5-yl)-N$^4$-(piperidin-4-methyl)-2,4-diaminopyrimidine,
   5-(3-fluorophenyl)-N$^2$-(2-cyanopyridin-5-yl)-N$^4$-aminoethyl-2,4-diaminopyrimidine,
   5-(1-methyl-1H-pyrazol-4-yl)-N$^2$-(2-cyanopyridin-5-yl)-N$^4$-aminoethyl-2,4-diaminopyrimidine
   5-(3-fluorophenyl)-N$^2$-(2-cyanopyridin-5-yl)-N$^4$-(2-morpholinethyl)-2,4-diaminopyrimidine,
   5-(1-methyl-1H-pyrazol-4-yl)-N$^2$-(2-cyanopyridin-5-yl)-N$^4$-(2-morpholinethyl)-2,4-diaminopyrimidine,
   5-(3-fluorophenyl)-N$^2$-(2-cyanopyridin-5-yl)-N$^4$-(piperidin-4-yl)-2,4-diaminopyrimidine,
   5-(1-methyl-1H-pyrazol-4-yl)-N$^2$-(2-cyanopyridin-5-yl)-N$^4$-(piperidin-4-yl)-2,4-diaminopyrimidine,
   5-(thien-2-yl)-N$^2$-(2-cyanopyridin-5-yl)-N$^4$-(piperidin-4-yl)-2,4-diaminopyrimidine,
   5-(furan-2-yl)-N$^2$-(2-cyanopyridin-5-yl)-N$^4$-(piperidin-4-yl)-2,4-diaminopyrimidine,
   5-(5-methoxycarbonylthiophen-2-yl)-N$^2$-(2-cyanopyridin-5-yl)-N$^4$-(piperidin-4-yl)-2,4-diaminopyrimidine,
   5-(5-methoxycarbonylfuran-2-yl)-N$^2$-(2-cyanopyridin-5-yl)-N$^4$-(piperidin-4-yl)-2,4-diaminopyrimidine,
   (R)-5-(1-methyl-1H-pyrazol-4-yl)-N$^2$-(2-cyanopyridin-5-yl)-N$^4$-(piperidin-3-yl)-2,4-diaminopyrimidine,
   (S)-5-(1-methyl-1H-pyrazol-4-yl)-N$^2$-(2-cyanopyridin-5-yl)-N$^4$-(piperidin-3-yl)-2,4-diaminopyrimidine,
   (R)-5-(1-methyl-1H-pyrazol-4-yl)-N-(2-cyanopyridin-5-yl)-4-(3-aminopiperidin-1-yl)-2-aminopyrimidine,
   5-(3-fluorophenyl)-N$^2$-(2-cyanopyrimidin-5-yl)-N$^4$-(2-morpholinethyl)-2,4-diaminopyrimidine,
   5-(1-methyl-1H-pyrazol-4-yl)-N$^2$-(2-cyanopyrimidin-5-yl)-N$^4$-(2-morpholinethyl)-2,4-diaminopyrimidine,
   5-(1-methyl-1H-pyrazol-4-yl)-N$^2$-(3-cyanopyridin-6-yl)-N$^4$-(piperidin-4-yl)-2,4-diaminopyrimidine,
   5-(1-methyl-1H-pyrazol-4-yl)-N$^2$-(2-cyanopyrazin-5-yl)-N$^4$-(piperidin-4-yl)-2,4-diaminopyrimidine,
   5-(4-methylthiazol-2-yl)-N$^2$-(2-cyanopyridin-5-yl)-N$^4$-(piperidin-4-yl)-2,4-diaminopyrimidine,
   5-(2-aminophenyl)-N-(2-cyanopyridin-5-yl)-2-aminopyrimidine, 5-(2-(piperidin-4-yl)aminophenyl)-N-(2-cyanopyridin-5-yl)-2-aminopyrimidine, 5-(2-(piperidin-4-methyl)aminophenyl)-N-(2-cyanopyridin-5-yl)-2-aminopyrimidine, and pharmaceutically acceptable salts of the above compounds.

8. A preparation method of a pharmaceutical composition comprising a compound of Formula (I) and an optical isomer or a pharmaceutically acceptable salt, comprising steps of:

method I:

using 5-bromo-2,4-dichloropyrimidine as a starting material, substituting with an aliphatic amine group and an aromatic heterocyclic amine group in sequence, and obtaining a target compound by Suzuki coupling, followed by deprotecting a Boc protective group;

method II:

using 5-bromo-2,4-dichloropyrimidine as a starting material, substituting with an aliphatic amine group and aminating in sequence to obtain a 5-bromo-pyrimidine-2,4-diamine intermediate, and processing the intermediate with Suzuki coupling before reacting with a brominated aromatic heterocyclic compound to obtain a target compound, followed by deprotecting a Boc protective group;

method III:

using 5-bromo-2,4-dichloropyrimidine as a starting material, substituting with an aliphatic amine group and aminating in sequence to obtain a 5-bromo-pyrimidine-2,4-diamine intermediate, acting the intermediate with a brominated aromatic heterocyclic compound, and then processing with Suzuki coupling and deprotecting a Boc protective group to obtain a target compound; or method IV:

using 5-bromo-2-aminopyrimidine as a starting material, reacting with a brominated aromatic heterocyclic compound before Suzuki coupling, reductive amination and deprotecting a Boc protective group in sequence to obtain a target compound.

9. A method for preparing antitumor drugs, comprising a step of using a therapeutically effective amount of a pharmaceutical composition comprising a compound of Formula (I) and an optical isomer or a pharmaceutically acceptable salt, wherein tumors are breast cancer, ovarian cancer, sarcoma, lung cancer, prostate cancer, colon cancer, rectal cancer, kidney cancer, pancreatic cancer, leukemia, lymphoma, neuroblastoma, glioma, head and neck cancer, thyroid cancer, liver cancer, vulvar cancer, cervical cancer, endometrial cancer, testicular cancer, bladder cancer, esophageal cancer, gastric cancer, nasopharyngeal carcinoma, buccal cancer, oral cancer, gastrointestinal stromal tumor, skin cancer, multiple myeloma, non-Hodgkin's lymphoma; the 2-substituted aromatic ring-pyrimidine comprises an optical isomer or a pharmaceutically acceptable salt.

* * * * *